US008333770B2

(12) United States Patent
Hua

(10) Patent No.: US 8,333,770 B2
(45) Date of Patent: Dec. 18, 2012

(54) SYSTEMS AND METHODS FOR PEDICLE SCREW STABILIZATION OF SPINAL VERTEBRAE

(76) Inventor: Sherwin Hua, Newhall, CA (US)

(*) Notice: Subject to any disclaimer, the term of this patent is extended or adjusted under 35 U.S.C. 154(b) by 0 days.

(21) Appl. No.: 13/245,227

(22) Filed: Sep. 26, 2011

(65) Prior Publication Data

US 2012/0016422 A1 Jan. 19, 2012

Related U.S. Application Data

(63) Continuation of application No. 13/082,346, filed on Apr. 7, 2011, and a continuation-in-part of application No. PCT/US2011/030612, filed on Mar. 30, 2011, which is a continuation-in-part of application No. PCT/US2010/029199, filed on Mar. 30, 2010, said application No. 13/082,346 is a continuation-in-part of application No. PCT/US2010/029199, which is a continuation-in-part of application No. PCT/US2009/059004, filed on Sep. 30, 2009, said application No. 13/082,346 is a continuation-in-part of application No. 13/122,388, filed as application No. PCT/US2009/059004 on Sep. 30, 2009.

(60) Provisional application No. 61/469,764, filed on Mar. 30, 2011, provisional application No. 61/101,932, filed on Oct. 1, 2008.

(51) Int. Cl.
*A61B 17/70* (2006.01)
*A61B 17/88* (2006.01)
(52) U.S. Cl. ............... 606/86 A; 606/279; 606/914
(58) Field of Classification Search .............. 606/86 A, 606/99, 105, 914
See application file for complete search history.

(56) References Cited

U.S. PATENT DOCUMENTS

| 4,448,191 | A | 5/1984 | Rodnyansky et al. |
| 5,092,866 | A | 3/1992 | Breard et al. |
| 5,242,443 | A | 9/1993 | Kambin |
| 5,306,275 | A | 4/1994 | Bryan |
| 5,672,175 | A | 9/1997 | Martin |
| 5,728,097 | A | 3/1998 | Mathews |
| 5,980,521 | A | 11/1999 | Montague et al. |
| 6,235,028 | B1 | 5/2001 | Brumfield et al. |

(Continued)

FOREIGN PATENT DOCUMENTS
WO WO 2008/039247 A2 4/2008
(Continued)

OTHER PUBLICATIONS

U.S. Appl. No. 13/122,388, filed Apr. 1, 2011, Hua.
(Continued)

*Primary Examiner* — Alvin J Stewart
*Assistant Examiner* — Julianna N Harvey
(74) *Attorney, Agent, or Firm* — Knobbe Martens Olson & Bear LLP

(57) ABSTRACT

The present application is directed to various spinal stabilization systems. The systems can include one or more guiding elements attached to screw members to assist in guiding rod implants and tools to desired locations within a patient. The guiding elements can include a plurality of wires, blades, or tabs. The guiding elements can be capable of criss-crossing or intersecting at or near an incision, such that only a single incision may be needed to perform a surgery. The guiding elements can also include telescoping features that allow the height of the guiding elements to be adjusted in use, thereby allowing multiple telescoping guiding elements to be used with the same incision.

30 Claims, 46 Drawing Sheets

U.S. PATENT DOCUMENTS

| | | |
|---|---|---|
| 6,485,491 B1 | 11/2002 | Farris et al. |
| 6,530,929 B1 | 3/2003 | Justis et al. |
| 6,793,656 B1 | 9/2004 | Mathews |
| 6,916,320 B2 | 7/2005 | Michelson |
| 6,929,606 B2 | 8/2005 | Ritland |
| 7,008,422 B2 | 3/2006 | Foley et al. |
| 7,011,660 B2 | 3/2006 | Sherman et al. |
| 7,063,725 B2 | 6/2006 | Foley |
| 7,066,961 B2 | 6/2006 | Michelson |
| 7,083,621 B2 | 8/2006 | Shaolian et al. |
| 7,179,225 B2 | 2/2007 | Shluzs et al. |
| 7,179,261 B2 | 2/2007 | Seivol et al. |
| 7,188,626 B2 | 3/2007 | Foley et al. |
| 7,250,052 B2 | 7/2007 | Landry et al. |
| 7,282,064 B2 | 10/2007 | Chin |
| 7,306,603 B2 | 12/2007 | Boehm, Jr. et al. |
| 7,326,210 B2 | 2/2008 | Jahng et al. |
| 7,468,064 B2 | 12/2008 | Bruneau et al. |
| 7,491,208 B2 | 2/2009 | Pond, Jr. et al. |
| 7,491,218 B2 | 2/2009 | Landry et al. |
| 7,497,869 B2 | 3/2009 | Justis |
| 7,520,879 B2 | 4/2009 | Justis et al. |
| 7,527,638 B2 | 5/2009 | Anderson et al. |
| 7,547,318 B2 | 6/2009 | Birkmeyer et al. |
| 7,575,581 B2 | 8/2009 | Lovell |
| 7,588,575 B2 | 9/2009 | Colleran et al. |
| 7,588,588 B2 | 9/2009 | Spitler et al. |
| 7,666,189 B2 | 2/2010 | Gerber et al. |
| 7,686,814 B2* | 3/2010 | Lim et al. ........................ 606/105 |
| 7,691,132 B2 | 4/2010 | Landry et al. |
| 7,708,763 B2 | 5/2010 | Selover et al. |
| 7,717,944 B2 | 5/2010 | Foley et al. |
| 7,749,233 B2* | 7/2010 | Farr et al. ........................ 606/104 |
| 7,758,584 B2 | 7/2010 | Bankoski et al. |
| 7,758,617 B2 | 7/2010 | Iott et al. |
| 7,763,055 B2 | 7/2010 | Foley |
| 7,776,051 B2 | 8/2010 | Colleran et al. |
| 7,824,410 B2 | 11/2010 | Simonson et al. |
| 7,846,093 B2 | 12/2010 | Gorek et al. |
| 7,875,031 B2* | 1/2011 | Chin et al. .................. 606/86 A |
| 7,955,355 B2* | 6/2011 | Chin .............................. 606/246 |
| 8,043,343 B2* | 10/2011 | Miller et al. .................. 606/279 |
| 8,052,720 B2* | 11/2011 | Kuester et al. ................ 606/246 |
| 8,075,565 B2* | 12/2011 | Wilcox et al. ............... 606/86 A |
| 2003/0171750 A1 | 9/2003 | Chin |
| 2003/0208203 A1* | 11/2003 | Lim et al. ........................ 606/61 |
| 2004/0039384 A1 | 2/2004 | Boehm, Jr. et al. |
| 2004/0138662 A1* | 7/2004 | Landry et al. ................... 606/61 |
| 2004/0147928 A1* | 7/2004 | Landry et al. ................... 606/61 |
| 2005/0043742 A1 | 2/2005 | Bruneau et al. |
| 2005/0065517 A1* | 3/2005 | Chin .............................. 606/61 |
| 2005/0131408 A1 | 6/2005 | Sicvol et al. |
| 2005/0131421 A1 | 6/2005 | Anderson et al. |
| 2005/0131422 A1 | 6/2005 | Anderson et al. |
| 2005/0192570 A1 | 9/2005 | Jackson |
| 2005/0192589 A1* | 9/2005 | Raymond et al. ............... 606/99 |
| 2005/0228380 A1 | 10/2005 | Moore et al. |
| 2006/0030872 A1 | 2/2006 | Culbert et al. |
| 2006/0089652 A1 | 4/2006 | Eckman |
| 2006/0235279 A1 | 10/2006 | Hawkes et al. |
| 2006/0241600 A1 | 10/2006 | Ensign et al. |
| 2006/0264942 A1 | 11/2006 | Lim et al. |
| 2006/0264962 A1 | 11/2006 | Chin et al. |
| 2007/0016188 A1 | 1/2007 | Boehm, Jr. et al. |
| 2007/0016198 A1 | 1/2007 | Boehm, Jr. et al. |
| 2007/0016199 A1 | 1/2007 | Boehm, Jr. et al. |
| 2007/0073294 A1* | 3/2007 | Chin et al. ....................... 606/61 |
| 2007/0078460 A1 | 4/2007 | Frigg et al. |
| 2007/0093814 A1 | 4/2007 | Callahan, II et al. |
| 2007/0106123 A1 | 5/2007 | Gorek et al. |
| 2007/0167954 A1 | 7/2007 | Sievol et al. |
| 2007/0191840 A1 | 8/2007 | Pond, Jr. et al. |
| 2007/0219854 A1 | 9/2007 | Mueller et al. |
| 2007/0233079 A1* | 10/2007 | Fallin et al. ..................... 606/61 |
| 2007/0233097 A1 | 10/2007 | Anderson et al. |
| 2007/0239159 A1* | 10/2007 | Altarac et al. ................... 606/61 |
| 2007/0270842 A1 | 11/2007 | Bankoski et al. |
| 2007/0299443 A1 | 12/2007 | DiPoto et al. |
| 2007/0299444 A1 | 12/2007 | DiPoto et al. |
| 2008/0009864 A1 | 1/2008 | Forton et al. |
| 2008/0015582 A1 | 1/2008 | DiPoto et al. |
| 2008/0039838 A1 | 2/2008 | Landry et al. |
| 2008/0045957 A1 | 2/2008 | Landry et al. |
| 2008/0071274 A1 | 3/2008 | Ensign |
| 2008/0077139 A1 | 3/2008 | Landry et al. |
| 2008/0086130 A1 | 4/2008 | Lake et al. |
| 2008/0097457 A1 | 4/2008 | Warnick |
| 2008/0114403 A1* | 5/2008 | Kuester et al. ................ 606/308 |
| 2008/0119849 A1 | 5/2008 | Beardsley et al. |
| 2008/0119850 A1 | 5/2008 | Sicvol et al. |
| 2008/0125788 A1 | 5/2008 | Cohen et al. |
| 2008/0125817 A1 | 5/2008 | Arnett et al. |
| 2008/0140075 A1 | 6/2008 | Ensign et al. |
| 2008/0140120 A1 | 6/2008 | Hestad et al. |
| 2008/0140132 A1 | 6/2008 | Perez-Cruet |
| 2008/0177269 A1* | 7/2008 | Seelig ............................ 606/90 |
| 2008/0262318 A1 | 10/2008 | Gorek et al. |
| 2009/0082819 A1 | 3/2009 | Blain et al. |
| 2009/0216278 A1* | 8/2009 | Song ............................ 606/264 |
| 2009/0221878 A1 | 9/2009 | Gorek |
| 2009/0221879 A1 | 9/2009 | Gorek |
| 2009/0222044 A1 | 9/2009 | Gorek |
| 2009/0222045 A1 | 9/2009 | Gorek |
| 2009/0222046 A1 | 9/2009 | Gorek |
| 2009/0234392 A1 | 9/2009 | Dziedzic et al. |
| 2009/0287061 A1 | 11/2009 | Feigenbaum et al. |
| 2010/0049206 A1 | 2/2010 | Biyani |
| 2010/0114182 A1* | 5/2010 | Wilcox et al. ............... 606/86 A |
| 2010/0249844 A1* | 9/2010 | Durrani ........................ 606/259 |
| 2011/0022088 A1* | 1/2011 | Forton et al. .................. 606/246 |
| 2011/0196426 A1* | 8/2011 | Peukert et al. ................ 606/279 |
| 2011/0196429 A1 | 8/2011 | Hua |
| 2011/0238117 A1* | 9/2011 | Geist et al. .................... 606/263 |
| 2011/0270324 A1 | 11/2011 | Hua |
| 2011/0282390 A1 | 11/2011 | Hua |
| 2011/0301647 A1* | 12/2011 | Hua ............................ 606/279 |
| 2012/0016423 A1 | 1/2012 | Hua |
| 2012/0065693 A1* | 3/2012 | Lim et al. ................... 606/86 A |

FOREIGN PATENT DOCUMENTS

| | | |
|---|---|---|
| WO | WO 2008/136802 A1 | 11/2008 |
| WO | WO 2010/039817 A2 | 4/2010 |
| WO | WO 2010/039817 A3 | 7/2010 |
| WO | WO 2010/039817 A4 | 9/2010 |
| WO | WO 2011/040986 A1 | 4/2011 |

OTHER PUBLICATIONS

U.S. Appl. No. 13/082,346, filed Apr. 7, 2011, Hua.
U.S. Appl. No. 13/098,325, filed Apr. 29, 2011, Hua.
U.S. Appl. No. 13/189,432, filed Jul. 22, 2011, Hua.
U.S. Appl. No. 13/246,342, filed Sep. 27, 2011, Hua.
Notification of Transmittal of the International Search Report and the Written Opinion of the International Searching Authority, or the Declaration dated May 25, 2010 for International Application No. PCT/US2009/059004.
Notification of Transmittal of the International Search Report and the Written Opinion of the International Searching Authority, or the Declaration dated Oct. 18, 2010 for International Application No. PCT/US2010/029199.
International Preliminary Report on Patentability for International Application No. PCT/US2009/059004 dated Apr. 14, 2011.
Notification of Transmittal of the International Search Report and the Written Opinion of the International Search Authority, or the Declaration dated Jun. 6, 2011 for International Application No. PCT/US2011/030612.
Medtronic Sofamor Danek METRx System Surgical Technique "Minimal Access Spinal Technologies" article, 22 pages, 2004.
K2M Complex Spine Innovations, Mesa Spinal System Lumbar Products for Surgeons Treating Spinal Disorders, 1 page. Downloaded May 6, 2010.
K2M Complex Spine Innovations, "Serengeti Minimally Invasive Retractor System. A Simple Approach to Complex Spine," 2 pages, 2009.

* cited by examiner

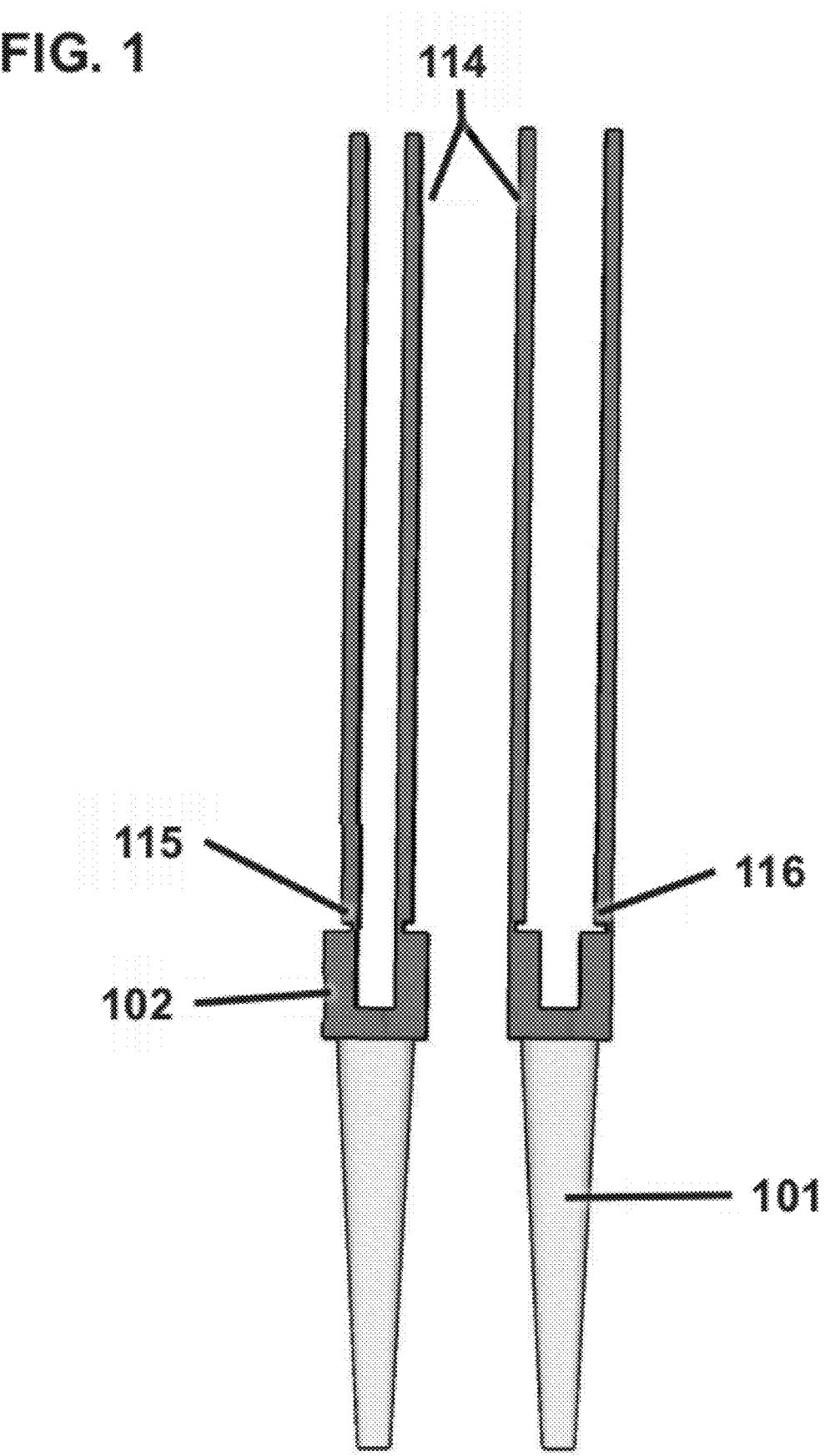

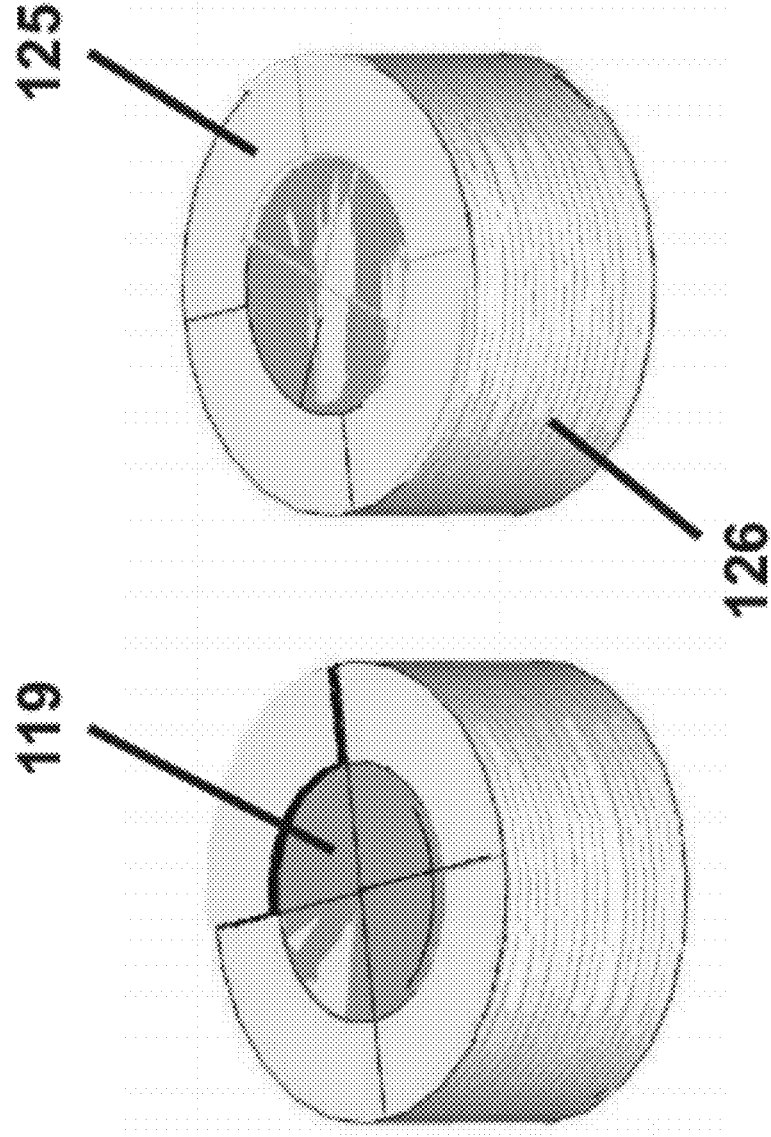

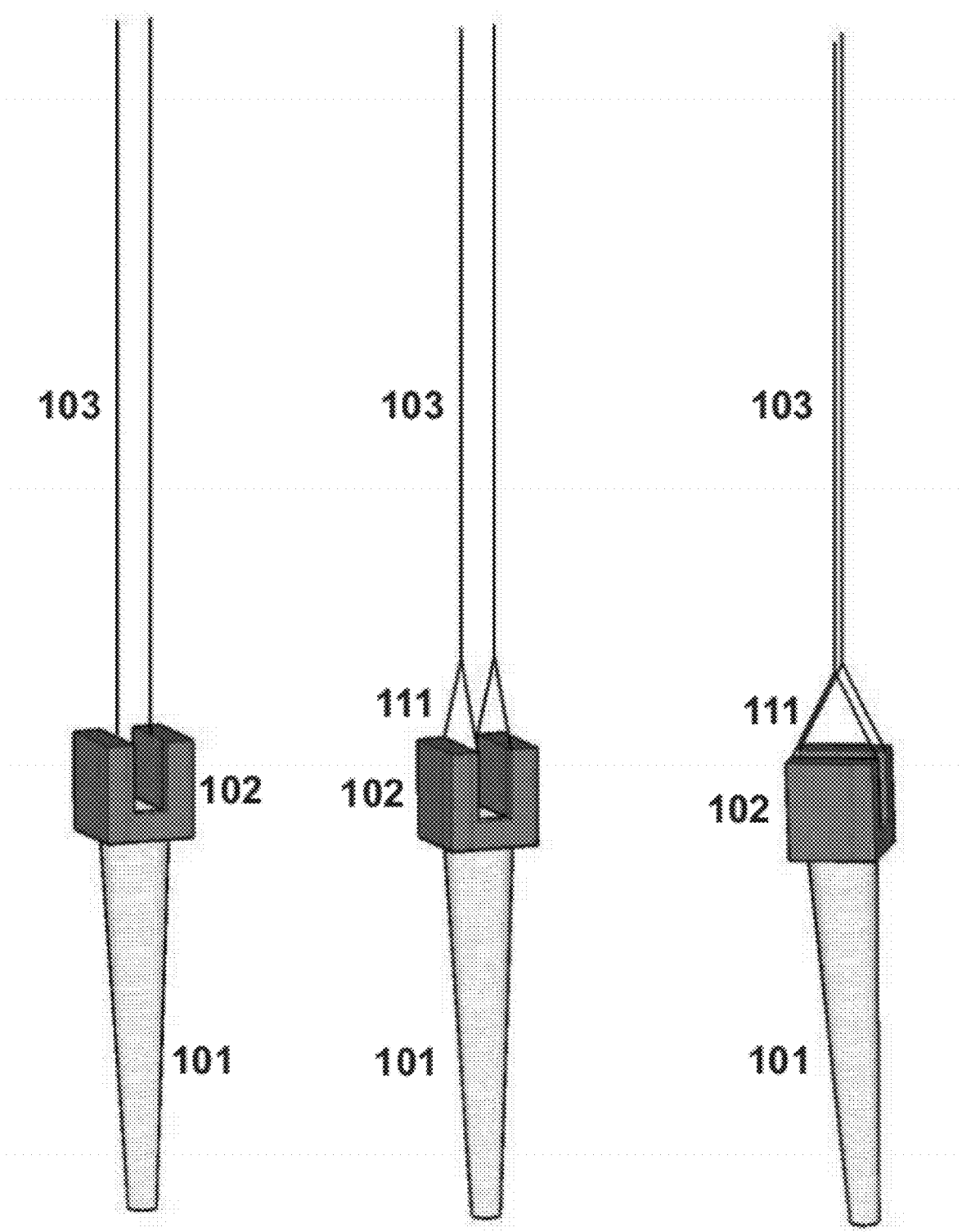

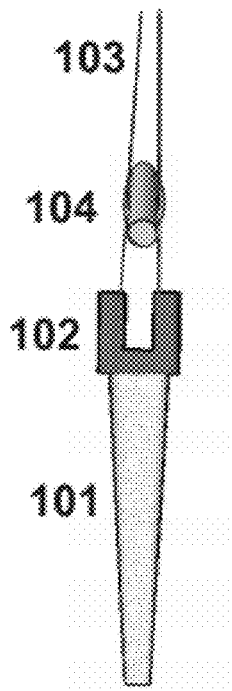
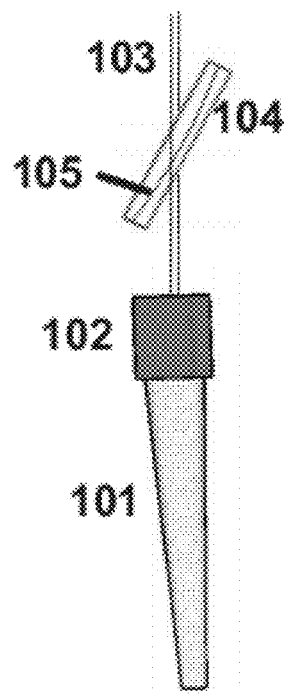
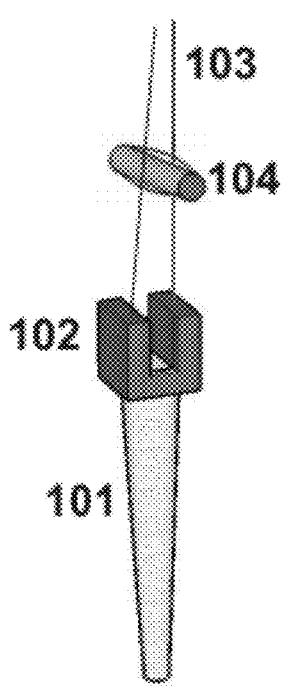
FIG. 19A     FIG. 19B     FIG. 19C
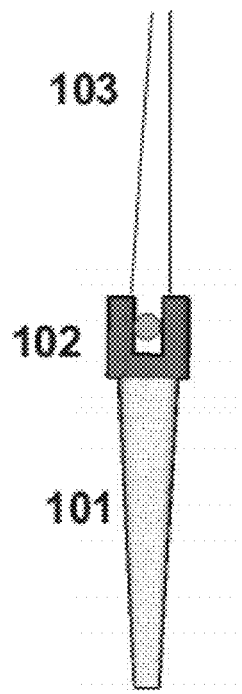
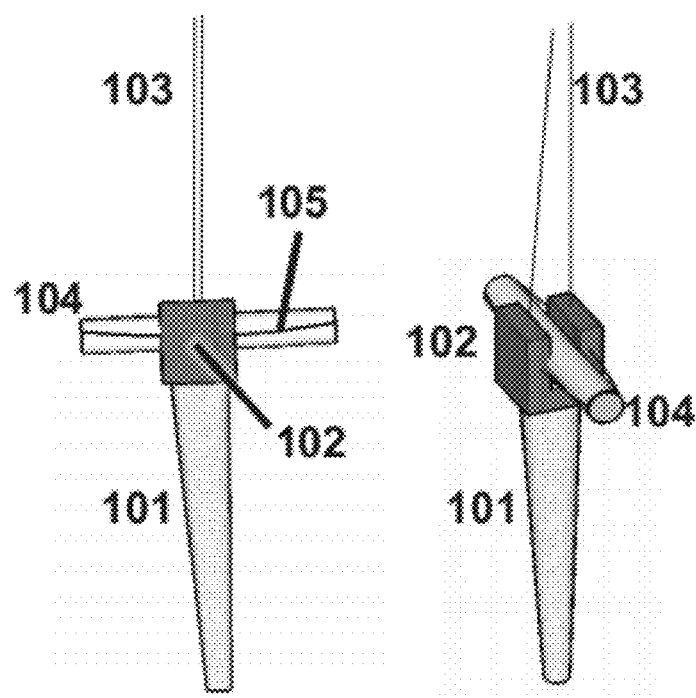
FIG. 19D     FIG. 19E     FIG. 19F

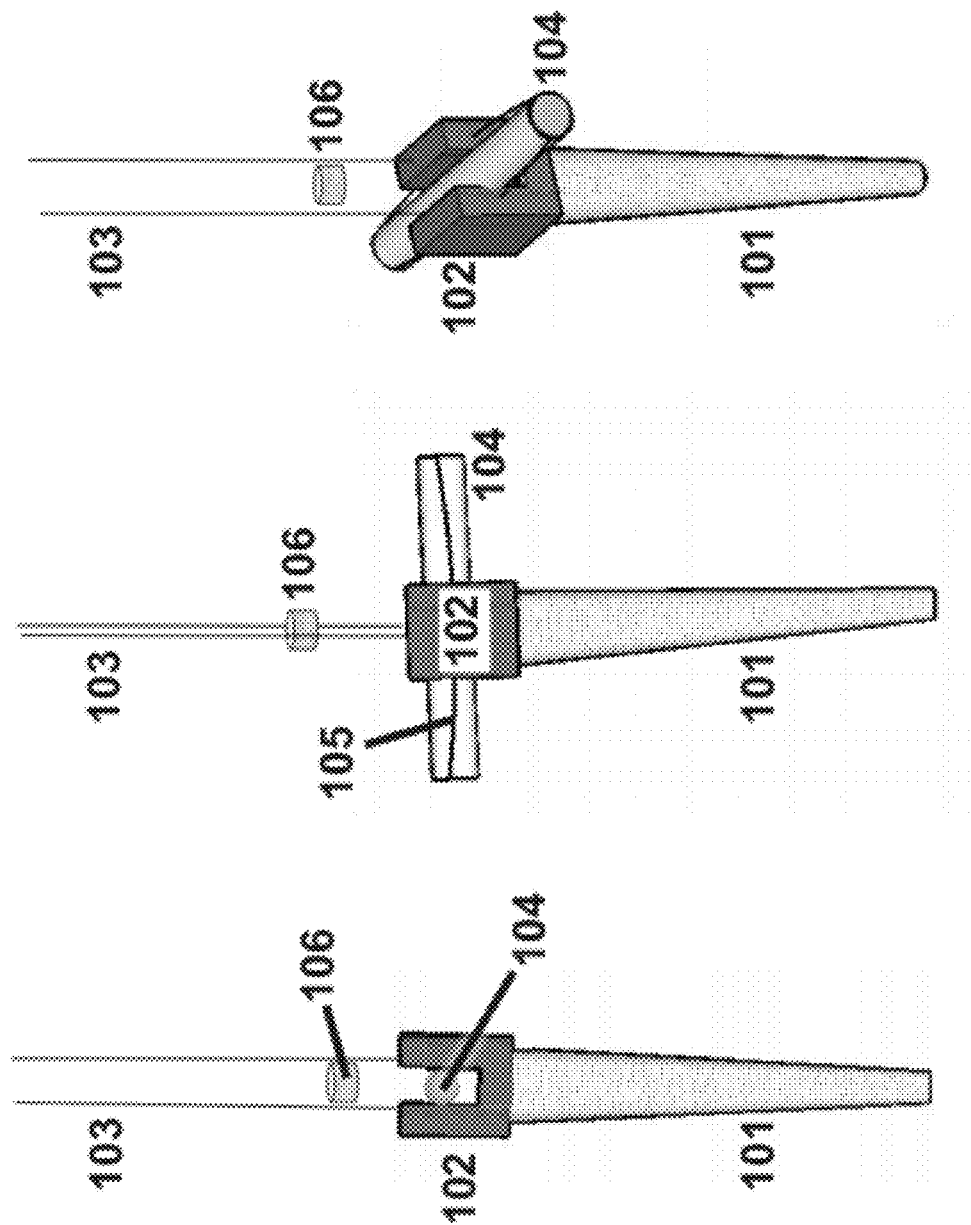

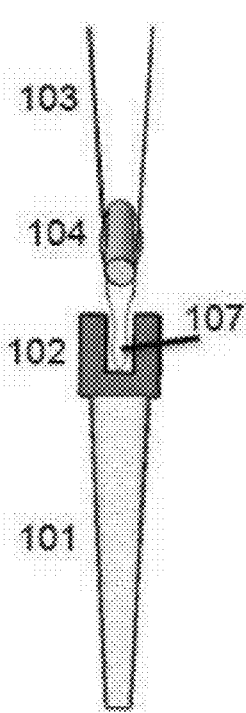 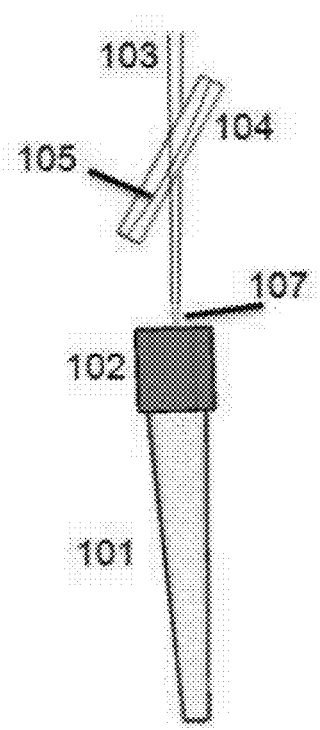 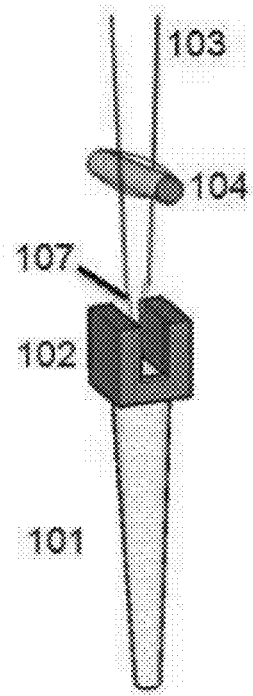
FIG. 21A  FIG. 21B  FIG. 21C
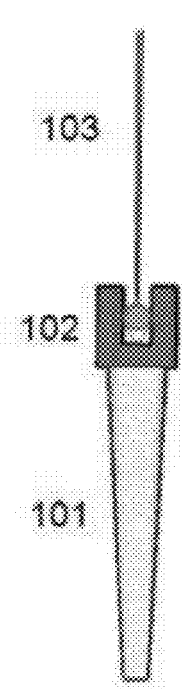 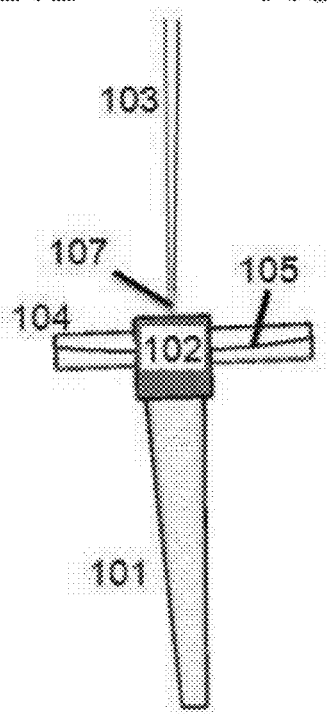 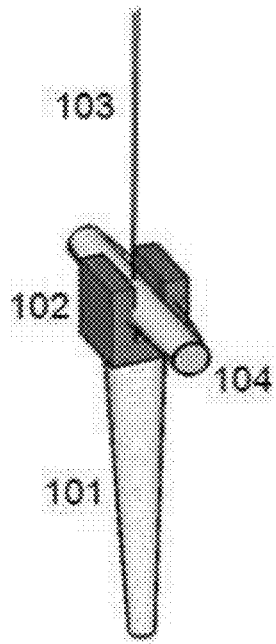
FIG. 21D  FIG. 21E  FIG. 21F

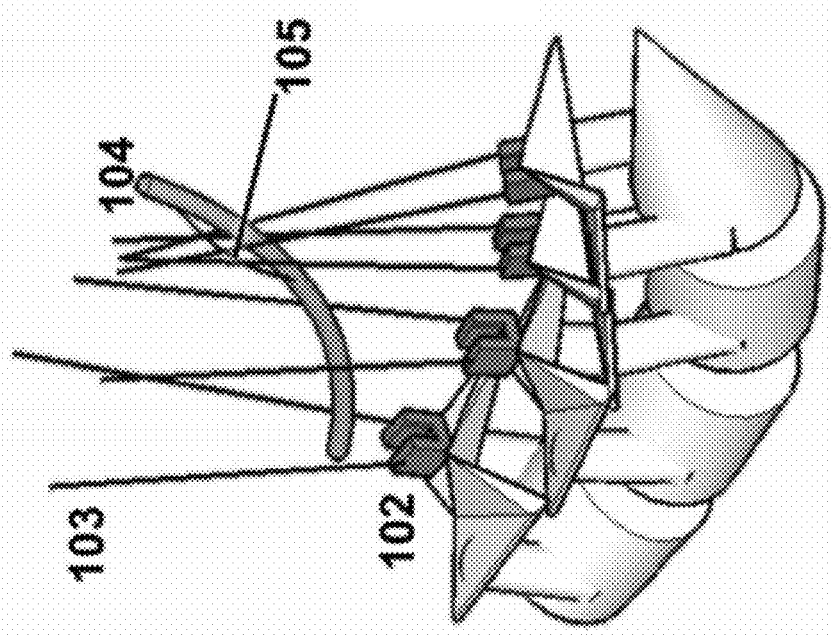
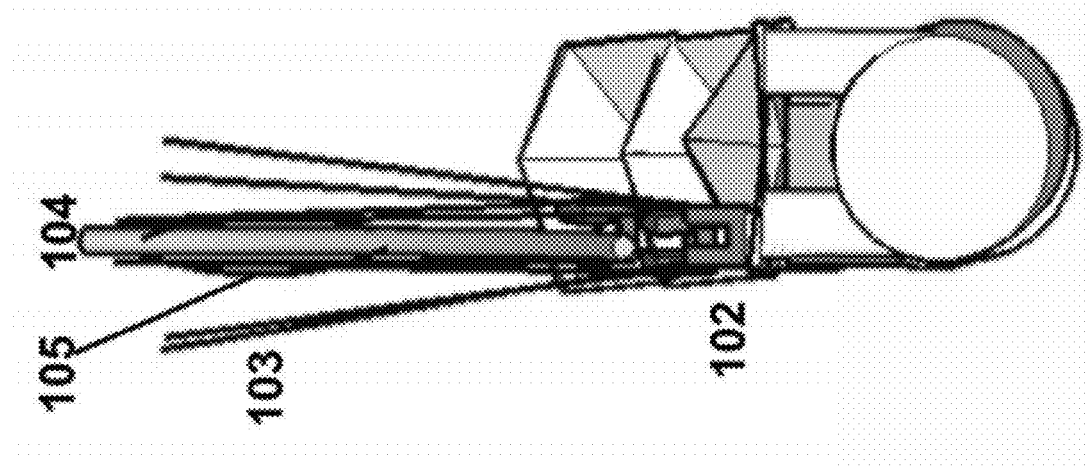
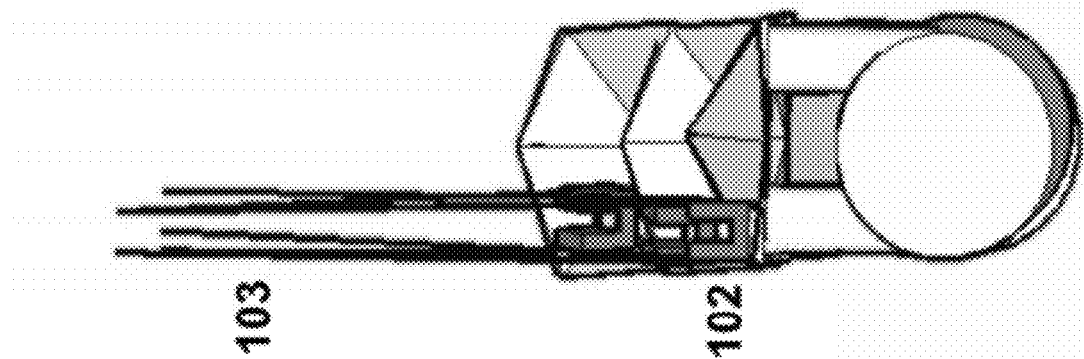
FIG. 23C
FIG. 23B
FIG. 23A

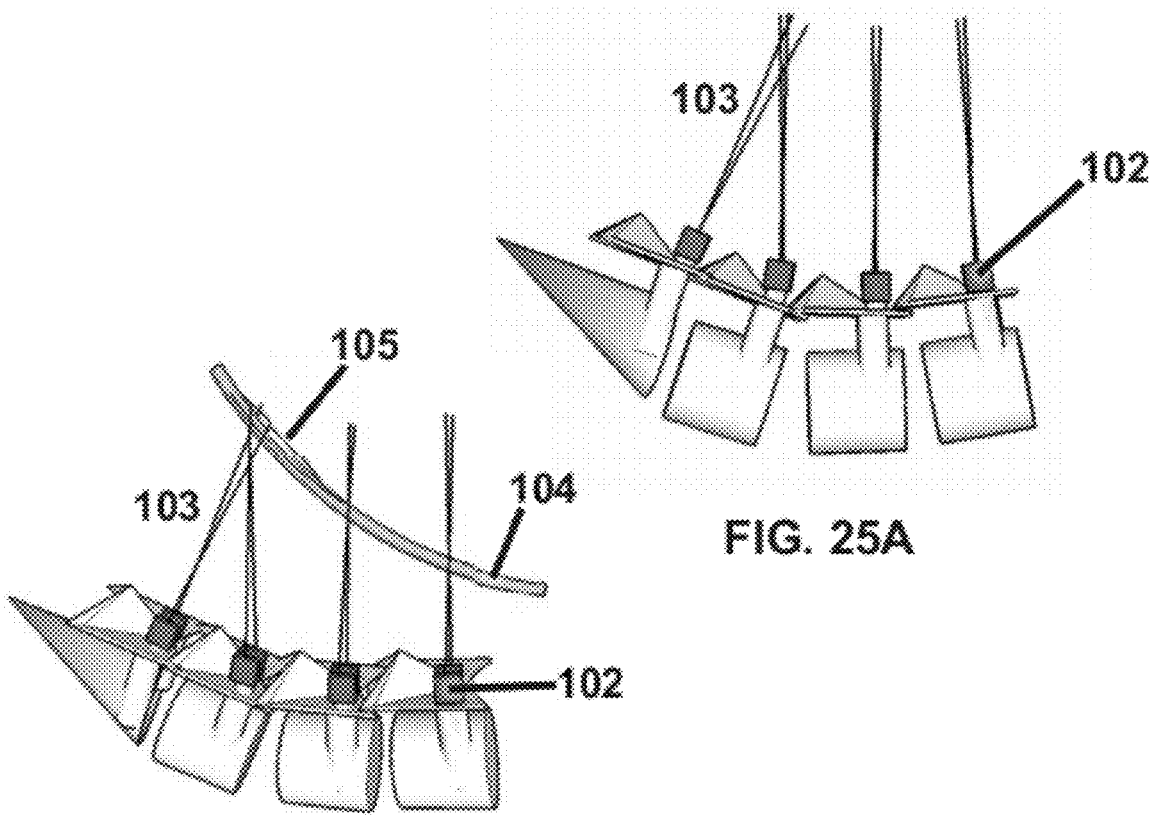
FIG. 25A
FIG. 25B
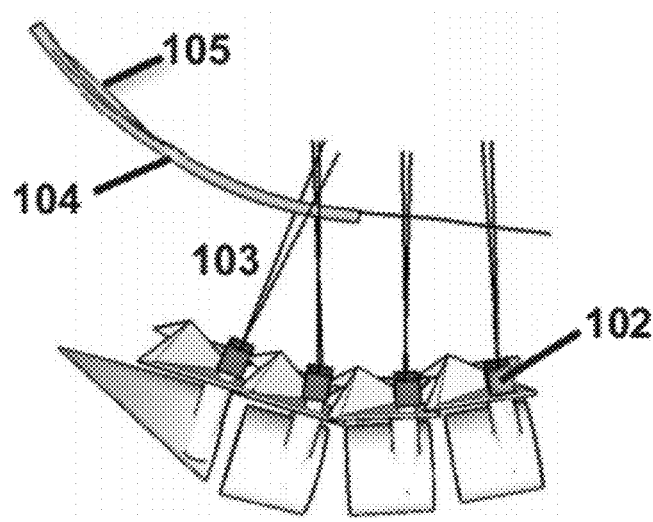
FIG. 25C

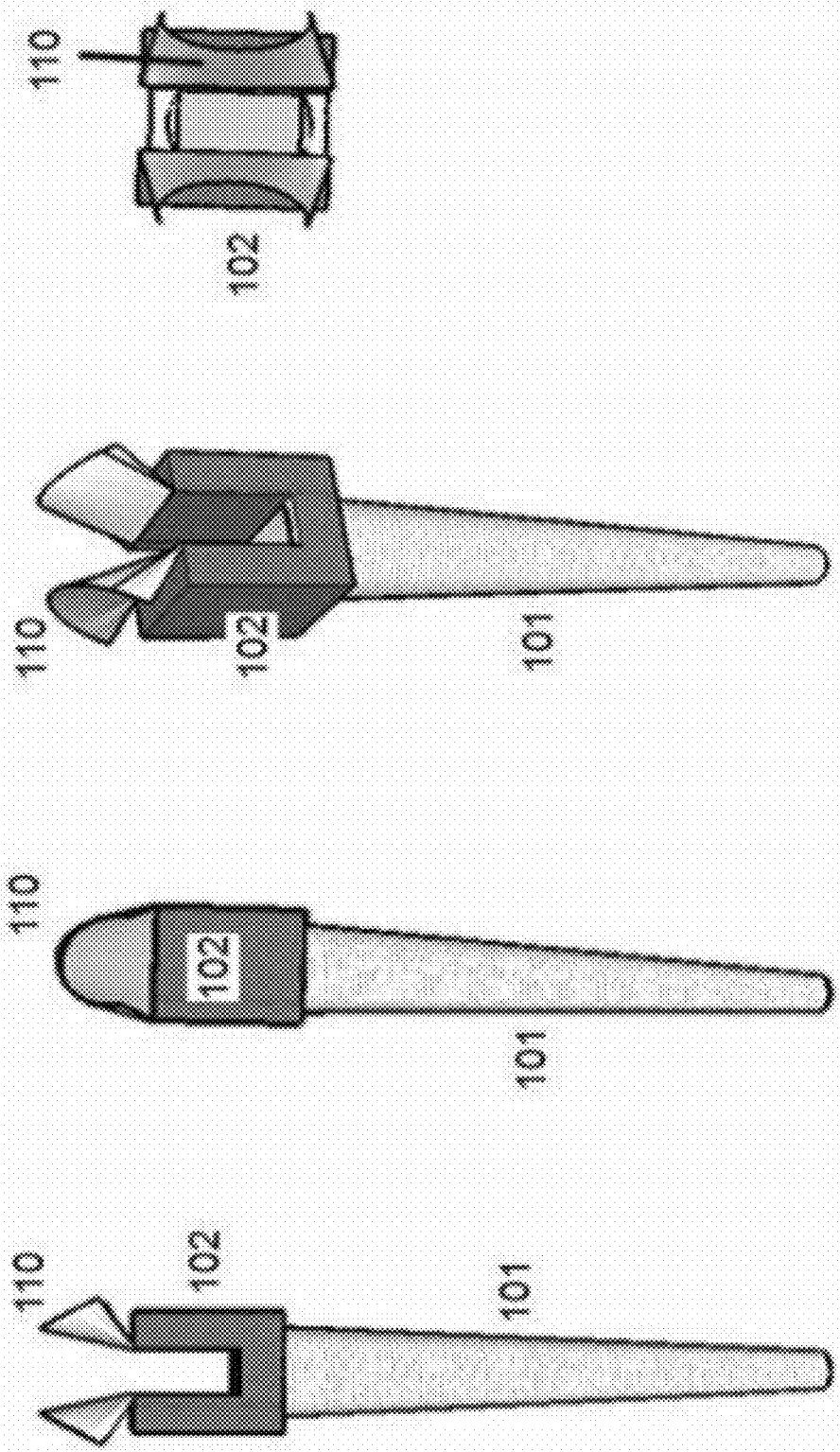

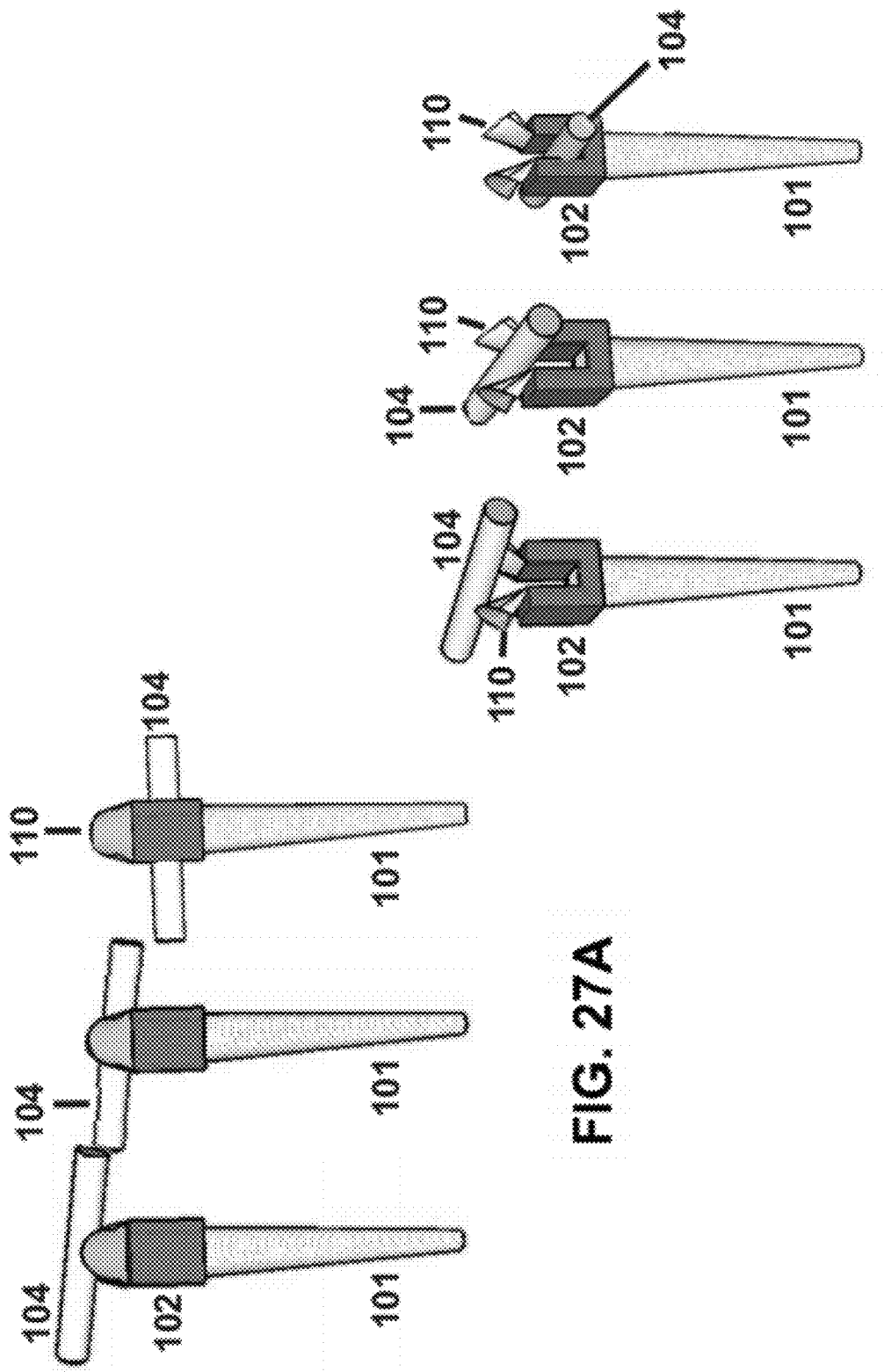

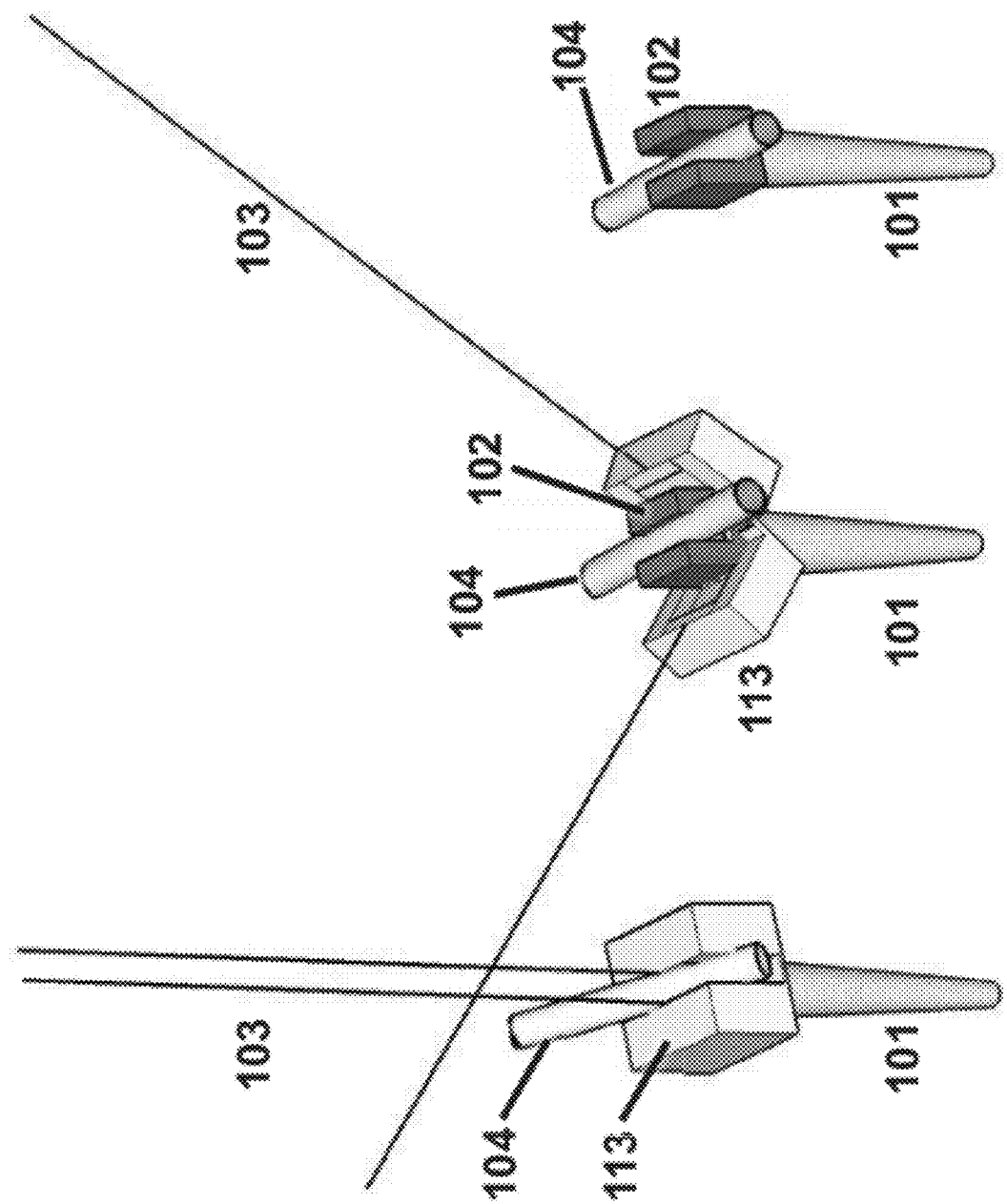

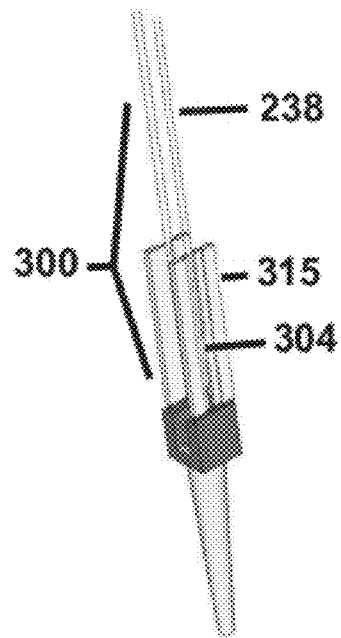 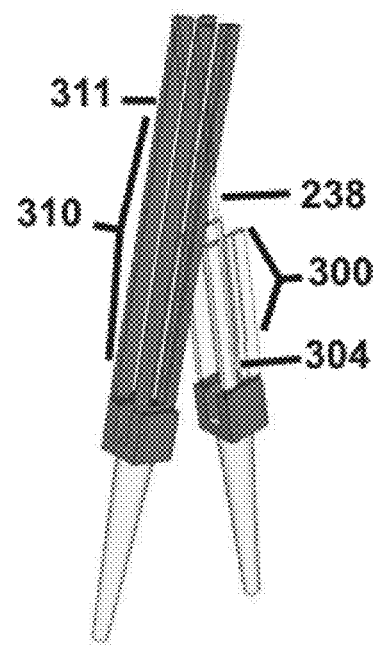 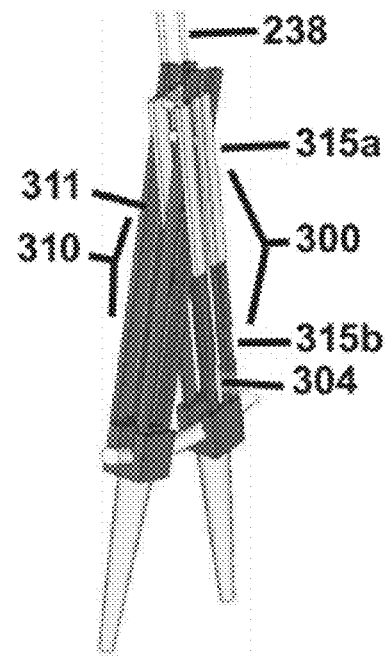
FIG. 34A  FIG. 34B  FIG. 34C
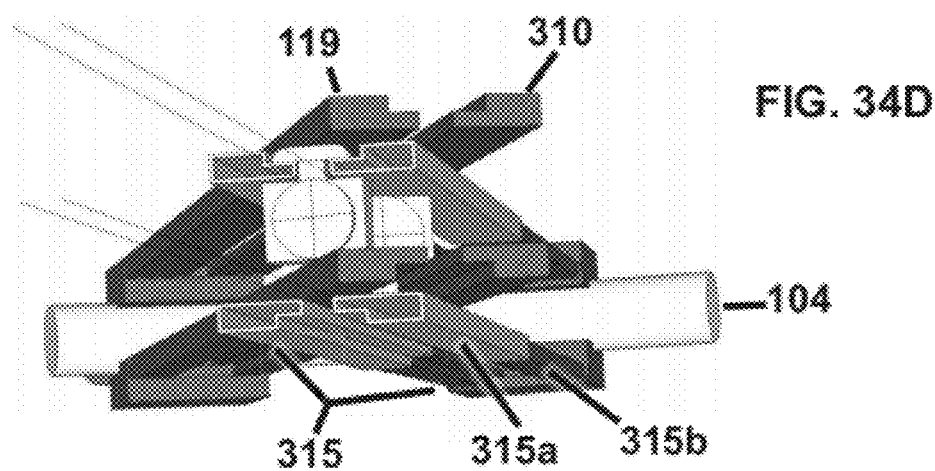
FIG. 34D

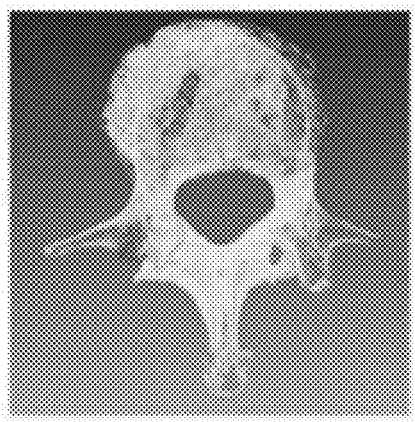
FIG. 37A
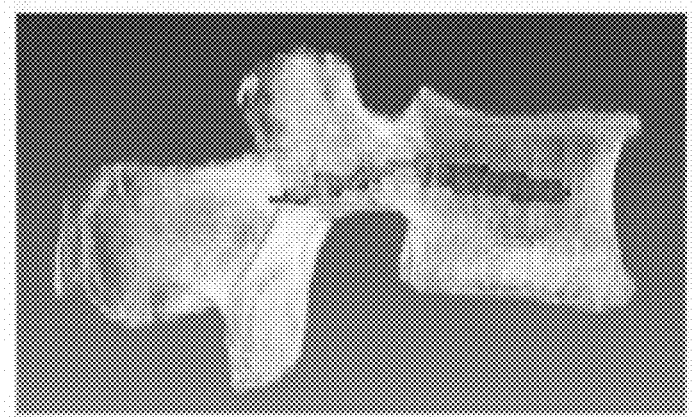
FIG. 37B
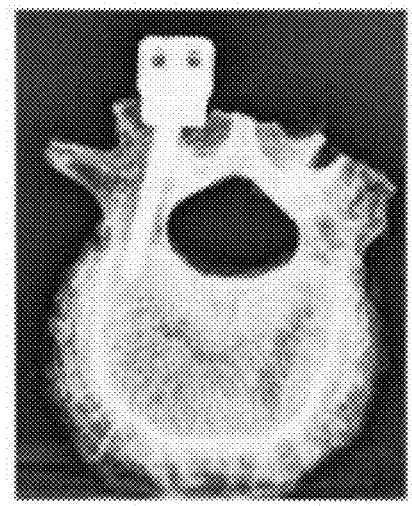 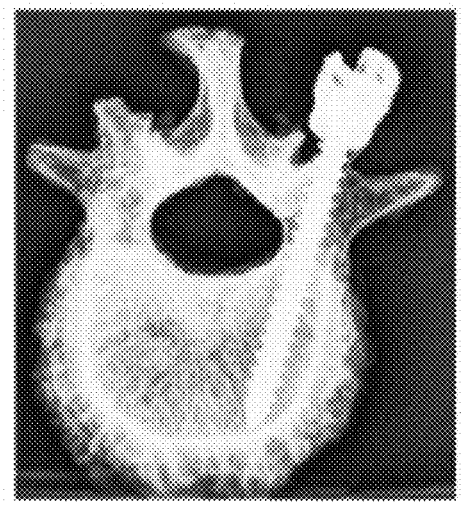
FIG. 37C	FIG. 37D

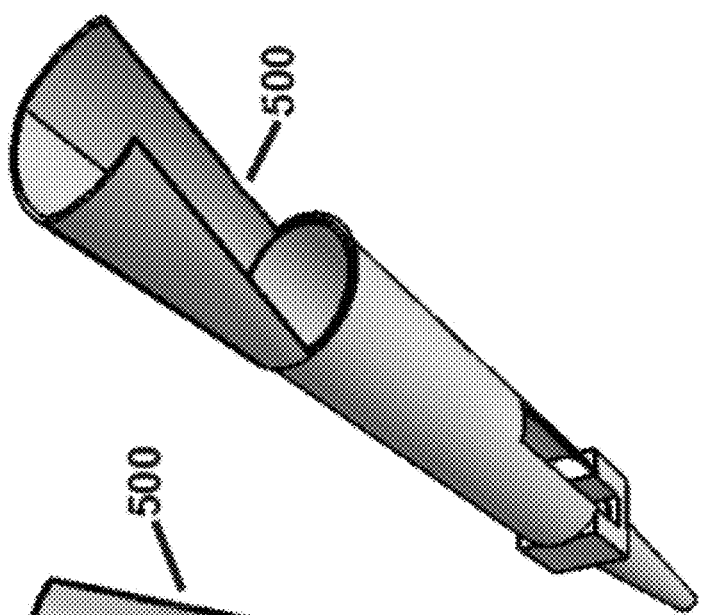
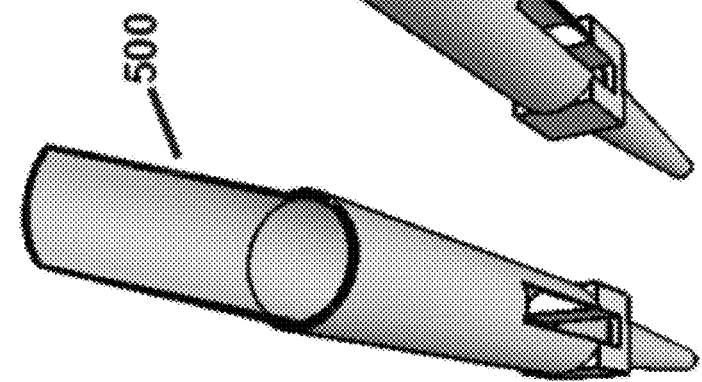
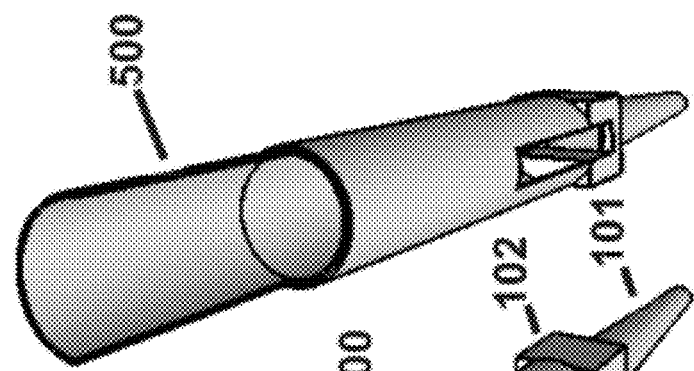
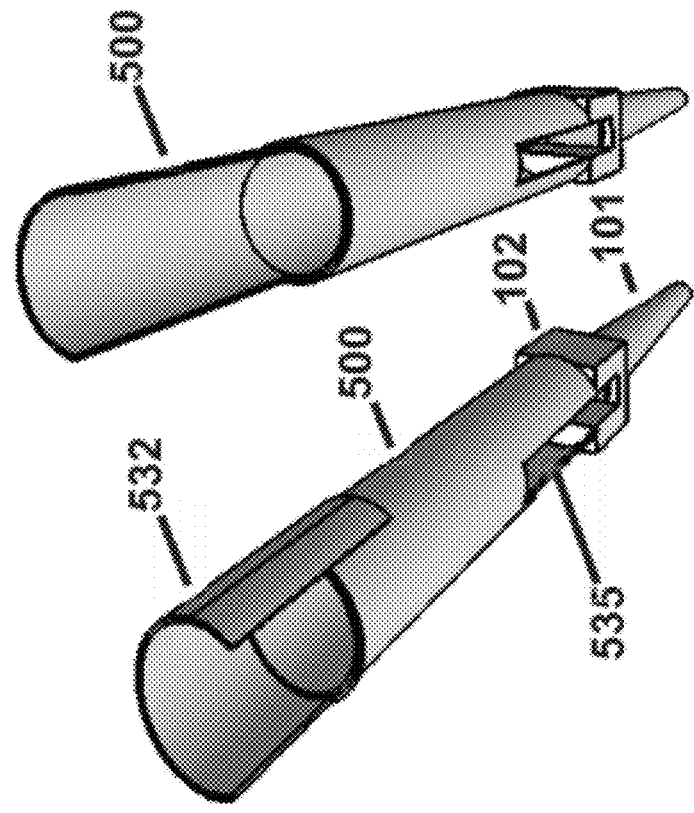

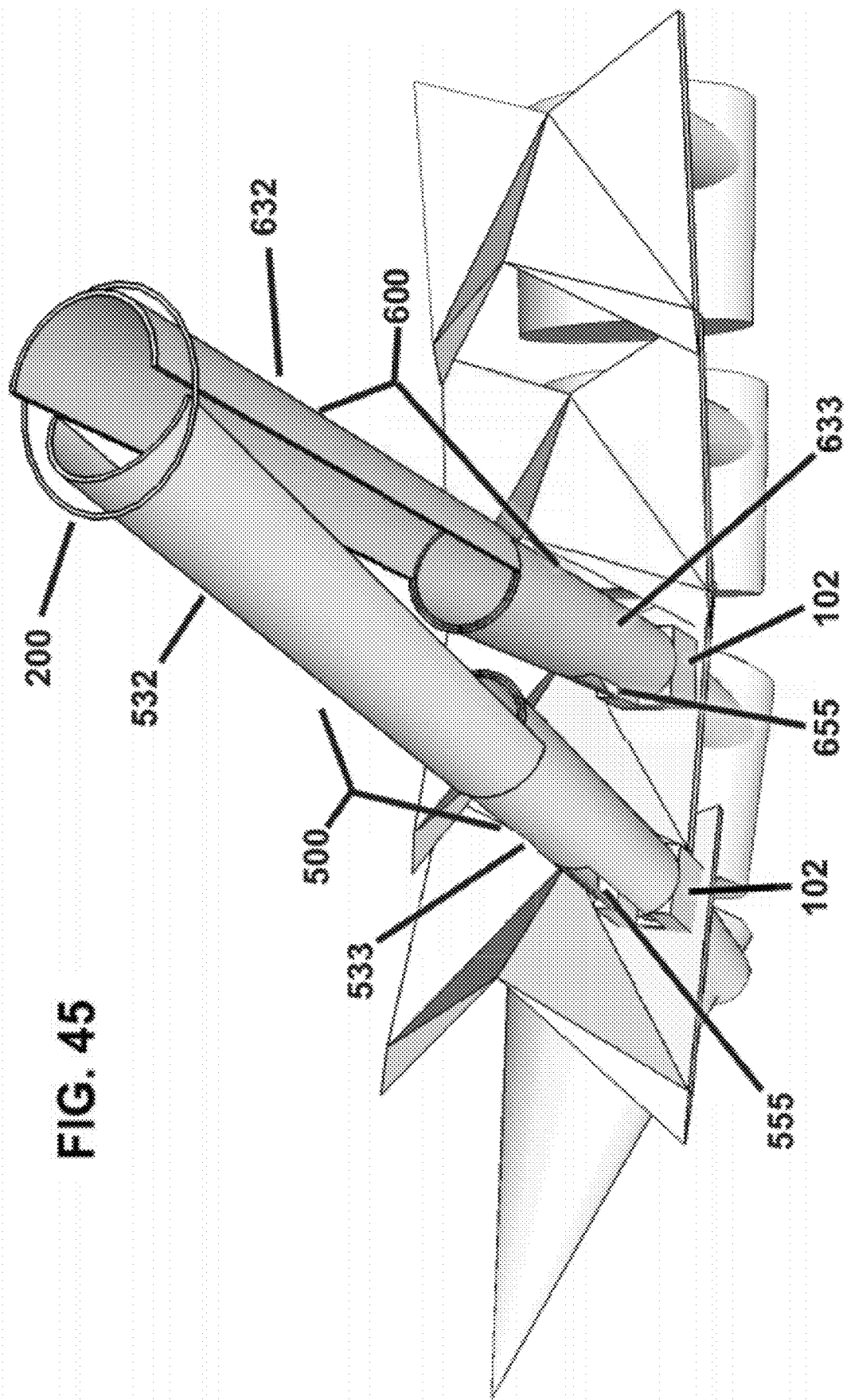

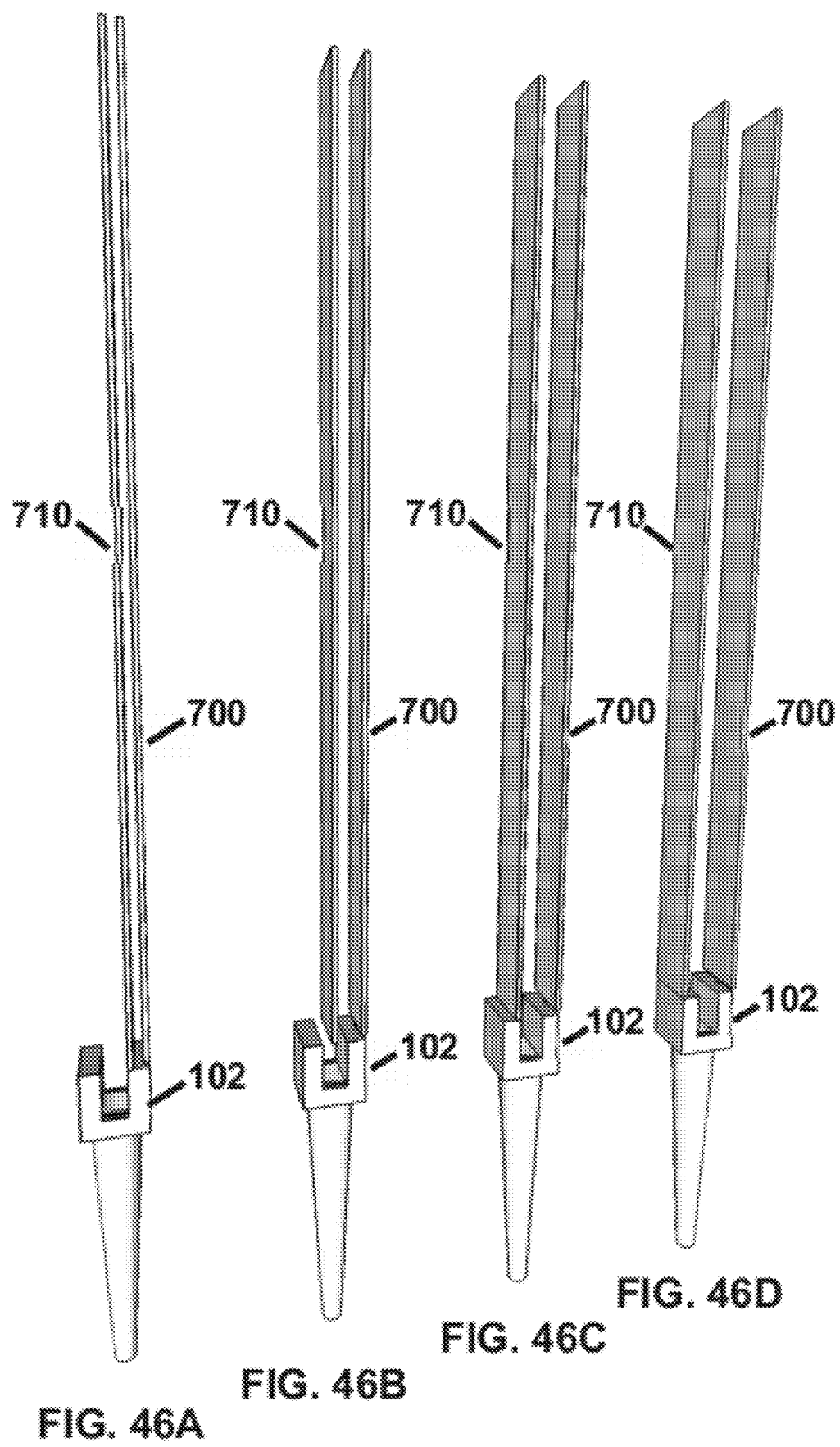

SYSTEMS AND METHODS FOR PEDICLE SCREW STABILIZATION OF SPINAL VERTEBRAE

CROSS-REFERENCE TO RELATED APPLICATIONS

This application is a continuation of U.S. application Ser. No. 13/082,346, filed Apr. 7, 2011, which claims the benefit of U.S. Provisional Application No. 61/469,764, filed Mar. 30, 2011; U.S. application Ser. No. 13/082,346 is also a continuation-in-part of International Application No. PCT/US2011/030612, filed Mar. 30, 2011, which claims priority to International Application No. PCT/US2010/029199, filed Mar. 30, 2010; U.S. application Ser. No. 13/082,346 is also a continuation-in-part of International Application No. PCT/US2010/029199, filed Mar. 30, 2010, which claims priority to International Application No. PCT/US2009/059004, filed Sep. 30, 2009; U.S. application Ser. No. 13/082,346 is also a continuation-in-part of U.S. application Ser. No. 13/122,388, filed Apr. 1, 2011, which is the U.S. national phase of International Application No. PCT/US2009/059004, filed Sep. 30, 2009, published as WO 2010/039817 A2, WO 2010/039817 A3 and WO 2010/039817 A4, which claims the benefit of U.S. Provisional Application No. 61/101,932, filed Oct. 1, 2008. All of the aforementioned applications and publications are hereby incorporated by reference in their entireties.

BACKGROUND

1. Field of the Invention

The present invention relates to medical devices, systems and methods for bone fixation. Specifically, embodiments of the invention are related to stabilizing adjoining vertebrae in the cervical, thoracic, and lumbosacral spine. In addition, embodiments of the invention are related to fusion or stabilization of vertebrae in the lumbar spine to alleviate axial back pain. Embodiments of the invention are also related to improving minimally invasive surgical (MIS) approaches to pedicle screw fusion by reducing the number and size of incisions and the size of the medical instruments inserted therein.

2. Description of the Related Art

While some lower back conditions can be ameliorated with non-surgical approaches, spinal fusion is recommended for certain conditions when non-surgical approaches fail. Non-surgical approaches include medications, physical therapy, chiropractic treatment, traction, epidural steroid injections, facet blocks or rhizotomy, weight loss, smoking cession, and acupuncture. Conditions that commonly serve as indications for spinal fusion or stabilization surgery can be divided generally into three categories: (i) trauma induced, (ii) curvature, and (iii) degenerative.

Trauma induced conditions include fractures and ligamentous injuries. Fractures typically result from an unfortunate incident involving an extraneous force or fall but may also arise from pathologic conditions, such as cancer or osteoporosis. Fractures are often compressive in nature and typically lead to a pathological curving of the spine resulting in a loss of the natural lordotic curvature in the lumbar and cervical spine, known as kyphosis. Fractures of the spine also occur with translational or rotational forces perpendicular to the axis of the spine. These forces result in fractures of the facet or pars interarticularis (pars). If the external forces are large enough, vertebrae can collapse resulting in a burst fracture that can injure all 3 columns of the vertebrae (anterior, middle, and posterior columns). Many traumatic injuries can heal without surgery, but unstable injuries that pose a risk for neurologic injury and/or pain require stabilization through a procedure such as fusion.

A condition called spondylolisthesis characterized by slippage of the spine bones or vertebrae relative to one another can result from fractures of the pars interarticularis (pars fracture) known as spondylolysis. Spondylolisthesis can also develop from malformation of the facet joints by degenerative arthritis as well as congenital malformation and pathologic conditions such as tumors. If the pars on both sides are fractured, then the spinous process and lamina are essentially completely disconnected from the pedicle and vertebral body. This large fragment is called the Gill body. Pars fractures are actually common in people of all ages (often acquired in the teenage years). While, many of these patients are mildly symptomatic and do not require surgery, those with progressive symptoms may require surgical decompression with or without fusion. Spondylolisthesis results in misalignment of the spine and increases the risk of a nerve becoming entrapped. Nerves travel within the spinal canal bounded by the vertebrae and their roots protrude from the curved openings in the sides of the vertebrae called foramina (singular is foramen). These spinal nerves are suspected to be the source of back and radicular pain when they become entrapped or when the nerve endings become irritated by irregular or abrasive motion around a disc, bone, or joint. Spondylolisthesis can also aggravate or be accompanied by degeneration of disc or facet joint which can lead to axial back pain.

The normal curvature of the lumbar and cervical spine is lordosis, where the posterior aspect of these spinal levels forms a concave curve. The thoracic spine normally has a kyphotic or convex curve. Curvature conditions include straightening of the natural curvature as well as abnormal lordosis, abnormal kyphosis or lateral/rotational bending called scoliosis. Curvature conditions can occur idiopathically during adolescence, e.g., adolescent idiopathic scoliosis, or develop as a secondary problem in situations where spinal muscle activation is abnormal such as cerebral palsy, spina bifida, or tethered cord syndrome. Abnormal spinal curvature is common in spinal degeneration when the discs and joints degenerate asymmetrically leading to a progressive curvature (scoliosis, kyphosis, or lordosis) as the biomechanics of the spine are disrupted. Curvature conditions also occur after trauma with compression or burst fractures or with ligamentous injury. Additionally, curvature conditions can occur iatrogenically after previous spinal surgery where the anatomy and biomechanics of the spine have been altered. Such situations include the removal of the posterior tension band after laminectomy as well as the alteration of physiologic movement after spinal fusion leading to adjacent level compensation and degeneration. Curvature conditions lead to abnormal biomechanical stress on the discs and facet joints accompanied by compensatory measures such as facet or ligamentous hypertrophy. Patients can develop both axial back pain and radicular pain. In patients who have failed conservative therapy and bracing, surgery can be effective. Surgery in these conditions includes decompression of nerve or spinal cord compression as well as fusion or stabilization. Curvature can be corrected through surgery, and fusion prevents further curvature from developing.

Degenerative conditions include spinal arthritis and recurrent disc herniation. Spinal arthritis is the most common indication for fusion and may exist in the form of severe disc degeneration (also called Degenerative Disc Disease, DDD) or facet disease. Degenerative arthritis can also be a cause of spondylolisthesis in addition to traumatic fractures discussed above. Degenerative conditions are generally accompanied by nerve compression causing radicular pain in the distribution of the nerve's receptive field, which usually correlates with and is manifested in arm or leg pain. Pure nerve compression syndromes such as herniated nucleus pulposus (herniated discs) or foraminal stenosis (narrowing of the side foramina canals through which the nerves pass) can often be treated with decompression without fusion. Pure disc degeneration syndromes can be treated with fusion without decompression of the nerves. However, most commonly disc degeneration occurs in combination with nerve compression causing both axial back pain and radicular limb pain. In these circumstances fusion surgery is combined with nerve decompression surgery.

Fusion functions to eliminate motion in the disc space and facet joints between adjacent vertebrae. The vertebrae provide the rigid structural framework of the spine and the fibrocartilaginous disc space acts as a cushion or shock-absorber. Degradation of the disc space can distort alignment and alter the biomechanical cushion that the disc affords the adjacent vertebrae. This degradation alters the forces impacted upon the vertebrae and results in axial back pain. Fusion is designed to eliminate movement between adjacent vertebrae by either forming a solid bridge of bone across the disk space and/or creating new bone formation in the posterolateral space to provide stabilization, rigidity, and strength. Sometimes fusion involves a bone graft taken from another location in the body (e.g., autograft from the iliac crest in the pelvis) or from an external source, e.g., allograft. Physicians commonly refer to the level of a fusion. A single level fusion involves stabilizing the two vertebral bones adjacent to a diseased disc. A two-level fusion involves stabilizing three adjacent vertebral bones spanning two problematic disc spaces. Each vertebra makes contacts (joints) with adjacent vertebrae at three points, the paired facet joints located posteriorly and the intervertebral disc located anteriorly. Thus, lumbar fusion can be directed either at the posterior facet joints or at the anterior interbody/disc space or both. When an anterior interbody fusion is performed in combination with posterior fusion, the procedure is termed 360° fusion. One commonly used technique of posterolateral fusion is pedicle screw fusion where screws are directed into the pedicle portions and the bodies of adjacent vertebrae and then rods are connected to the screws across the disc spaces. The screws and rods hold the adjacent vertebrae motionless relative to one another and allow the bone graft that is placed either in the interbody (disc) space or in the posterolateral space to grow into solid bone. Conventional pedicle screws and rods are metal, typically titanium (Ti) alloy but have been made from stainless steel as well. Recently rods have been made from a minimally flexible polymer called polyetheretherketone (PEEK).

Interbody fusion involves placing one or more spacers (typically pre-loaded with bone graft material) within the interbody (disc) space between bony vertebral bodies after the degenerated disc has been cleaned out and removed. Spacers are made from bone grafts, titanium, carbon fiber, or polymers such as PEEK. Interbody fusion can be performed through several approaches including: an anterior approach (anterior lumbar interbody fusion, ALIF), a posterior approach (posterior lumber interbody fusion, PLIF, or transforaminal lumbar interbody fusion, TLIF), or a lateral approach (direct lateral interbody fusion, DLIF™—Medtronic, or extreme lateral interbody fusion, XLIF™—Nuvasive). The aim of these approaches is to remove the degenerated disc and replace the disc with material that induces bony fusion. Alternatively the disc can be replaced with an artificial joint/disc (discussed below). Each of these interbody approaches has advantages and disadvantages.

Anterior procedures require a retroperitoneal dissection and risk injury to the large blood vessels anterior to the lumbar vertebrae. Also injury to the nerve plexus anterior to the vertebrae can result in sexual dysfunction. The lateral approach is promising but is limited to the upper and mid lumbar levels (rostral to L5,S1) because of obstruction by the iliac crest. The posterior interbody approach is more time consuming and typically requires more muscle dissection and retraction. However, the posterior approach allows the placement of the interbody graft, posterior pedicle screw fusion, and decompression of nerves all to occur through the posterior incision(s).

Although anterior and lateral approaches can be performed stand-alone (without posterior instrumentation), many surgeons will back-up or supplement anterior or lateral interbody fusions by placing pedicle screws posteriorly after the interbody cage or graft has been placed. This 360° fusion limits movement more than just an isolated anterior or posterior fusion, and fusion rates are increased. However in ALIF and lateral interbody (DLIF, XLIF) cases, two sets of incisions are required for a 360° fusion.

The posterior approaches (TLIF and PLIF) allow an interbody fusion, pedicle screw fusion, and neural decompression to be done all through the same posterior incision(s). In the TLIF, a single large interbody spacer is inserted on the side ipsilateral to the patient's symptomatic side after neural decompression is completed. If both sides are symptomatic then decompression is required on both sides. A PLIF is performed by placing two interbody spacers, one on each side. Posterior procedures may be done according to: (i) an invasive open procedure in which a large incision and/or several incisions are made, (ii) a percutaneous approach in which small incisions and/or few incisions are made, and potentially (iii) an endoscopic approach in which small incisions are made and all tools and devices are inserted through portals with visualization provided on an external monitor.

As an alternative to fusion, recent advances in interbody stabilization have resulted in the development of artificial disc technology. Artificial discs replace the degenerated discs and allow continued motion at the joint. Both cervical and lumbar artificial discs have been developed. Additionally, dynamic stabilization techniques have been developed for the posterior spine. These posterior techniques utilize pedicle screws and a dynamic rod. Typically the dynamic rod has a mechanism to bend under certain loads or forces, thereby absorbing some stress and strain that is applied to the spine. The advantage of dynamic stabilization is that motion is preserved in the spine. However, the durability of these systems may be an issue. In fusions, the bone graft (interbody or posterolateral) eventually fuses the vertebrae eliminating the need for the spinal instrumentation (screws and rods). However in dynamic stabilization, fusion does not occur, so the screws and dynamic rods will always be subjected to the strain and forces of the spine. Over time the possibility of loosening of the pedicle screws or mechanical failure may increase. Sometimes the use of a slightly flexible rod such as a rod made of PEEK may actually increase fusion by reducing stress shielding. Stress shielding occurs when rigid fusion constructs shield the vertebral bone in contact with the bone graft from the stresses required to form and remodel bone.

Posterior lumber stabilization (fusion and dynamic stabilization) techniques have evolved into minimally invasive approaches because such minimized exposures reduce patient morbidity and facilitate patients' recovery to function. Blood loss and hospital stays are shorter. The process of performing a minimally invasive pedicle screw fusion is the same as that for dynamic stabilization and involves two basic parts. First, screws are placed percutaneously through the pedicle into the vertebral body. For minimally invasive systems, cannulated screws are placed percutaneously over a fluoroscopically (an X-ray that can be seen on a video screen) guided guidance element. Generally, two screws are used on each vertebral body being fused, one on a right side and the other on a left side. The second part of the process involves connecting the screws with a rod and locking the rod and screws together. In dynamic stabilization, the rod or rod-like device (flexible connector) is bendable, but the process of inserting this bendable rod is the same as that for fusion. For example, a rod-like device (flexible connector), like a rod, fits within the screw heads, but may also include an element (a shock absorber, a spring, etc.) that allows some motion. The variations between different minimally invasive systems mostly arise in the method of placing the rod and locking the rod with the screws through a minimal incision.

Before the intervertebral body spacer is inserted, the damaged or degenerated disc within the disc space must be removed. In the TLIF approach, the disc space is accessed through a facetectomy in which the foramen around the nerve roots is opened with a bone-cutting tool such as an osteotome or a high speed drill. In the PLIF approach, laminectomies or laminotomies are performed to access the disc space. Both TLIF and PLIF allow for decompression of the spinal thecal sac and the nerve roots; however, the facetectomy in a TLIF allows the maximum decompression of the exiting nerve root on that side. With gentle retraction of the thecal sac, the disc space is easily accessed. Then the instruments used for clearing out the degenerated disc may be inserted into the disc space to complete the discectomy.

Following removal of the disc, the surgeon should prepare the bony surfaces, known as the end plates, of the vertebral bodies on each side of the disc that was removed. Peeling off the end plate with a tool such as a curette induces bleeding which stimulates healing and assimilation of the bone graft to be inserted into the interbody space. The spacer or cage that is to be inserted is typically constructed of bone, titanium, carbon fiber, or polymers such as PEEK. The spacer is usually hollow or at least porous to accommodate bone graft material therein. Bone inducing protein such as bone morphogenetic protein (BMP) is also commonly placed within the spacer. After placing the spacer and bone graft, the rods may be inserted into the pedicle screws and the screws can be tightened to lock the rods in place.

Typically the placement of the percutaneous screws is fairly straight forward. The insertion of the rod through the screw heads and locking of the rod with the screws are the steps that are currently most difficult through a minimal incision. In most of the minimally invasive surgery (MIS) systems used today, a guidance element, such as a wire, is placed percutaneously under fluoroscopic guidance through the pedicle. Percutaneous cannulated drills and screw taps are inserted over the guidance element/wire to prepare the tract through the pedicle and vertebral body for pedicle screw insertion. Dilating tubes and a guidance tube or a retractor system are often used to dilate and hold open the path around the guidance element through skin and muscle to reduce injury to muscle and tissue when pedicle screws and insertion tools are inserted. Pedicle screws are inserted over the guidance elements either with or without passage through a guidance tube/retractor. In order to place the rod and locking assembly into the screw heads, each screw head is associated with a tower that extends through the skin incision. The tower has to accommodate the rod and locking assemblies so it is typically larger than the maximum diameter of the screw head. Once the towers are in place, the rod is then inserted through one of a variety of methods. The leading MIS system is Sextant™ by Medtronic. In this system, the rod is placed by forming a pendulum like mechanism. The two or three towers (for one or two-level fusion, respectively) are coupled together to align the towers, and the rod is swung around through a separate incision superior or inferior to the towers in a pendulum fashion. Once the rod is swung in place, locking caps are placed through the towers and tightened. Alternatively, most of the other systems insert the rod through one of the towers and then turn the rod approximately 90° to capture the other screws in the other towers. Inserting the rod through the screw heads in a minimally invasive system is done blindly, e.g., without direct visualization of the screw head. Thus this process is sometimes tedious and frustrating.

The Sextant™ system and other systems that use towers are hindered by both the number of incisions required and the size of each incision. The use of a separate tower for each screw requires a separate incision for each tower, or a single incision long enough to accommodate two towers. The Sextant™ system also requires an additional incision for the rod, equaling six incisions (three on each side) for a single level fusion and eight incisions for a two level fusion. The other tower systems that use the direct rod insert and turn mechanism still require one incision for each screw and each incision has to be larger than the size of a tower through which the screws are inserted. Typically, each incision is at least 15 mm in length. When the sum of the lengths of all incisions on both sides are totaled, the total length of the current leading minimally invasive systems often are longer than the single midline incision of a traditional "open" approach for a single or two level pedicle screw fusion.

U.S. Pat. No. 7,306,603 entitled "Device and method for percutaneous placement of lumbar pedicle screws and connecting rods" by Frank H. Boehm, Jr., et al. and assigned to Innovative Spinal Technologies (Mansfield, Mass.), the entirety of which is hereby incorporated by reference, discloses a system of connecting a rod to the pedicle screws using a pin and recesses within the screw heads. According to this system the rod can pivot about a longitudinal axis of the pin between a first position in which the rod is parallel to the longitudinal axis of the screw (e.g., vertically oriented) and a second position in which the rod is transverse to that axis in order to bridge screws on adjacent vertebrae. The '603 patent teaches various guide systems (see FIGS. 5 and 6), rod holder systems (see FIGS. 8, 9, 10, and 11), and a rod guide system (see FIG. 12) but does not include a sleek, detachable system among them. Rather, the systems illustrated are tower-like with rather bulky dilators (80 and 86 in FIGS. 6 and 8), sheaths (81 in FIG. 6), and/or outer housing (120 in FIGS. 11 and 12).

U.S. Publication No. 2008/0140075 entitled "Press-On Pedicle Screw Assembly" by Michael D. Ensign and assigned to Alpinespine, LLC (American Fork, Utah), the entirety of which is hereby incorporated by reference, discloses attaching the rod to screw heads indirectly via a tulip assembly. The tulip assembly has a housing with an inner diameter smaller than an inner diameter of the screw head such that it is easily pressed into position upon the screw head. The rod is then placed by attaching directly to the tulip assembly after connecting the assembly to the screw head. The publication mentions using a Kirschner guidance element (or K-guidance element) for inserting both the pedicle screws and the tulip member (see [0030], [0032], and [0045]) but does not disclose how the rods are guided into position.

U.S. Publication No. 2008/0097457 entitled "Pedicle screw systems and methods of assembling/installing the same" by David R. Warnick and unassigned, the entirety of which is hereby incorporated by reference, like the '075 Publication, also discloses using a tulip assembly as an intervening means to join a rod to the screws. In this system, rather than a press-on locking mechanism, the structure is tightened by rotating an inner member and outer housing of the tulip assembly relative to one another.

U.S. Pat. No. 7,179,261 entitled "Percutaneous access devices and bone anchor assemblies" by Christopher W. Sicvol, et al. and assigned to Depuy Spine, Inc., the entirety of which is hereby incorporated by reference, describes one of the several tower systems for placement of pedicle screws percutaneously. The patent describes a situation where the angle of the screws intersect, and the towers may interfere with each other. This situation is rather typical in the lordotic lumbar spine, especially the lumbo-sacral (L5, S1) junction. In order to solve this problem, they describe cut-outs in the tubes so that two tubes can intersect. Given that the angles of the vertebrae are variable from patient to patient and the depth of the vertebrae from the skin is also highly variable, the variations on the cutouts would have to be numerous. Additionally, when two tubes intersect at the cutout as shown in FIG. 22B in the '261 patent, the edges of the cutout of one tube interferes or blocks off the lumen of the other tube, and vice versa. This occurs because the muscle and tissue surrounding the tubes will push the tubes together at the section of the cutouts thereby significantly reducing the lumen through which the rod and other elements are inserted. The only way to avoid this interference or blockage of the lumens is to keep the tubes separate which would necessitate a larger incision and would eliminate the need for cutouts in the first place.

SUMMARY

Embodiments of the present invention are directed towards improving minimally invasive (optionally adaptable for use with the percutaneous or endoscopic approach) TLIF and PLIF approaches and backing up the ALIF, DLIF, and XLIF approaches. TLIF provides several advantages including: (i) stabilization of both the anterior and posterior portions of the spine through one or more posterior incision(s); (ii) the ability to fill with bone graft material a greater volume and diversity of spaces (front disc space with the spacer, amongst the screws and rods on the sides, and in the back of vertebrae) increasing the chances of a successful stabilization through the development and solidification of bone; (iii) the spacer placed within the front disc space maintains the natural interbody disc height to reduce pressure on nerve roots (from bone spurs, thickened, ligaments, etc.); and (iv) enhanced safety because the spinal canal is accessed from one side only and this reduces the risk of pinching, stretching, or otherwise agitating the spinal nerves.

Embodiments of the invention provide a system, device and/or method (referred to herein as the Microfusion™ system) for performing a minimally invasive posterior and/or transforaminal lumbar pedicle screw fusion or stabilization procedure. Hereinafter references to "fusion" implicitly include stabilization which offers somewhat greater motion short of completely fusing the bone. Likewise, hereinafter references to "stabilization" implicitly include fusion. The main situations in which a surgeon can use the Microfusion™ system are similar to the situations in which the Sextant™ system from Medtronic is used. These situations include a minimally invasive TLIF procedure with either: (i) a micro-lumbar interbody fusion, MLIF™ or (ii) mini-open TLIF on the symptomatic side to decompress the neural compression, and a pedicle screw fusion through a minimally invasive incision on the contralateral side. Similarly the Microfusion™ system herein would be used bilaterally in a PLIF approach with the decompression and interbody spacer placement performed bilaterally. Alternatively, the Microfusion™ system is ideal for "backing up" (with a minimal posterior incision) anterior interbody fusions (ALIF) and lateral interbody fusions (XLIF™ and DLIF™) MLIF™ collectively encompasses (i) transforaminal lumbar interbody fusions and stabilizations, (ii) posterior lumbar interbody fusions and stabilizations, (iii) anterior lumbar interbody fusions and stabilizations, and (iv) lateral lumbar interbody fusions and stabilizations through a minimally invasive "micro" approach using the guidance system described herein. Since the lateral fusions are truly minimally invasive, a minimal posterior incision for pedicle screw fusion would be very complementary. Lateral interbody fusions are becoming more popular and more spine companies are coming out with their own lateral interbody fusion systems. It will be appreciated that although certain embodiments described herein are directed to minimally invasive procedures through a single skin incision, the systems and methods may also be used in open surgery or mini-open procedures through openings in the skin of a patient as desired by the practicing surgeon.

The lumbar spine has a lordotic curvature such that the lowest levels, L4, L5 and S1, have a posteriorly concave orientation or alignment, while the upper levels, L1-L3, are less lordotic. This curvature sets up a unique situation in which the trajectories through the pedicles (the trajectories to insert the pedicle screws) from L2 to S1 are not parallel. Rather, the trajectories commonly intersect at a point around the level of the skin. This configuration is similar to the spokes of a wheel in which the spokes (trajectories) meet at a common center point (a hub). Given that many patients have such a lordotic configuration of the lumbar spine, it is possible to insert pedicle screws through a single incision centered in the middle of the lumbar curvature. However, if each screw required a separate tower (or tube) (as in conventional tower/tube systems) in order for multiple screws to exist simultaneously, then the sum cross sectional area of the towers/tubes does not permit a single small incision. The towers/tubes interfere with each other and get in the way of one another due to their size.

An alternative method is necessary in order to minimize the number and size of incisions. Reducing the number and size of incisions minimizes the tissue trauma needed to place pedicle screws for lumbar stabilization or fusion. An ideal system and procedure would take full advantage of the natural curvature of the lumbar spine in order to provide this reduction. However, the apparatuses and methods of the present application described and claimed herein are not limited to applications in the lumbar vertebrae and may also find use for fusing, stabilizing, or otherwise treating vertebrae in other regions of the spine.

The number of osteoporotic spinal patients requiring surgical intervention is increasing. Historically this complex group of patients has had complications with bone-screw fixation due to the nature of the bone and types and projection geometries of the screws used, along with their methods of insertion. These complications include implant failure, screw loosening and pullout. Recent research suggests new cortical screws that project in an anteromediolateral direction have advantages over traditional screws projecting in an anteromedial direction. Embodiments of the present invention take this research into account and can be used in guiding and placing new cortical screws to project in an anteromediolateral direction in order to overcome many problems of traditional screws in osteoporotic patients. Further, embodiments of the present invention can be used to place multiple new cortical screws through a single incision, minimizing trauma to already sensitive osteoporotic patients.

One objective of certain embodiments the present invention is to provide a simple method and associated apparatus to place two or more pedicle screws through one small hole. This provides a better cosmetic and functional result with just a single skin incision of small size (approximately 0.5 to 4 cm in length, approximately 0.5 to 3 cm in length, or approximately 1 to 2 cm in length) regardless of the number of screws used. In one embodiment, the single incision is smaller than the sum of the maximum widths of two respective largest elements for each screw that is inserted through the single incision, where an element includes the screw, screw head, rod, locking assembly and associated tools.

Another objective of certain embodiments of the present invention is to be able to insert, position, and manipulate a spinal implant such as a rod and a locking assembly through the same small incision in order to lock the rod within the screws. Certain embodiments provide novel ways to insert a rod into the heads of pedicle screws and ways to lock the rod within the screws through a single small incision. The systems and methods involve in certain embodiments the attachment of one or more flexible wires, flexible yet firm extended blades or extended tabs to each pedicle screw head to be used to guide the rod down to the screw. By using flexible and strong guidance (or guide) elements that do not completely enclose the guided element, the towers/tubes currently used with each screw are not needed. The guide elements are configured so that they can overlap or intersect at or below the skin incision, thereby enabling the use of a small, single skin incision. The screws, rods, and locking assemblies can all be placed through a single small incision and yet still be appropriately interconnected within because of the natural lordotic curvature of the lumbar spine. By attaching at least one guidance element on each side of the screw head, the guidance elements assist to align the screw head. The guidance elements also trap or restrict displacement of the rod, forcing it to fit between them and directly into the screw head.

Compared to U.S. Pat. No. 7,179,261 to Sicvol described above, embodiments of the present invention eliminate the need for "cut-outs" where the guide elements intersect. For example, in embodiments utilizing extended tabs or blades, these extended tabs or blades do not have a proximal, distal, or any lumen, and the configuration of guidance elements (extended tabs or blades) for screws at adjacent levels allow the tabs to intersect and overlap completely for any patient with any relative geometries. Thus interference between adjacent guidance elements on adjacent vertebrae is not a problem. Also, in the cut-out tubes taught by the '261 patent, a rod or other element would still have to be inserted through the tube at some point. The cut-out tubes require that the rod (or other inserted element) is oriented longitudinally parallel to the long axis of the tube as it is directed into the body until it reaches a section with side wall openings or slots distal to the cut-out section, at which point it may optionally be turned perpendicularly to the long axis and directed out of the side wall through the opening or slot. In embodiments of the present invention by using guidance elements such as extended blades or extended tabs (from the screw head), the element that is guided by them and inserted along them (e.g., a rod, a locking assembly etc.) does not have to be inserted through any lumen. When a rod is inserted using the blades, the blades can simply be fed through the outer edges of the rod body, through a retaining element or clasp attached to the rod body, or between the outer edges of the rod body and a retaining element (retention thread). Thus, it is possible for the inserted rod or other elements to be oriented perpendicular to the long axis or oriented in any other manner or at any angle during the entire entry pathway. This provides greater flexibility for avoiding interference between adjacent stabilization system pieces and eliminates the need for a surgeon to identify the cut-out sections before turning the screw/rod perpendicularly and/or reorienting it. Furthermore, since there are no lumens proximally or distally with the extended tabs, blades from adjacent levels may overlap and intersect without the need for cutout therefore allowing all blades to exit a single small minimal incision.

The guidance elements can also be used to guide the locking assemblies down to the screw heads for embodiments in which the locking assembly is not part of the screw head itself (and already down there). In such embodiments, guidance is not needed for the locking assembly because it is built into or part of the screw head. Examples of this latter situation are a hinged door over the rod that swings and snaps into position to hold the rod in place in the screw head. In this situation the built-in locking assembly (on the screw head) is inserted into the pedicle contemporaneously with the screw.

In an embodiment, the locking assembly is also guided down to the screw by small loops placed on the sides of the insertion tools or small holes or slots made in the sides of the insertion tools. The guidance elements (e.g., wires, extended blades or extended tabs) pass through these loops/holes (the loops pass over the guidance elements) to guide the insertion tools down to the screws to deposit (e.g., drop off or detach) the rods and locking means. In another embodiment, the locking assembly is guided down to the screw by a notched lock and glide mechanism between the locking assembly and the guidance element such as extended blades or tabs. The notched groove on the extended blades traps the locking mechanism into position allowing it to only slide down the blade to fit perfectly into the screw head. Due to the flexibility of the guidance elements, coupled with their ability to possess a high strength while occupying a small volume, several of them can coexist simultaneously even in a small incision. Furthermore, guidance elements that are less flexible or made of rigid or semi-rigid materials such as blades or extended tabs can be offset from one pedicle screw to the other. This offset advantageously allows the blades to intersect and crisscross while still allowing the rod and locking mechanism to be placed.

According to one embodiment, the locking assembly is part of the screw head itself and is therefore deposited when the screw is placed, before the rod arrives, rather than requiring separate guidance and being placed after the rod. For example, the locking assembly (i) may involve turning the screw head to trap the rod and/or (ii) may include elements that snap into place to trap the rod and/or (iii) may include a carved out channel for the rod in the body of the screw head that restricts its motion. According to these embodiments, respectively, the rod may be unlocked, provisionally locked (restrained), or securely locked depending upon (i) the extent or angle of rotation of the screw head about an axis, (ii) the length of extension or extent of flexion for protruding elements that snap into place, and (iii) the position of the rod inside grooves of the screw head. The screw head also might have retaining elements including bars, barbs, teeth, balls, etc. that protrude upon activation to trap the rod (or other elements inserted into the screw head) by covering a top surface of the rod and/or mating with the rod's peripheral edges to enclose upon it and stabilize it through friction or physical pressure. This embodiment encompasses modern capless locking assemblies and those without set screws.

Another embodiment is a hybrid system where each screw is placed through short towers or tubes that do not come to the skin surface. Wires, blade or tab extensions are attached to the top of the towers or tubes so that the screw, rod, locking assembly, and tools used for insertion, adjustment, locking, compression, distraction, and removal are guided by the extensions close to the skin but through individual towers or tubes close to the bone and pedicle screw. This hybrid system offers both the advantages of the wires/extended blades/tabs in which many guidance elements can overlap in a single incision at the skin level and the advantages of a tower or tube system are preserved at the bone level. Some surgeons who are comfortable with the tower system but who want the advantages of the blade/tab system may want to use this hybrid system.

In one embodiment, the towers, tubes, blades, arms, or other upwardly directed extended guidance elements may comprise adjustable height guiding elements, such as telescoping or telescopic guiding elements. In some embodiments, the telescoping guiding elements are advantageously connected to wires or other upwardly directed extension elements (blades, tabs, etc.) that permit the guiding elements to be telescoped to a smaller height and for example be positioned entirely below the skin incision. The wires or other upwardly directed extension elements advantageously maintain connection with the telescoping elements to control and or retrieve the telescoping elements. Two or more sets of telescopic guiding elements attached to respective screwed can create offset, intersecting paths during a minimally invasive surgery to guide implants or tools. The telescoping towers, tubes, blades, arms, or extended tabs get out of the way of other towers, tubes, blades, arms, or tabs by adjusting the height of the telescoping guiding elements. Pieces of the towers, tubes, blades, arms, or extended tabs can be slid out of the wound as long as they are guided by extension wires or string.

Making some of the guidance elements telescopic allows for more guidance elements to fit through a single incision smoothly, thereby advantageously reducing the need to have a larger incision and/or multiple incisions. After insertion, the various guidance elements may be deployed telescopically as needed. Using telescoping components as part of the upwardly directed extended guidance elements allows a rod for stabilizing vertebrae to be inserted into the body through the telescoping components and through the same singular incision, minimizing invasiveness of the procedure.

A number of other embodiments may achieve the same desired effect as telescoping the height of each tube. For multiple tubes to be placed through a single incision, all of the tubes except or even including the one extending through the incision may be shortened. Thus, in one embodiment the height may be adjusted either by telescoping or by shortening the tube, blade or other component. The shortening process can alternatively occur by cutting material amenable to cutting such as plastic or metal. Additionally some material could be cut by melting or cauterizing. Another embodiment is merely bending a flexible part of the guidance element away from the path of the other screws and towers, such as described in U.S. Pat. No. 7,846,093, U.S. Publication No. 2008/0262318 A1 and U.S. Publication No. 2009/0222044 A1, the entirety of each of which is hereby incorporated by reference. In some embodiments, guidance elements can have a multitude of flexible consistencies such that the guidance elements are more firm or rigid through the muscle and fascia which places a significant force upon the guidance element. Above the fascia, the forces are lessened due to the preponderance of fatty subcutaneous tissue. Thus in the region of the subcutaneous tissue and skin, it is beneficial to have more flexible components that can also bend out of the way of other trajectories for screws. The greater flexibility at the skin level also provides less pressure on the skin and will lead to less damage to the skin which is beneficial for healing.

The height of the guidance elements can also be adjusted by snapping off portions at pre-scored intervals along the elements. Extended tab screws may be pre-scored to break off or snap off after the rod has been locked into the screw head. A guidance element that has been pre-scored in a similar fashion at 1-5 mm intervals along the entire extended tab or tube would allow the height of the blade or tube to be customized for each patient. Alternatively, the guidance elements could be comprised of a multitude of sub-units that lock together to make one guidance elements. More complex and sturdy locking mechanisms could easily be envisioned and are within the scope of the current invention. The height of guidance elements can also be adjusted by an accordion type mechanism. Similarly Chinese lanterns and mini-blinds also demonstrate everyday examples of mechanisms in which the height can be adjusted. A coiled flexible guidance element configured in a spiral or spring shape can also allow adjustment in height by stretching or collapsing the spring. Furthermore, such a spring mechanism allows other items such as screws to be placed through the spring by spreading the coils of the spring at the skin incision to allow the other screws, rods, locking mechanisms, etc. to be placed through the spring mechanism.

All combinations and arrangements of towers, tubes, blades, arms, tabs, wires, and other upwardly directed extended guidance elements, either as described herein or in hybrid systems which combine conventional tower/guidance elements as described in the prior art (such as described in the references incorporated by reference throughout this specification) are contemplated as within the spirit and scope of the present invention. As used herein, the term guiding or guidance element is intended to include one or more components extending between a screw and a skin incision, preferably directly or indirectly coupled or detachably connected to a screw head, and includes both conventional towers or tubes such as those made of rigid or semi-rigid materials as described in the patents and publications incorporated by reference throughout this specification, as well as the additional embodiments of guiding or guidance elements as described herein. The most suitable selection and arrangement is for the surgeon to determine in each particular case. For example, in one embodiment, there may be telescoping tubes at one level, wires at the next level, and blades at the next level on one side (of the slot for the rod) with blades attached to wires on the other side (of the slot for the rod). Different variations may be selected for each side (medial, lateral) in order to introduce more components through the same incision. The goal is to provide enough guidance elements to properly guide the stabilization rods, locking assemblies, tools, etc. to the pedicle while minimizing the number of incisions and preventing overcrowding. Eliminating overcrowding permits proper visualization so that the surgeon can work comfortably and efficiently.

A further objective of embodiments of the present invention is to reduce patient discomfort and the potential for iatrogenic injury. Providing a system and method designed for use through a single incision assists this purpose. Only one quality incision need be made. With every incision that is made there is at least a small risk of inadvertent injury, including nerve damage, even by a skilled surgeon. However, incising is not the only risky stage of the procedure, nor the only stage capable of causing patient trauma yet having the potential for improvement to reduce these risks and liabilities. Another step of the procedure commonly causing post-surgical patient discomfort and diminished motor/sensory function is placement of the rods within the screws. The extended blades/tabs not only guide the rods to the screws but also function to hold nerves and muscles out of the screw head for easier insertion of the rods and locking assemblies. With nerves and muscles restrained from entering the trajectories along which the rods are delivered, there is a reduced risk of pinching, tearing, or severing a nerve or muscle.

While most minimally invasive pedicle screw systems are designed with parallel trajectories for the placement of pedicle screws and their associated towers, embodiments of the present invention allow for the possibility of intersection and near complete overlap of the paths of the screws and guidance elements. These embodiments permit the widest flexibility in overlap, intersection and spatial configuration of the paths of the screws and guidance elements. The smallest skin incision occurs when the maximal amount of overlap or intersection occurs at the skin incision. The flexibility of these systems is exhibited by the full spectrum of permissible embodiments. In certain embodiments, the upwardly directed guide elements (such as guide wires or guide shafts) associated with each of two or more screws extend upward from their respective screw heads through one or more skin incisions to form, as idealized lines or cylinders in space, a configuration selected from the group consisting of:

(i) parallel configuration of the guide elements associated with different screws;
(ii) skew configuration where the guide elements associated with different screws are neither parallel or intersecting;
(iii) converging but not intersecting configuration;
(iv) intersecting at an inverted "V"-configuration where the proximal ends intersect outside, at, or below a surface of skin and at an angle between 0 and 180 degrees;
(v) intersecting at a "T" or an inverted "Y" configuration where a proximal end of the guide element(s) from one screw intersects the guide element(s) from another screw(s) at a point other than at an end of the guide element(s) and at an angle between 0 and 180 degrees, where the intersection point is outside, at, or below a surface of skin;
(vi) intersecting at an "X"-configuration or a criss-cross configuration where guide elements of two or more screws intersect at points not at the ends of the guidance elements and at an angle between 0 and 180 degrees, where the intersection point is outside, at, or below a surface of skin; and
(vii) diverging configuration where the proximal ends outside the skin are farther apart than the distal ends at the screw head.

In some embodiments, a system is provided for performing spine stabilization through an opening in skin of a patient. The opening may in one embodiment be a single, minimally invasive skin incision. The system comprises a first screw having a screw head and a first guiding element comprising adjustable height component detachably connected to the first screw, the first screw being configured for implantation in a first vertebra. The system also comprises a second screw having a screw head and a second guiding element detachably connected to the second screw, the second screw configured for implantation in a second vertebra. The first screw with the first guiding element and the second screw with the second guiding element can be delivered into the first and second vertebra. The adjustable height component of the first guiding element can be adjustable to reduce a height of the first guiding element at or below a level of the skin when the first screw is implanted in the first vertebra to allow the second guiding element to extend through the skin opening when the second screw is implanted in the second vertebra. In some embodiments, the adjustable height component comprises telescoping components, and can assume the form of a plurality of cylindrical members and/or a plurality of blades.

In some embodiments, a system is provided for performing spine stabilization through an opening in skin of a patient. The system comprises a first screw having a screw head configured to be implanted in a first vertebra and a second screw having a screw head configured to be implanted in a second vertebra. The system comprises at least one or both of: (i) a first guiding element detachably connected to the first screw configured to have a height at or below a level of the skin opening when the second screw is implanted in the second vertebra, and (ii) one or more flexible wire(s) configured to extend upwardly from the first screw and/or from the first guiding element and through the skin opening when the second screw is implanted in the second vertebra. The system further comprises a second guiding element detachably connected to the second screw, the second guiding element comprising a rigid or semi-rigid material configured to extend through and above the skin opening when the second screw is implanted in the second vertebra. A spinal implant member is connectable between the first screw and the second screw. Either one or both of the first and second guiding elements can comprise a tube or blades. In addition, either one or both of the first and second guiding elements can comprise telescoping components.

In some embodiments, a system is provided for performing spine stabilization. The system comprises a first screw having a first screw head and a second screw having a second screw head. A spinal implant, which may be a rod or a flexible connector, is configured to be coupled to both the first screw head and the second screw head. A first means for guiding the spinal implant and/or instruments to the first screw is directly or indirectly connected to the first screw. A second means for guiding the spinal implant and/or instruments to the second screw is directly or indirectly connected to the second screw. At least one of the first and second means for guiding comprises means for permitting the first screw, second screw and spinal implant to be delivered into a patient through a single, minimally invasive skin incision. In one embodiment, the minimally invasive skin incision is between 0.5 cm and 4 cm, more preferably 3 cm or less or 2 cm or less.

In some embodiments, a method of treating the spine is provided. The method comprises making an incision in the skin of a patient to provide access to a spinal location; delivering a first screw through the incision and into a first vertebra and second screw through the same incision and into a second vertebra, wherein at least one of the first screw and second screw has detachably connected thereto an adjustable height guiding element extending upwardly through the incision; delivering a rod or flexible connector to the screws; and locking the rod or flexible connector to each of the screws. In some embodiments, wherein both the first screw and the second screw having detachably connected thereto a first plurality of telescoping guiding elements and a second plurality of telescoping guiding elements, respectively, the method further comprises delivering the first screw through the incision and into the first vertebra with the first plurality of telescoping guiding elements extending through the incision; reducing a height of the first plurality of telescoping guiding elements so that an uppermost one of the telescoping guiding elements is positioned below the incision; and delivering the second screw through the same incision into the second vertebra with the second plurality of telescoping guiding elements extending through the incision.

In some embodiments, a method of treating the spine is provided. The method comprises making an incision in the skin of a patient to provide access to a spinal location; delivering a first screw through the incision and into a first vertebra, wherein the first screw, after implantation, has at least one or both of: (i) a flexible wire extending upwardly from the first screw and through the incision, and (ii) a first guiding element detachably connected to the first screw with a height at or below a level of the skin incision; delivering a second screw through the same incision and into a second vertebra, wherein the second screw has detachably connected thereto a second guiding element comprising a rigid or semi-rigid material extending through and above the skin incision when the second screw is implanted in the second vertebra; delivering a rod or flexible connector to the screws; and locking the rod or flexible connector to each of the screws.

Other objectives and advantages of embodiments of the invention will be set forth in the description which follows. Implicit modifications of the present invention based on the explicit descriptions will be, at least in part, obvious from the description, or may be learned by practice of the invention. Such subtle, predictable modifications and adaptations are taken to be within the scope of the present invention. Additional advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 shows an embodiment of guidance elements as offset extended blades/tabs attached to screw heads with the extended blades attached to the outside of one screw head and the inside of another screw head.

FIG. 2A is a side view and FIG. 2B is a head-on perspective view.

FIGS. 10A-10C show an embodiment for the screw cap locking assembly in which there is a concentric outer screw holder, threaded on the outside to engage with corresponding threads on the inside of the extended guide blades, and also threaded on the inside so that the inner screw can be advanced past the holder, further into the screw seat, upon proper positioning over the screw head.

FIGS. 11A-11C show a pedicle screw with a tapered shaft directed downwards and with a concave U-shaped screw head and detachable elongated guidance elements directed upwards (one on each side of the head). The elongated guidance elements may attach directly to the screw head (left image) or they may attach to 2 or more short guidance elements on each side of the screw head. This configuration creates a guidance element cage that forces the screw head and the rod to align with each other as the rod is lowered into the seat of the screw head.

FIGS. 19A-19F show an embodiment in which two guidance elements are attached to the top of the screw head, one on each side. Three orientations (left to right) show the process of lowering the rod into the screw head guided by the guidance elements (FIGS. 19A-19C) along with the final position in which the rod is completely within the screw head (FIGS. 19D-19F).

FIGS. 20A-20C show a locking assembly being lowered to attach to the screw head to secure the rod within. An instrument used to lock a locking assembly onto the screw head can also guided by the guidance element but is not shown in this diagram.

FIGS. 21A-21F show another embodiment in which the guidance elements are connected to flexible strands. The strands are then connected to the top of the screw shaft or the base of the screw head. As the rod is lowered into the screw head, guided by the guidance elements, the flexible strands wrap around the rod. Each strand is just long enough (approximately half of the circumference of the rod) to wrap around the rod so that the ends of the guidance elements meet together above the rod.

FIGS. 23A-23C show the insertion of a longer rod through 4 sets of guidance elements attached to 4 pedicle screws in a three level stabilization. The left image shows the guidance elements in a neutral, straight position. The middle and right images show the guidance elements of the two superior vertebrae (L3 and L4) splayed open so that the rod can be easily tunneled in between the guidance elements.

FIGS. 25A-25C show embodiments of inserting a rod through guidance elements that do not share an incision with the rod. Here the lowest two levels (L5 and S1) do share a single incision but the upper two levels (L3 and L4) have separate incisions. Rod retention threads only span the inferior half of the rod and only capture the guidance elements of the lower two vertebrae (L5 and S1). The superior end of the rod is then pushed through the guidance elements of the upper two vertebrae (middle figure). Or, a thread that is attached to the superior end of the rod can be used to pull the rod through the guidance elements of the upper two vertebrae. This thread can be introduced in between each set of guidance elements by a large suture needle that is inserted in one incision and is pulled out of the next incision in between the guidance elements.

FIGS. 26A-26D show an embodiment of flanged attachments that help the rod to find the proper orientation to best fit into the screw head. As shown, each attachment is preferably convex in a direction towards the rod so that as the rod approaches the screw head, the entrance to the screw head can accept a large range of angles in which the rod is oriented and still receive the rod, gradually improving the rod's orientation as it gets closer to the seat of the screw head.

FIGS. 27A and 27B show two sequences of lowering a rod into a malaligned screw head (or, of lowering a malaligned rod into a properly aligned screw head) using flanged attachments. The bi-convex nature of the flanged attachments permits the rod to twist and adjust as it is lowered. Otherwise, without the flanged attachments, in a malaligned situation the rod would hit the edges of the screw head and would not be able to be lowered further. The flanged attachments are shown here as detachable elements on the screw head; however, another preferred embodiment is a flanged and convex shaped rod guide built into the tops of opposing sides of the "U" shaped screw head (e.g., may be integrally part of the screw head interior itself).

FIGS. 29A-29C show another embodiment in which a guidance element is connected to a clamp or device that holds the screw head. An embodiment of the clamp or device is composed of at least two parts that can be broken apart after the rod is locked in place so that the pieces of the device can be removed with the guidance element. The clamp or device is attached to the screw before insertion into the bone. The clamp or device is shaped so not to impede the placement of the rod into the seat of the screw head. The parts of the clamp are held together by a thin strand that is cut or snapped apart after the rod is locked in place. The clamp or device is made from metal, polymer, or plastic materials such that no residual is left after the clamp is removed.

FIGS. 34A-34D show another embodiment of telescoping guiding elements, this time with telescoping guiding arms configured with an indentation that creates a groove or channel along the length thereof to receive a protruding portion of a locking assembly or other element, in order to guide the locking assembly down to the base of the arms, just above the rod.

FIG. 35B shows how a portion of the blades that crosses the skin incision can be slid off of flexible wires, allowing the second screw to be inserted through the incision with minimal interference. Once the second screw and the second guidance elements are in place, the blades of the first guidance element can be slid back down the wires into its original position.

FIGS. 37A-37D compare drilled hole volumes and relative positions for pedicle screws implanted along a traditional trajectory and according to a new cortical screw trajectory method. (Figures taken from B. G. Santoni, et al (2009) Cortical Bone Trajectory for Lumbar Pedicle Screws. The Spine Journal 9:p 366-373, the entirety of which is hereby incorporated by reference).

FIGS. 40A-40D show different views of the telescoping guiding element with the half-cylinder portion lowered to reduce the height of the guiding element. FIG. 40A (left) is the same configuration as FIG. 39 with the telescoping extension on the outside of the bottom tube. FIG. 40B shows the telescoping extension on the inside of the bottom tube. The half-cylinder extension on the inside has a smaller diameter than the extension in FIG. 40A. This size difference is helpful when the blades intermesh when intersecting at a small incision. FIG. 40C shows that the top of the telescoping extension can be smaller than a half-cylinder, while FIG. 40D shows that the top of the telescoping extension can be larger than half-cylinder.

FIG. 45 shows the pair of telescoping guiding elements of FIG. 43 positioned on first and second vertebrae.

FIGS. 46A-46D show embodiments of guiding elements having expandable blades or tabs.

DETAILED DESCRIPTION OF THE EMBODIMENTS

Figure 2B:
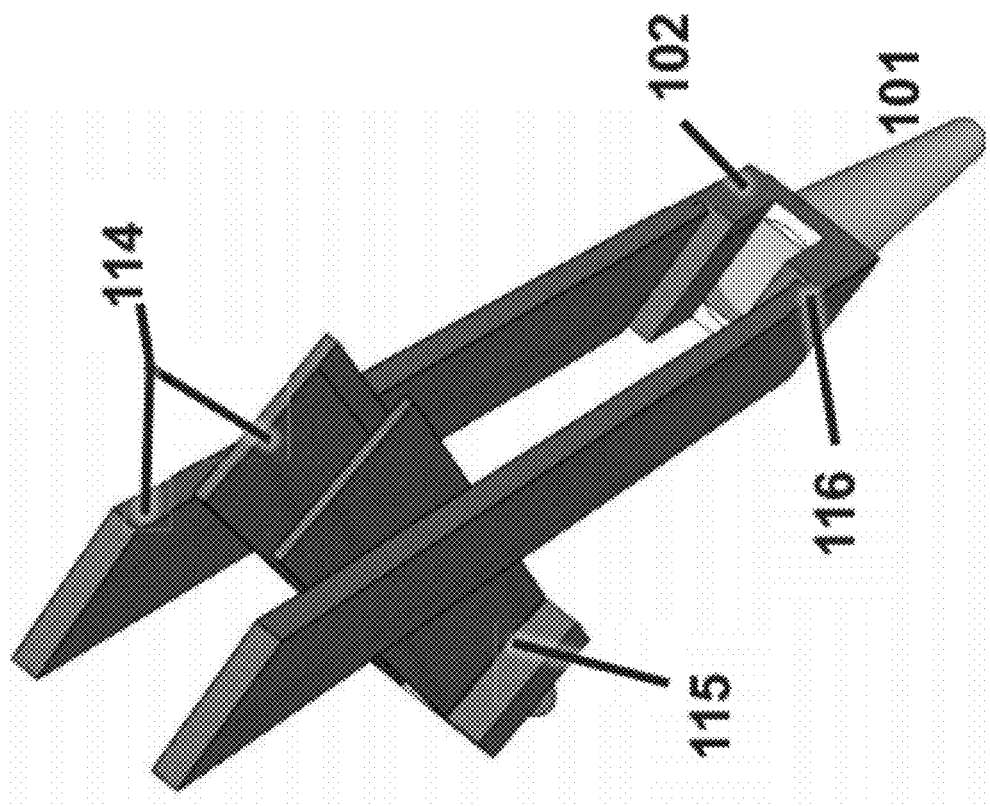
FIGS. 2A and 2B show how the offset extended blades/tabs function in operation to intersect/cross without interference as the blades/tabs extending from one screw head pass inside/outside the blades/tabs extending from another adjacent screw head such that the two could pass through the same incision.

Embodiments of the invention involve improved systems, apparatuses and methods for guiding one or more screws, rods, and locking assemblies down to the vertebrae and for securing the rod to stabilize the vertebrae. Screws may include pedicle screws as shown in the figures and as described in the patents and publications incorporated by reference herein, and with reference to FIG. 1 may include a threaded bone engaging shaft 101 and a screw head 102. The threaded shaft 101 may be relatively moveable to different angles relative to the screw head 102. For example, a proximal end of the threaded shaft may include a spherical or semi-spherical head that engages a similarly-shaped seat in a lower portion of the screw head 102. The screw head 102 has generally a U-shape, as shown in FIG. 1, defining upwardly extending arms that form a channel for receiving a rod 104. The rod may either sit on the head of the threaded shaft 101, or may sit on an insert placed in the screw head 102 for receiving the rod 104.

A locking assembly may be built into or attached onto the screw head or be a separate element. Locking assemblies that are separate elements include (but are not limited to) those reliant on caps and set screws. Locking assemblies integrated with the screw head include (but are not limited to) rotatable mechanisms in which a turn of the screw head traps the rod. The locking assembly may be guided down to the screw before or after insertion of the rod depending upon the details of the locking mechanism used to secure the rod. In some cases, the locking assembly is already present on the screw head before the rod is received. In other cases the rod is inserted into the screw head first and the locking assembly follows. In one example, the upwardly extending arms of the screw head 102 may be internally threaded to receive an externally threaded cap screw that is rotated into the screw head 102 to apply a downward force to a rod 104 sitting in the channel of the screw head. This downward force may also then lock the position of the screw head 102 relative to the shaft 104.

The guidance elements for directing the rod, various locking assembly components (e.g., screw head caps), surgical insertion and manipulation tools, and other components into position may be any type of upwardly directed, extended guidance elements. These guidance elements are preferably detachably connected to the screw heads or screws so that they can be easily removed once a procedure is completed. Suitable guidance elements include: tubes, towers, blades, arms, extended tabs, wires, string, etc. As used herein, extended blades refers to separate elements that attach to the screw head or tabs on the screw head, whereas extended tabs refers to elements that are integrally connected with tabs on the screw head or even the screw itself. The extended tabs or extended blades run from a site adjacent the screw head up through the incision site. They can be curved (along one or more axis) or bent (along one or more axis) to accommodate the cap and other components. The guidance elements may also be curved or bent in order to be offset from adjacent elements such that they do not interfere if and when they cross. The curvature may be a permanent rounded shape or they may be flexibly curveable or comprised of foldable panels (see FIG. 3A). The curves and bends may be permanent and pre-formed or adjustable in situ. The extended guidance elements may also be tapered, threaded and/or notched to assist in stabilizing the cap or other components as they are lowered down to the screw head.

In some embodiments, the guidance elements comprise two or more blades that may be offset from each other so that they do not interfere if and when they cross. They can be offset in any functional manner, and can assume different positions around the screw heads (e.g., for staggered crossing), bending at different positions (e.g., straight to bent), curvatures that are non-intersecting with adjacent elements (blades from adjacent screw head), etc.

The extended tabs/blades or other guidance elements on adjacent screws may be offset such that they do not interfere with one another when they intersect. Rather, as they cross one another, the extended tabs/blades (or other guidance elements) smoothly pass by one another. Therefore the extended tabs/blades on adjacent screws can be inserted through the same small incision and manipulated within that incision. This may be achieved by tabs/blades, or other guidance elements, on the inside of one screw and the outside of the other screw. Or, in another manner the tabs/blades for adjacent screws can simply be staggered or misaligned. Another option is for one screw to have a single tab/blade on the medial side while another screw has a single tab/blade on the lateral side. Still another option is for one screw to have extended tabs, while one or more other screws have flexible wire or wires as guidance elements.

In some embodiments, some of the extended guidance elements (tabs, blades, etc.) on some screw heads may be straight while those on others are bendable or angled, such that the bendable or angled elements cross over the straight ones to exit the body through the same skin level incision. In other embodiments, a first screw is connected to a first extended guidance element in the form of a plurality of blades and a second screw is connected to a second extended guidance element in the form of a plurality of blades. The plurality of blades of the first extended guidance element can overlap and/or intersect with the plurality of blades of the second extended guidance element. Advantageously the first extended guidance element and the second extended guidance element can intersect or overlap at or near a skin level incision. By intersecting or overlapping at or near a skin level incision, this allows both of the guidance elements to extend through a single, small incision.

The extended tabs/blades or other guidance elements are configured to easily detach from the screw head upon completion of directing rods, caps, instruments, and other components precisely to the screw head. This detachment process may occur by any number of means, including break-off along a pre-perforated or notched line, burning or melting at the base of the tabs/blades with an instrument, releasing a mechanical clamp, etc. The extended guidance elements (e.g. extended tabs, extended blades, etc.) for adjacent screws may all be attached to their respective screw heads at different positions along the screw head to produce the offset configuration. Or, they may all be attached to their respective screw heads at the same location and bent at different angles to form different configurations that are offset with respect to one another when crossed. That is, the extended guidance elements may be bent to come out of the screw head at different lateral displacements such that they do not interfere with one another. For a two level fusion, three offset extended guidance elements (tabs, blades, etc.) attached to three adjacent screws is appropriate. For a three level fusion, there would be four offset extended guidance elements attached to four adjacent screws. A four level fusion with five offset extended guidance elements attached to five adjacent screws, potentially all coming through the same skin level incision and crossing at some point at or near the same level skin incision, may also be possible in some situations.

According to one embodiment the extended tabs/blades/arms and wires can work together in a "hybrid" concept. The first tab attached to the screw head is easily detachable. Additional tabs between the screw head and distal wires protruding from the skin can be added and removed as needed to lengthen or shorten the distance of the guidance trajectory. One embodiment has a multitude of breakoff tabs attached to one another in series, creating a long extended blade. The blade can then be tailored to the appropriate length, such as at the level of the skin incision, by breaking the tabs off at the closest breakoff point to that point. In some embodiments, one or more of the breakoff tabs can be attached to a proximal wire to keep track of and locate the tab within the patient. As used herein, distal is defined as a space farther from a particular location, and proximal is defined as a space closer to the particular location. In some embodiments, a portion of a tab or blade that extends out beyond an incision can be considered a proximal portion, while a portion of a tab or blade that is beneath the incision can be considered a distal portion.

The flexible guidance wires can be used to direct the add-on tab elements during insertion and removal. The guidance wires can serve as a guide to direct add-on tab elements into place within the patient. Alternatively, the guidance wires can be attached to an assembly of one or more telescoping members (as discussed below) and can be used to adjust the height of the assembly. In other embodiments, a plurality of flexible guidance wires can serve alone as guidance elements to guide rods, tools or locking assembly components to a desired location at or near the spine. In yet other embodiments, the flexible guidance wires can be part of a "hybrid" concept and can work in conjunction with tabs/blades/arms to guide elements to a desired location. The rods, tools or locking assembly components can be delivered via the guidance elements by hand, or in some embodiments, using a stereotactic guidance mechanism and/or by a robot. In fact, the minimally invasive system of embodiments of the present invention is ideally suited to work with robotic surgery and stereotactically guided surgery where the trajectories of spine fixation screws and the screws themselves are all directed and performed through robotic and stereotactic assistance.

In some embodiments, the upwardly directed guidance elements or portions thereof may be telescopic such that one element may be pulled out of or passed over another element. Advantageously, this telescoping characteristic can be used to accommodate a greater number of guidance elements or portions thereof through a single incision. Telescoping tubes are also helpful for guiding a rod through the center of the tubes and thereby inserting the rod through the same common single incision as the guidance elements.

In one hybrid embodiment, there is a short blade extending upwardly from one side of the screw head and a longer blade extendingly upwardly from the other side of the screw head. The next level has the short blade and the longer blade each on the opposite side (see FIGS. 36A-36C). In another embodiment, short tubes may extend from the screw head, with upwardly extending blades that telescope to adjust the height of the guidance element (see FIG. 39).

In another embodiment, instead of telescoping guiding elements, some of the guidance elements or portions thereof may be removable in order to make room for other elements. After all the elements have been inserted the top portions of the elements may be placed into their final positions. Multiple elements or portions thereof may be inserted through a single incision separately or one piece at a time in order to prevent overcrowding near skin level.

In embodiments in which a wire or string that passes beyond the incision at the skin level is attached to another guidance element, such as an extended tab, the wire or string serves the purpose of making sure that the extended tab does not get lost in the wound after it is detached or broken off. In this manner, wire or string can advantageously be used to pull an extended tab or other guidance element out of the wound.

In some embodiments, hinges may exist at the base or along the body of an extended guidance element, proximal or distal to the point at which the guidance element attaches to the screw head. Hinges would permit the guidance element to open up, as necessary, to receive the rod, an instrument, or another component. The hinges may be on either side of the point at which the extended guidance elements join the screw head: the proximal screw head side or the distal extended guidance element side. If the hinges are on the proximal screw head side they will remain after the extended guidance elements are detached. If the hinges are on the distal extended guidance element side they will be removed with the guidance elements. In situations where the guidance elements attach to the screw head through a mechanical mechanism the hinge might be integrated into the mechanical mechanism such that detaching the extended guidance elements after they have performed their role disassembles the hinge.

FIG. 1 shows an embodiment in which the guidance elements 114 are extended blades or extended tabs that connect with the screw head 102 anywhere along it from the inside perimeter/inside wall 115 to the outside perimeter/outside wall 116. In some embodiments, the extended blades/tabs 114 can advantageously provide more stability than wires and more flexibility than towers that encompass the rods or other guided elements. Furthermore, extended blades/tabs 114 and 116 can be attached to extensions on the screw head or be bent outwards so that the blades/tabs are positioned beyond the edge of the screw head. In this embodiment, an entire second screw with accompanying screw head and guidance elements can fit completely within the widened space between the blades/tabs that are displaced outside the edges of the screw head on the first screw, without bending or widening the proximal ends of the blades/tabs.

As illustrated in FIG. 1, a system for delivering a rod through an incision to a desired location in a patient can include a first screw having a screw head 102 with a pair of extended blades or tabs connected to an inside wall perimeter 115 of the screw head 102, and a second screw having a screw head 102 with a pair of extended blades or tabs connected to an outside wall perimeter 116 of the screw head 102. Advantageously, each of the pair of blades form a different sized passageway or channel through which an implant (e.g, a rod member) or guide tool can be delivered, with the pair of blades attached to the first screw head creating a narrower passageway than the pair of blades attached to the second screw head. Moreover, the system is configured such that the blades or tabs in an inside wall perimeter 115 attached to the first screw can advantageously criss-cross or intersect with the blades or tabs on the outside wall perimeter 116 of the second screw (as shown in FIG. 2A). The criss-crossing of the pair of blades of the first screw and the pair of blades of the second screw can occur at a single incision of small size, or near the single incision of small size.

In some embodiments, the system is configured such that when the pair of blades attached to an inner wall perimeter 115 of the first screw head are criss-crossed at or near a single small incision with the pair of blades attached to an outside wall perimeter 116 of the second screw head, an implant such as a rod member can be guided down the narrower passageway created by the pair of blades connected to the first screw head. The rod member can be guided such that one end of the rod is seated in a seat of the first screw head. The other end of the rod member can pass through the passageway created by the pair of blades connected to the second screw head and can be seated in the seat of second screw head. While other conventional systems allow for rod placement across two screw heads, the present system using criss-crossing blades at or near a small incision allows for a smaller, less minimally invasive incision in order to achieve the desired result. The criss-crossing blades thus reduce the amount of trauma to the patient and reduce the amount of time required for healing.

Figure 2A:
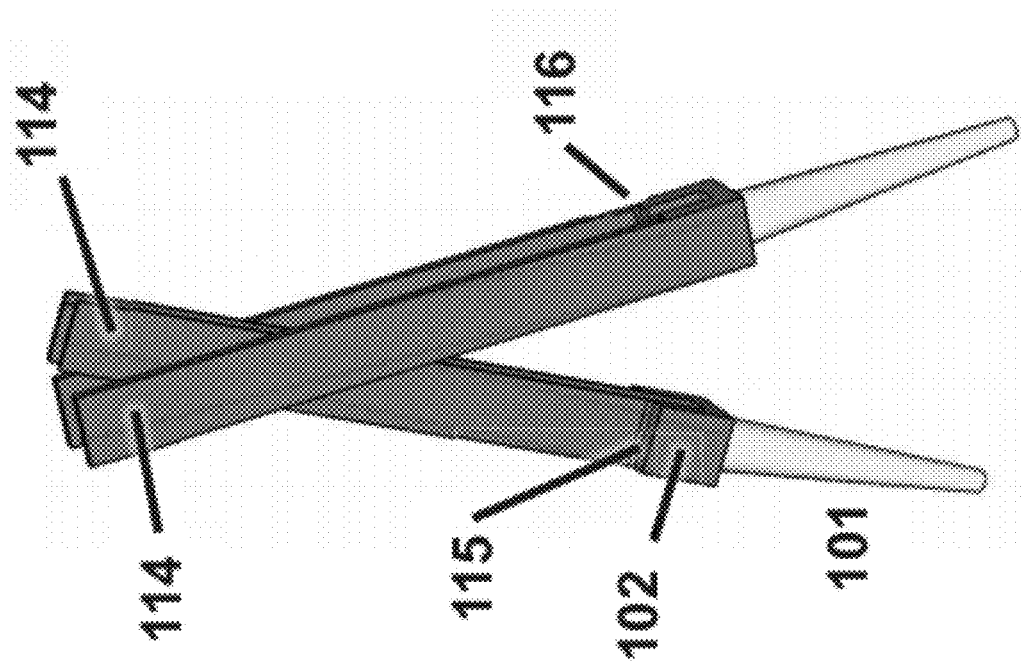

FIGS. 2A and 2B show how the extended blades/tabs 114 are offset 115/116 such that in operation upon intersection (shown in both FIG. 2A from the side and in FIG. 2B head-on) they smoothly pass one another without interference. As such, adjacent extended blades/tabs 114 can pass through the same skin level incision and be manipulated easily through a range of geometries for final positioning. Further, the same devices can be used generally on all patients with different anatomical dimensions.

Figure 3B:
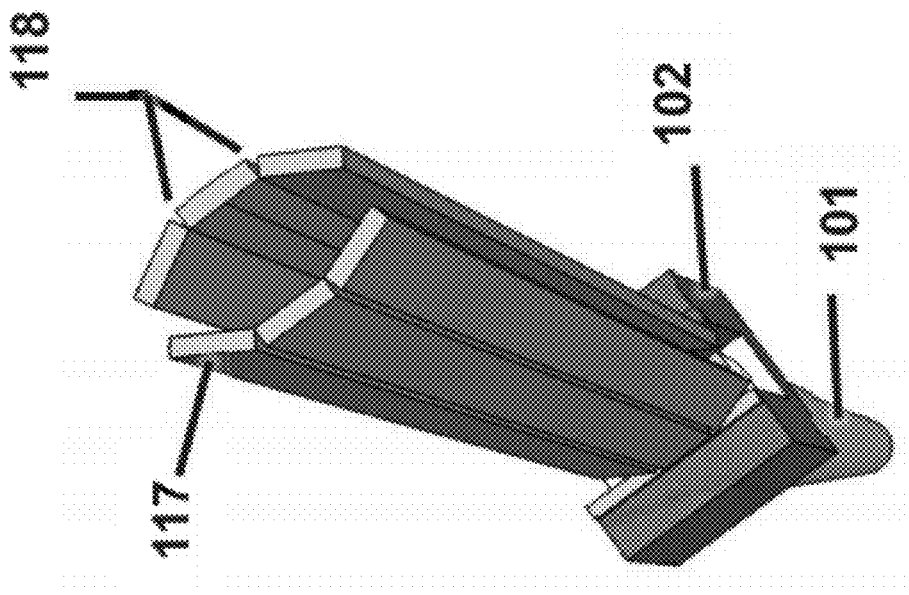
FIGS. 3A and 3B show another embodiment in which the extended blades/tabs have creases and are divided into foldable panels, straight in FIG. 3A and folding to curve slightly in FIG. 3B. Opening the panels permits the guidance elements to accept the rod, while folding the panels aids in guiding a locking assembly downward toward the screw head after the rod has been inserted.
Figure 3A:
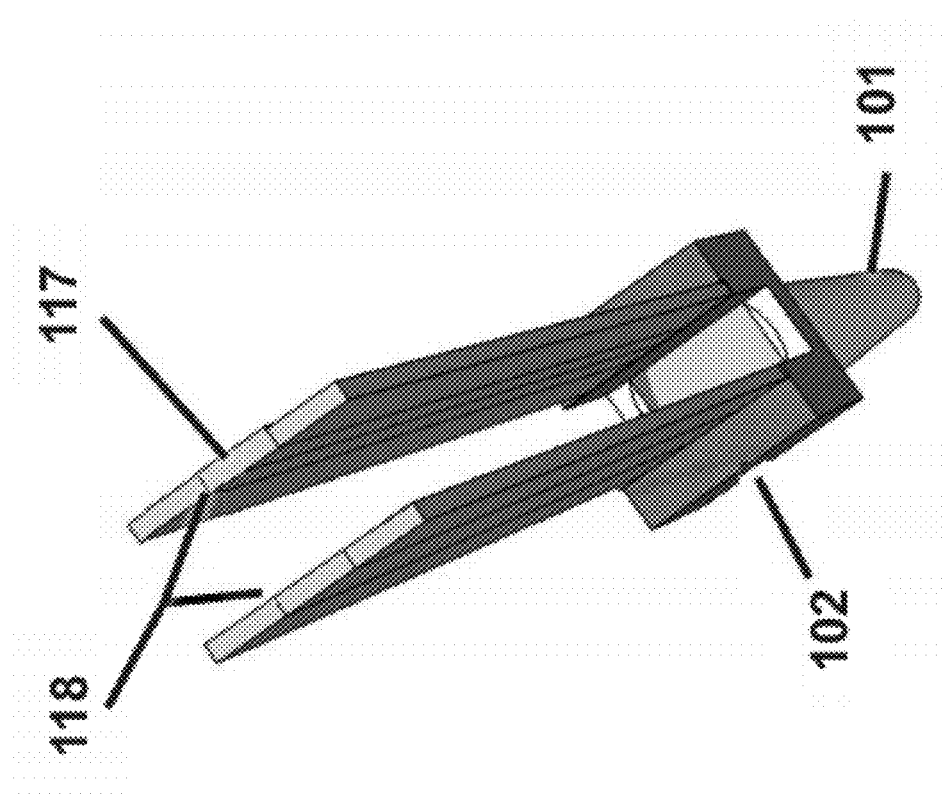

FIGS. 3A and 3B show another embodiment in which the extended blades/tabs comprise foldable panels 117 having creases 118 or hinges such that they can be configured to curve slightly to wrap or partially wrap around a guided element (FIG. 3B). Although three panels (two creases) are shown, more or less panels and creases can be provided. Additionally, although the panels 117 are shown on the inside of the screw head 102, they could also be positioned along the outside 116 of the screw head 102, as shown generally for the guidance elements 114 in FIGS. 1 and 2B. The advantage of the extended blades/tabs with foldable panels 117 is that they can more easily accommodate guided implants and tools of various shapes and sizes. Essentially a blade or tab can be folded to become a tube or partial tube. Thus the foldable panels have advantages of both blades and tubes.

An embodiment of the present inventive system and method is to use one guidance element 103 on each side of a screw head 102 (as shown in FIG. 11A) such that there are two guidance elements 103 per screw shaft 101 to securely trap a rod 104 over the screw shaft 101 within the screw head 102. This embodiment is believed to provide a very high degree of rod 104 stability, while maintaining a very low volume of stabilizing elements (thereby enabling a very small incision without stressing it). The guidance elements 103 can be part of the screw head as an extension of the screw head itself. Or, the guidance elements 103 can be independent elements attached to the screw head 102 through (i) the guidance element itself, (ii) an extension of the guidance element that is formed of a material that is the same as a material from which the guidance element itself is derived, (iii) a thread material thinner than the guidance element, (iv) a short tower, or (v) an intermediate element including an extensor/extended tab 112, flexible sheet, flange 110, or mechanical device/clamp 113 as discussed further herein, among other possibilities. A single guidance element 103 may be attached to a screw head 102 at a single location or in two or more locations 111 as illustrated in FIG. 11B. If the screw head has edges or corners, guidance elements attached to those corners will eliminate the possibility that a rod or locking mechanism is caught on the edge or corner during insertion of the same.

In some embodiments, as a substitute for the extended blades/tabs guiding elements, a plurality of wires can be joined to form a "wall" guiding element similar to the blades/tabs. In some embodiments, the plurality of wires can be flexible, and can be joined by a cuff or strap (e.g., a metal strap) to form a guiding element simulating a long "blade" or "tab" for guiding an implant or tool to a desired location in a patient. The use of a plurality of wires in the form of a "wall" can provide increased flexibility relative to conventional systems, thereby allowing for "wall" guiding elements to criss-cross at various angles at or near a single incision. The "wall" of guiding elements can similarly be configured in a circular shape to form a tube by a circular shaped strap that is attached to one or a few of the wires, thereby allowing the wires to bend independently of each other. A "wall" of wires or guiding elements need not be densely packed. The distance between wires or guiding elements need only to be smaller than the size of the rod or locking assembly such as a locking nut. This way, the rod or locking nut cannot "escape" out of the "wall" formed by the wires/guiding elements.

Figure 4:
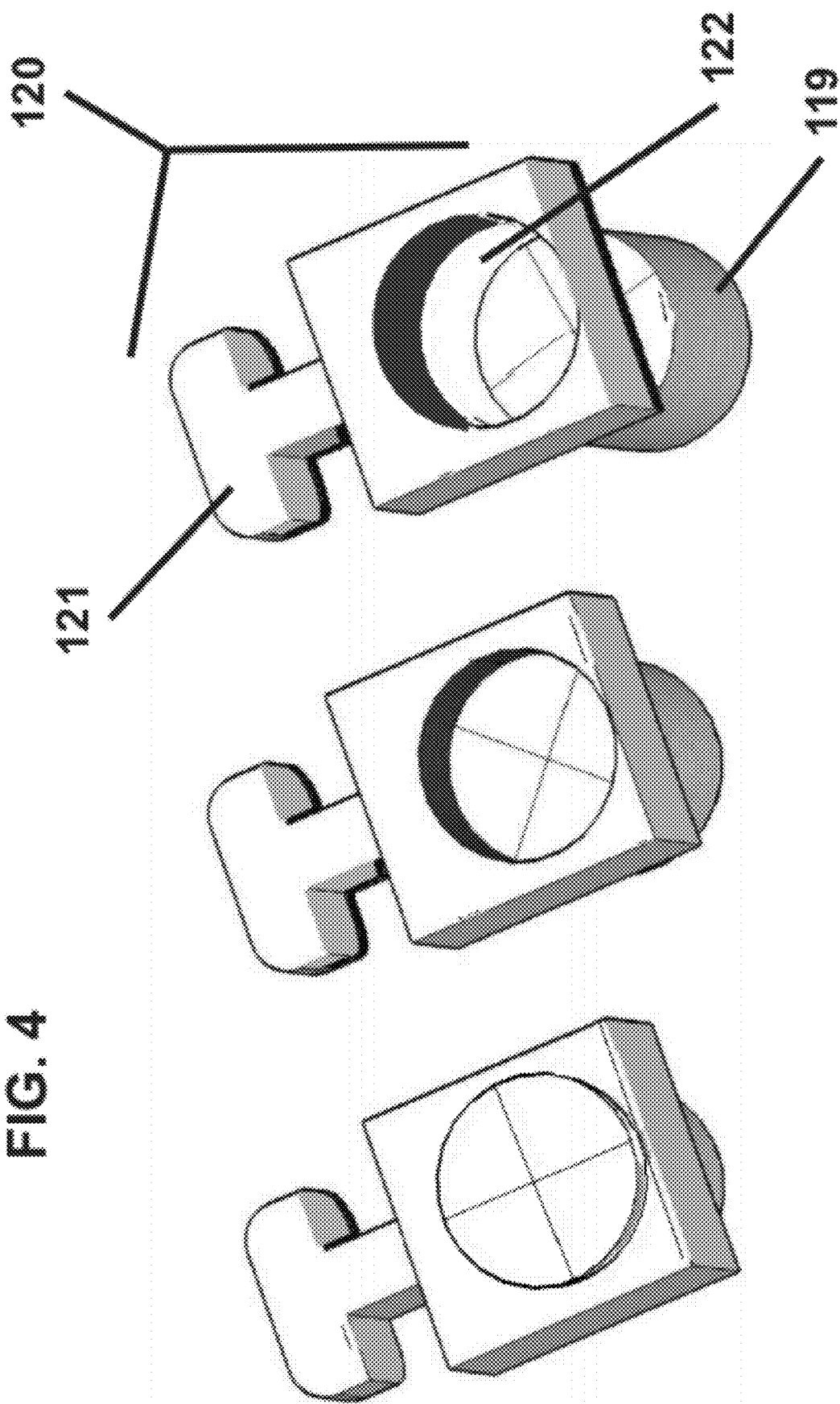
FIG. 4 shows an embodiment for the screw cap locking assembly in which a screw cap transporter has an extended or protruded portion to engage with a corresponding recess or slit in a longitudinally extended guidance element or blade. The screw cap transporter is slid down to fit perfectly on top of the screw head such that the screw cap locking assembly is screwed out of the transporter and into the head of the pedicle screw.
Figure 5:
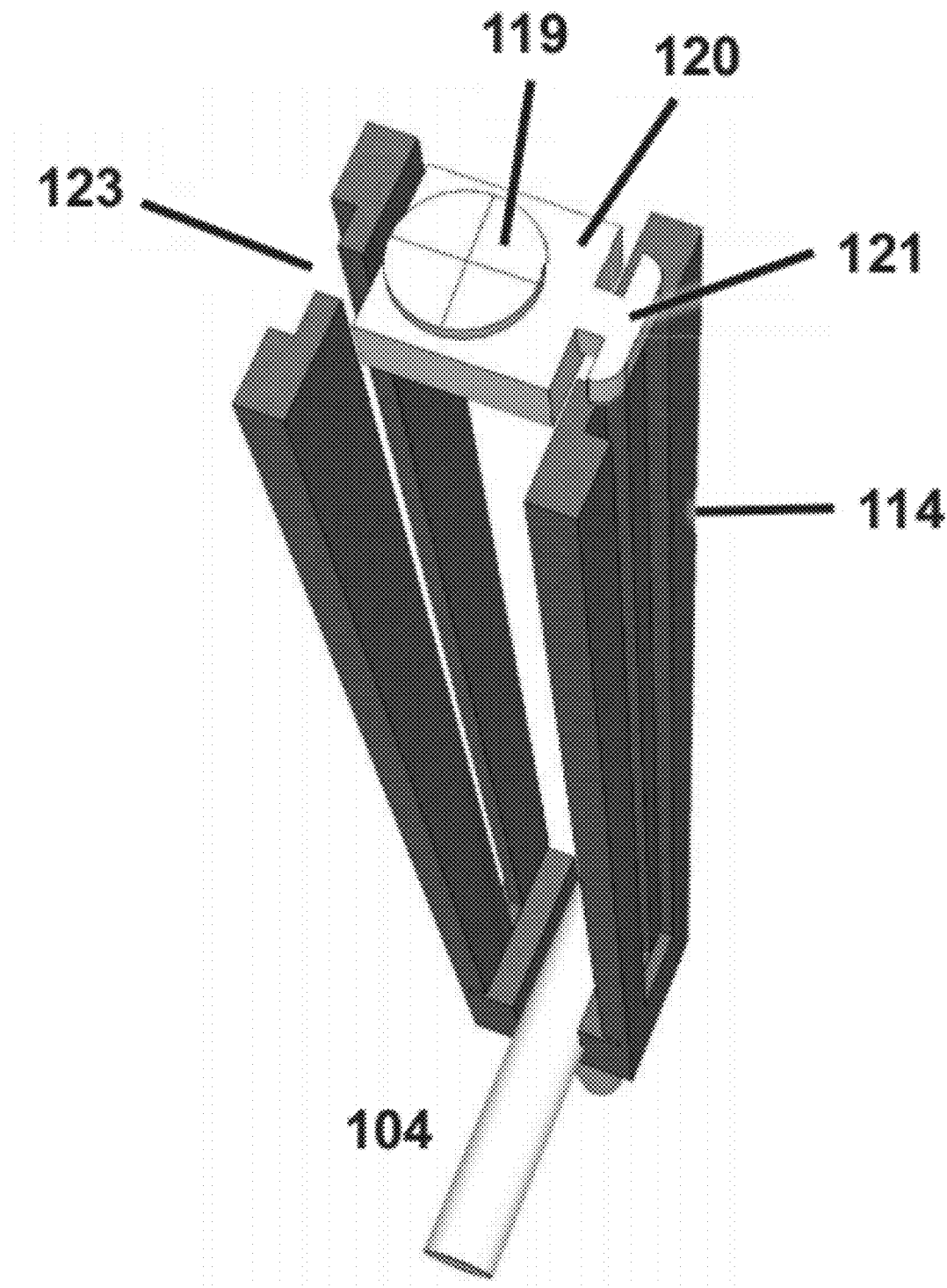
FIG. 5 shows the screw cap and transporter of FIG. 4 in operation, engaging with the recessed longitudinally extended guidance element, to be moved downward to the screw seat, from a perspective looking down from above.
Figure 22A:
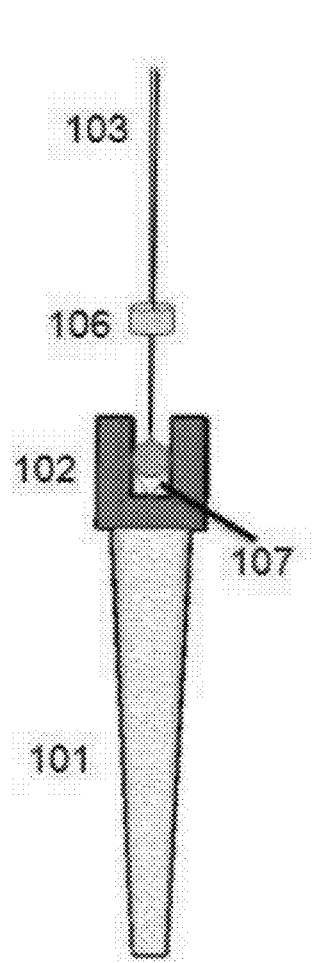
FIGS. 22A-22C show how threads can be wrapped around the rod and brought together to guide a cannulated locking assembly (e.g., cap) as well as other cannulated tools (not shown) down to the screw head.

FIG. 4 shows another embodiment for a screw cap placement mechanism, as compared to a simple cap 106 as shown in FIGS. 20A and 22A. In this embodiment, the screw cap portion comparable to 106 (in FIGS. 20A and 22A) is 119. The screw cap portion 119 can be delivered to retain a rod implant (such as rod 104 in FIG. 20A) in the seat of a screw. The screw cap portion 119 can stay on permanently or can be removable to retain the rod. The remaining portion 120 is a screw cap guidance element to be used with extended blades rather than guiding the cap directly down guidance wires (as in FIGS. 20A and 22A). The screw cap guidance element 120 has a threaded hole 122 with which the screw cap engages and a protruding portion 121. The protruding portion or extensor element 121 engages with a corresponding cutout 123 in the extended guidance element (blade, tab, arm) 114 as shown in FIG. 5.

Figure 6C:
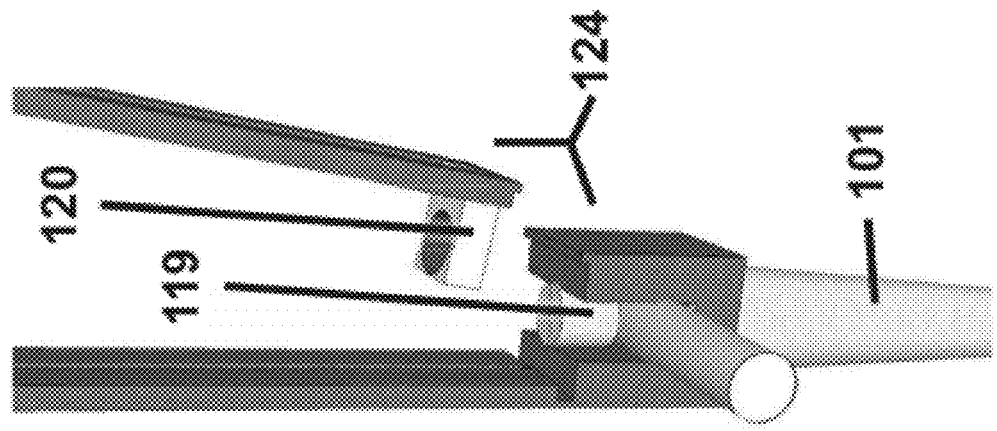
FIGS. 6A-6C show three additional side views of the screw cap locking assembly and transporter element, with the protrusion engaging with the recessed guidance element, and also demonstrating (in FIG. 6C) how the extended guidance element and transporter easily detach from the screw head.
Figure 6B:
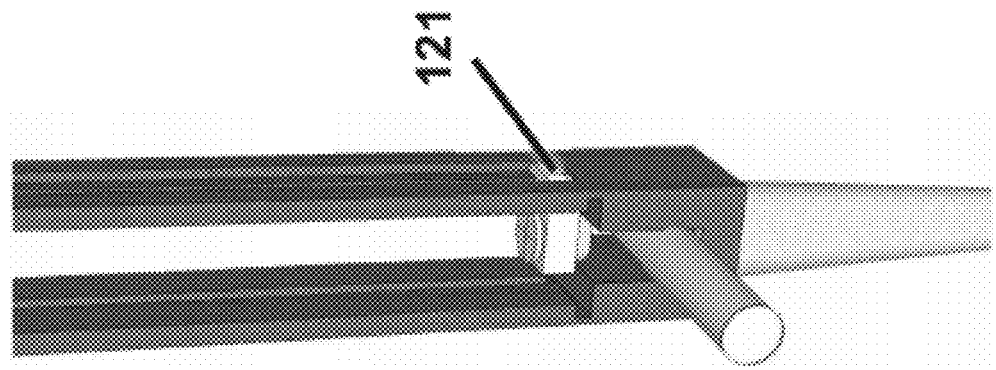
Figure 6A:
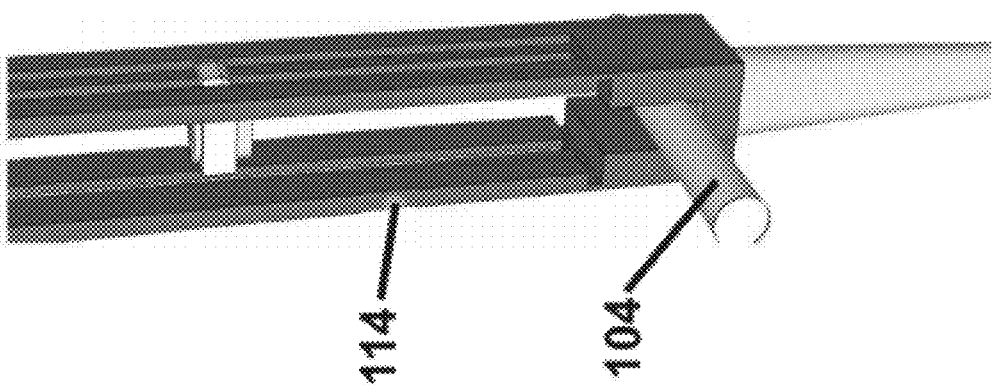

The entire screw cap guidance element 120 can be used to hold the threaded screw cap locking assembly 119 and lead it downward to the screw head 102 using the upwardly directed extended guidance element 114 as a support rail and directional guide. As shown in FIGS. 6A and 6B, the screw cap portion 119 can be guided downward using the extended guidance element 114. When the combination unit (120 and 119) reaches the screw head 102, the screw cap 119 inside can be screwed downward out of the cap guidance element 120 into the screw head 102 immediately above the screw within the screw seat. The cap guidance element 120 can then be removed with the extended guidance element 114, for example by simply detaching from the screw head 102 as shown in FIG. 6C.

Figures 7A, 7B:
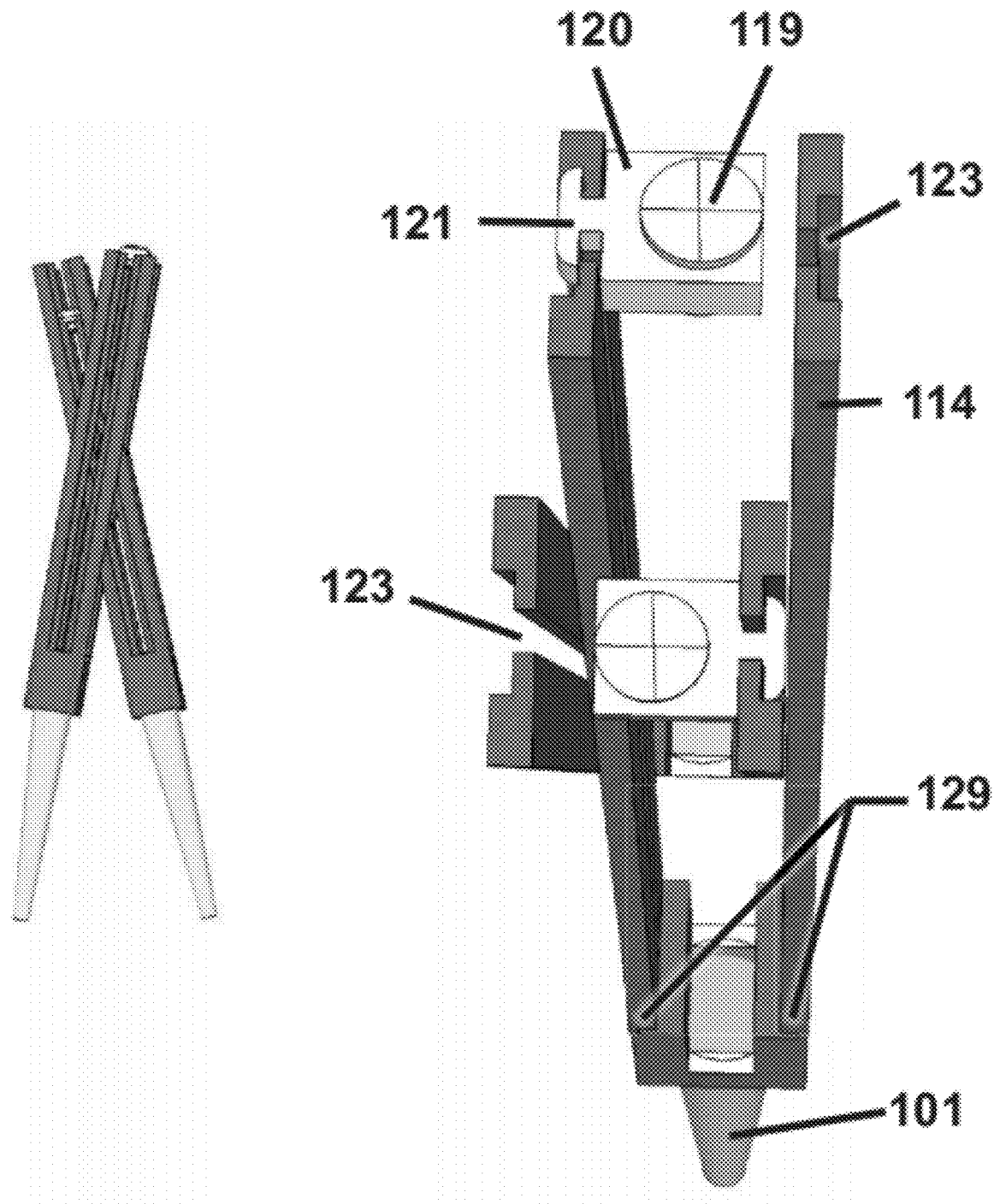
FIGS. 7A and 7B show how the upwardly directed extended guidance elements for two adjacent screws are offset from one another such that their respective locking assemblies (screw caps and transporters with protrusions) can be guided down to their respective screw heads simultaneously without interference.

FIGS. 7A and 7B illustrate how the screw cap guidance elements 120 work as part of the offset guidance system. In this system, extended guidance elements (blades/arms) 114 for adjacent screws can intersect one another without negative interference. With the extended guidance elements 114 crossed, screw caps 119 can still be led down to each screw head 102 simultaneously by the respective screw cap guidance elements 120 without negative interference. Note how the screw cap guidance element 120 for one screw cap 119 (upper) has its protruding portion 121 engaged with a slot 123 in the left extended guidance element 114 of a first screw head 102, while the other screw cap guidance element 120 for the other screw cap 119 (lower) has its protruding portion 121 engaged with a slot 123 in the right extended guidance element 114 of a second screw head 102. Additionally, FIG. 7B shows one option for the attachment of the extended guidance elements 114 to the screw head 102 in which both extended guidance elements (blades/arms) 114 for the lower screw attach to its outer edges on both the left and right sides (outside/outside orientation 129). In order for the criss-crossed configuration shown in FIGS. 7A and 7B to take place, at least one blade of the first screw is preferably flexible, bendable, removable, telescoping, etc. in order to allow the second screw to be placed within the same incision. After the second screw is placed, the blade of the first screw can be replaced, moved, or telescoped to a position in between the blades of the second screw.

Figure 8A:
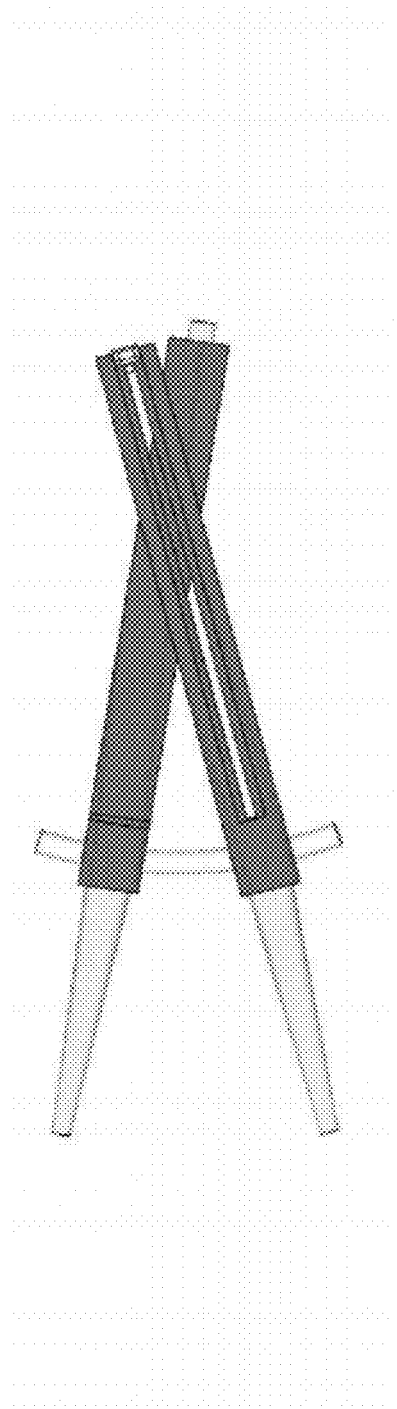
FIGS. 8A and 8B show one arrangement at the base of the longitudinally extended guidance elements in which the guidance elements for one screw (the upper one) are attached to the inside of the screw head, while the elements for the other adjacent screw (the lower one) are attached to the outside of the screw head, such that one set of guide blades (for the upper screw) fits completely within an adjacent set of guide blades (for the lower screw). The guidance elements attached to the inside of the screw head (the upper one) are close enough to allow the screw cap to screw through threads on the blades without a transporter. The widely spaced guidance elements require a transporter to bring the screw cap to the screw head.
Figure 8B:
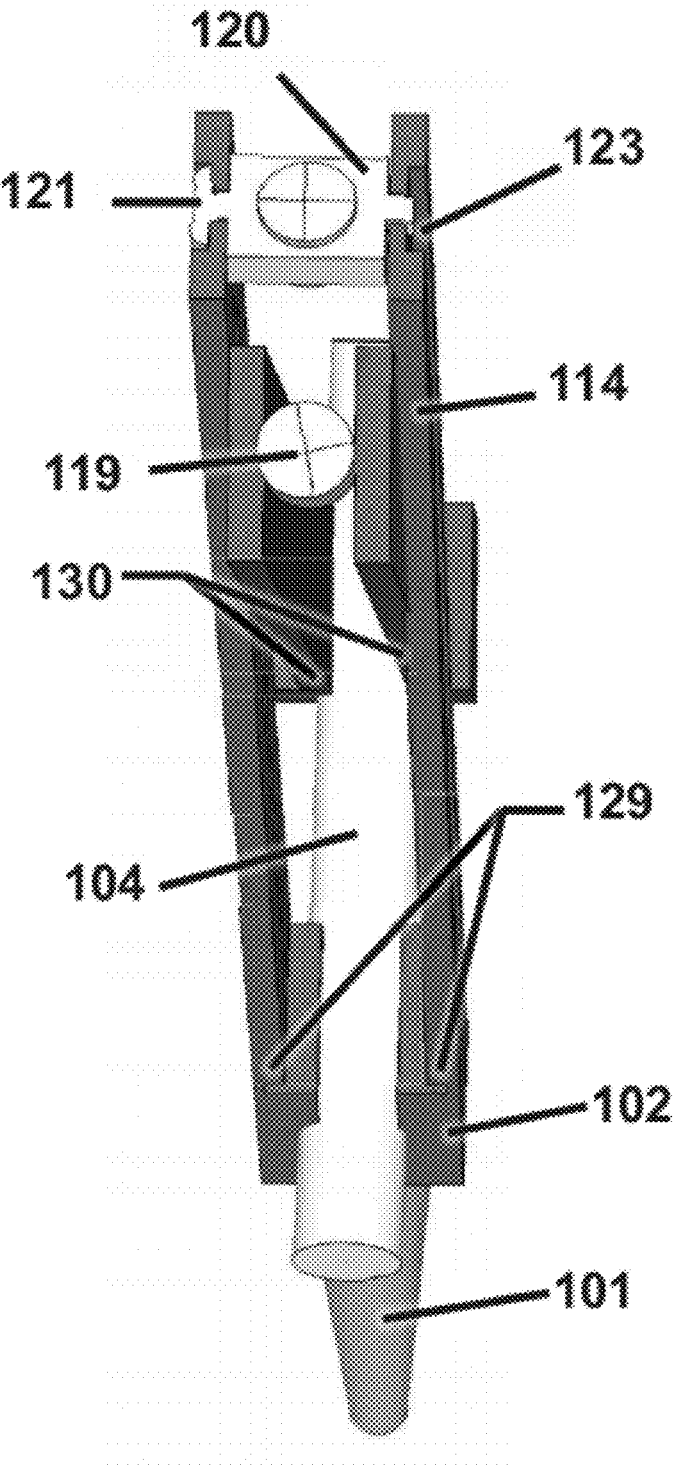

FIGS. 8A and 8B show another option for the attachment of the extended guidance elements 114 to the screw head 102 in which both extended guidance elements (blades/arms) 114 for the upper screw attach to its inner edges on both the left and right sides (inside/inside orientation 130). Thus, a screw head 102 with extended guidance elements (blades/arms) 114 having an inside/inside orientation 130 can fit completely inside another screw head's extended guidance elements 114 that have an outside/outside orientation 129 to cross or intersect in a non-interfering, offset manner. In this arrangement the ordering of blades is: a blade of a first screw; a blade of a second screw; a second blade of the second screw; and a second blade of the first screw. In order for this outer-inner configuration shown in FIGS. 8A and 8B to take place, the screw with the outside/outside orientation is placed first. The second screw with the inside/inside orientation is placed between and through the outside/outside blades of the first screw. The outside/outside blades is preferably flexible, moveable, removable, telescopic, or adjustable in height to allow the second screw to pass through the same incision.

Figures 9A, 9B:
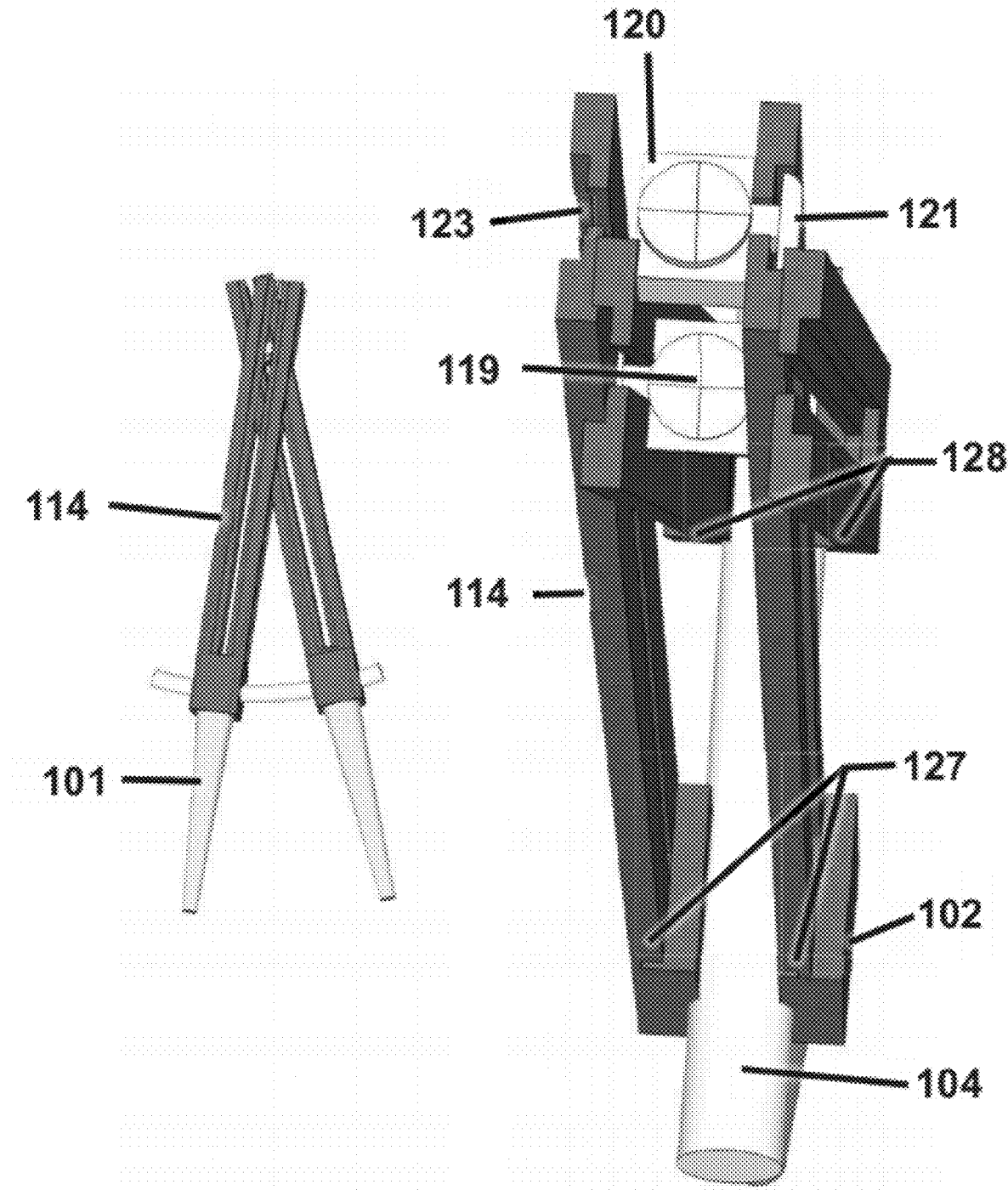
FIGS. 9A and 9B show another arrangement at the base of the longitudinally extended guidance elements in which the guidance elements for one screw (the upper one) are attached to the right side of the screw head, while the guidance elements for the other adjacent screw (the lower one) are attached to the left side of the screw head, for a left-left-right-right offset arrangement of the extended guide blades for adjacent screws when intersecting.

FIGS. 9A and 9B show further options for the attachment of the extended guidance elements 114 to the screw head 102 in which both extended guidance elements (blades/arms) 114 for the upper screw attach to its right edges on both the left and right sides (inside/outside orientation 128). For the lower screw the extended guidance elements (blades/arms) 114 attach to its left edges on both the left and right sides (outside/inside orientation 127). Accordingly, the two sets of extended guidance elements 114 for these adjacent screws can be made to intersect in a non-interfering, offset manner in which the consecutive arrangement is: a blade of a first screw; a blade of a second screw; a second blade of the first screw; and a second blade of the second screw. In order for the criss-crossed configuration shown in FIGS. 9A and 9B to take place, at least one blade of the first screw is preferably flexible, bendable, removable, telescoping, etc. in order to allow the second screw to be placed within the same incision. After the second screw is placed, the blade of the first screw can be replaced, moved, or telescoped to a position in between the blades of the second screw.

FIGS. 10A-10C show another screw cap guidance element called a concentric screw cap placer. The concentric screw cap placer 125 has inner threads that engage with the screw cap 119 along with outer threads 126 that engage with threads on the inside of the extended guidance elements (blades/arms) 114 (not shown). The concentric screw cap placer 125 allows the screw cap 119 to be placed down extended guidance elements with blades that are wider apart than the diameter of the screw cap 119. The threaded feature of the concentric screw cap placer allows a rod to be reduced downwards towards the seat of the screw head by the cap placer even when the guidance elements are widely spaced such as in an outside/outside orientation, as shown in FIG. 8B. The extended guidance elements (blade/arms) 114 should have threads at least at the bottom near the screw head 102 to guide this type of screw cap placer more accurately close to the screw head. After placing the screw cap 119 on the screw head 102 above a rod 104 in the seat of the screw head 102, the concentric screw cap placer 125 may be unscrewed out of the body, upward and off of the extended guidance elements 114. Or the extended guidance elements 114 could be detached and the cap placer 125 removed with them. Or, for extra security or support, in some situations the concentric screw cap placer 125 may be left in position above the rod 104 and screw cap 119, even after the extended guidance elements 114 are unscrewed from it and detached.

In alternative embodiments, a system can be provided that does not use a screw cap 119, set screw and screw placer 125, or guidance element 120. For example, as shown in FIGS. 30A-30D, another embodiment for the rod locking assembly is illustrated in which a screw cap 119 or set screw and screw placer 125 or guidance element 120 (collectively as in FIG. 4 thru FIG. 10C) are not necessary. Rather, the locking assembly 124 shown here is part of the screw head 102 itself. Integrating the locking assembly 124 with the screw head 102 simplifies a surgical procedure by eliminating the step of guiding a separate locking assembly (e.g., 106 as in FIG. 20A, or 119/120/121 as in FIGS. 4 through 9B, or 119/125/126 as in FIGS. 10A-10C) down to the screw head 102. Instead, after the rod 104 is placed, the screw head 102 itself (or portions of it 124) can simply by manipulated to lock the rod 104 in position. For example, the screw head 102 might be turned or rotated such that extensions 124 from it trap the rod 104 against its base 102. Alternatively, portions of the screw head 102 can be manipulated to snap into place around or over the rod 104 or to converge inward to tighten the hold on the rod 104.

FIGS. 11A-11C show embodiments of a minimally invasive system comprising a screw head having guiding elements in the form of wires to assist in the delivery of a rod to the seat of the screw head. The guiding elements create a pathway or channel for the delivery of the rod. Advantageously, the one or more guiding elements on one screw head can intersect with the one or more guiding elements on a second screw head, for example at, near, above or below a skin incision, and can simultaneously assist in blocking tissue or muscle from the pathway which could block the path of the rod during delivery In FIG. 11A, a single guidance element 103 illustrated in the form of a single wire is attached to the screw head 102 having a first wire portion extending from one side of the screw head and a second wire portion extending from the other side of the screw head. The two wire portions in one embodiment may be separate wires. Alternatively, FIGS. 11B and 11C illustrate a second configuration in which one or more shorter guidance elements or wires 111 are attached to the screw head 102 and also attached to a single or multiple elongated guidance elements or wires 103 at their other end. Multiple short guidance element 111 attached directly to the screw head 102 may provide greater stability for an easier alignment. To accommodate this multiple guidance element configuration 111, insertion instruments having side loops (not shown) through which the guidance element passes also have side loops to accommodate the larger area created by the fanning out configuration of the multiple short guidance elements 111 close to the screw head 102. Thus, the side loop attached near the tip of the insertion tool will be as wide as the screw head to accommodate all the short guidance elements at the screw head. Above the transition zone (from multiple guidance elements 111 to a single guidance element 103) the insertion tool will have smaller side loops that only allow a single guidance element to pass.

Figure 17:
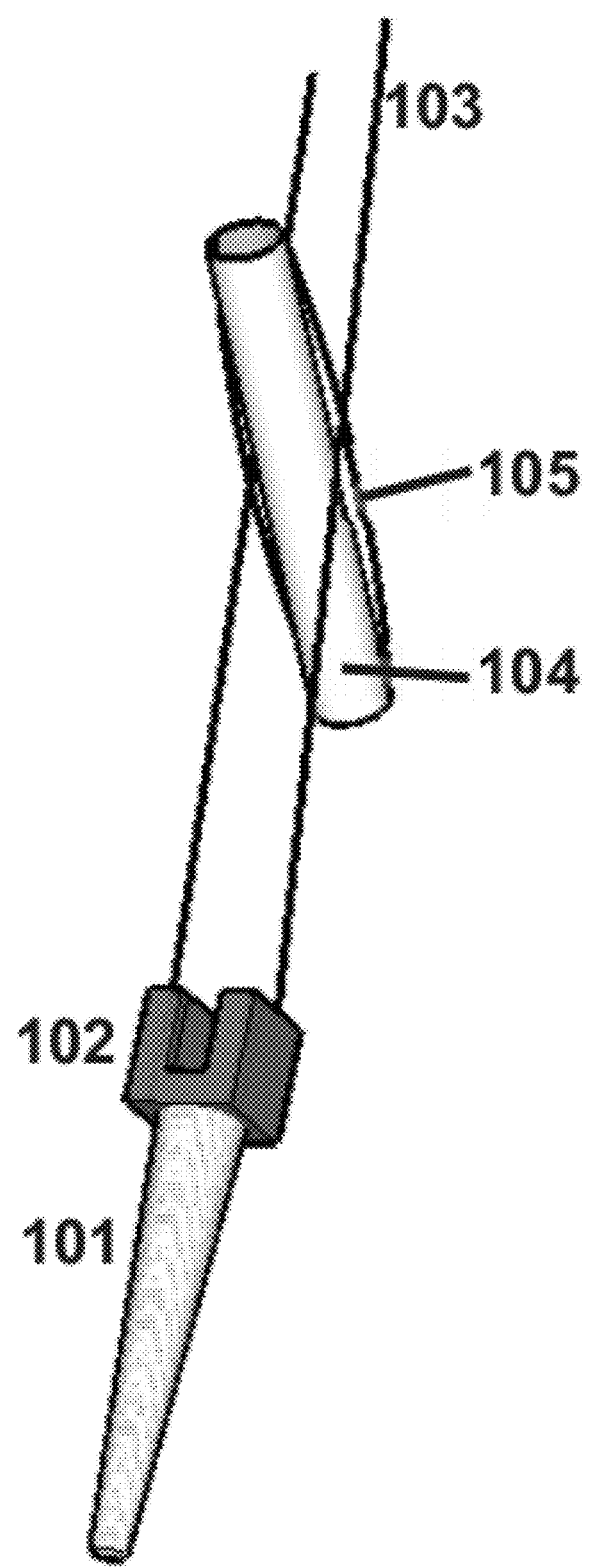
FIG. 17 shows an embodiment in which the rod also has guidance elements or threads (called rod retention threads) on each side extending between its longitudinal ends to form a loop with the body of the rod for securing the rod along the screw head guidance elements during placement.
Figure 18:
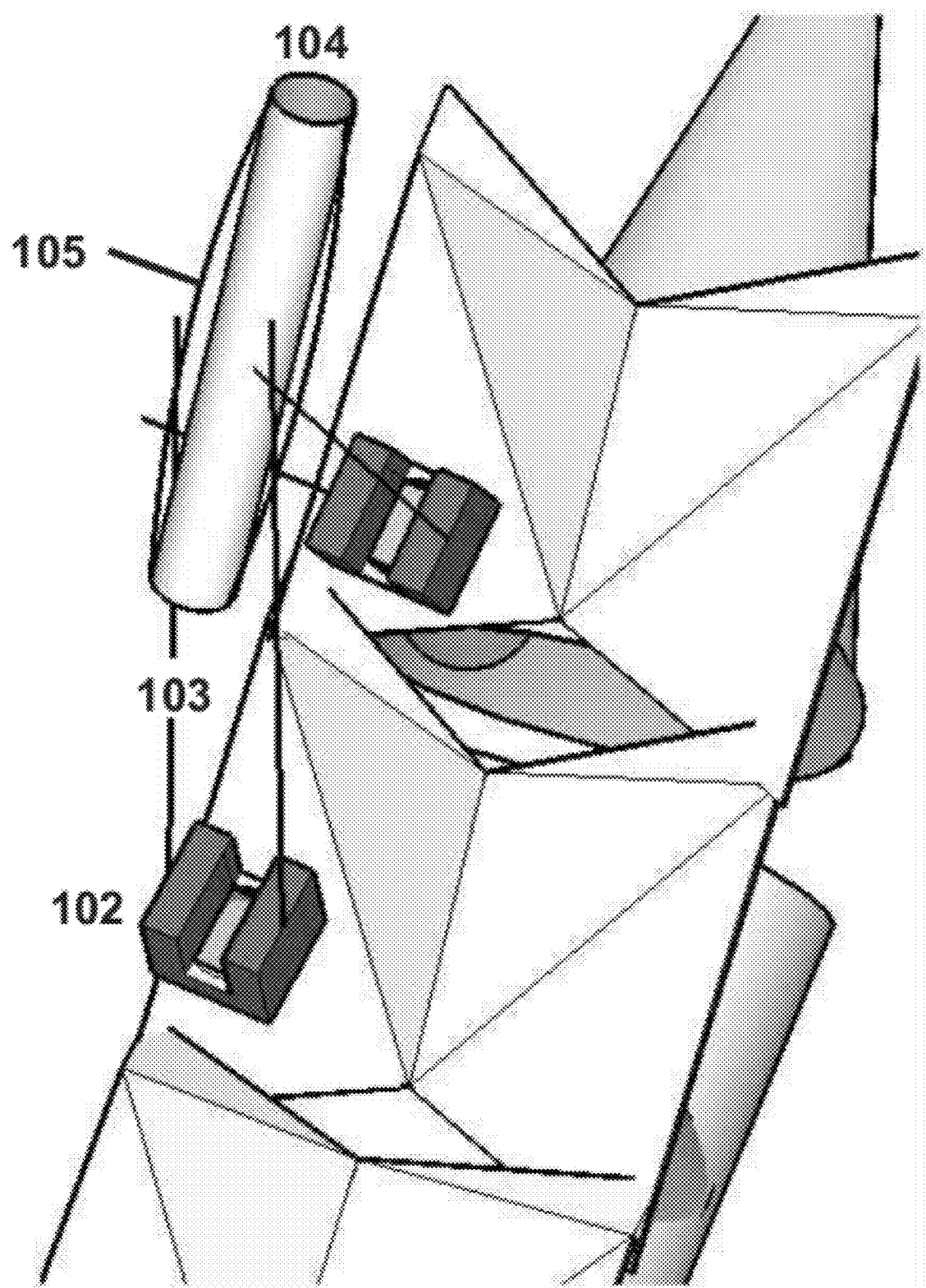
FIG. 18 shows the rod with retention threads being directed down to two screw heads (one for each longitudinal end of the rod), along screw head guidance elements (corresponding to each side of each pedicle screw head) inserted through the rod retention loop on each side of the rod. The rod retention threads "trap" the guidance elements so that the ends of the rod cannot be pushed out of the screw head.

In another embodiment there may be a single guidance element or wire 103 on only one side of each screw 101/102 or screw head 102. This embodiment further reduces the volume of stabilizing elements (screw head guidance elements) that must fit through the minimal incision but may reduce rod stability. When only one screw head guidance element 103 is used per pedicle screw 101/102 it is recommended that at least one rod retention thread 105 also be used (see FIGS. 17 and 18 for illustration of the rod retention threads 105). FIGS. 19A-19F illustrate the steps for delivering the rod to the screw head 102, with the rod retention threads slid over the guidance element or wires 103. FIGS. 20A-20C illustrate a screw cap 106 being delivered between the wires 103 to the screw head 102, where it may be screwed into the screw head 102. The screw head guidance element 103 should be inserted through the loop formed by the rod retention thread 105 along the lateral side of the rod body 104. Rod retention threads 105 can be useful when the rod 104 is bent and the orientation of the bend has to be maintained in a proper direction to match the configuration of the screws. Sometimes a bent rod rotates when inserted and may not fit into the screw heads because the bend is rotated incorrectly so as not to match up with the orientation of the screw heads. Retention threads can reduce this risk and allow for correction in situ if the upwardly directed extended guidance element is in place properly through the thread. Retention threads are also useful to align a rod to fit into the screw heads when the rod does not have a spherical cross section. For example, the rod can have an oval in cross section so that it is stronger in flexion extension (the longer axis of the oval cross section) than in lateral bending (the shorter axis of the oval cross section). Retention threads can limit rotation and force the rod to sit down into the screw heads. When retention threads are used, it may be useful to eliminate the outer edges and corners of the screw head as seen in FIG. 11C. Additional short wires connecting the single upward projecting guidance element to the outer corners would allow the retention thread to slide over the outer edges of the screw head. Alternatively, the outer edges of the screw head is tapered to allow the retention thread to slide down the outer aspect of the screw head when the rod is placed down into the screw head.

In some embodiments, to assist the rod 104 in staying within the guiding element 103 (or any other guiding elements discussed herein), a rod wire (not shown) can be provided that protrudes out of a leading end, trailing end or both of the rod. The rod wire in some embodiments may be capable of snapping off. The rod wire may also be hinged or bent upward relative to the rod to ensure that the rod is delivered in the correct manner. In some embodiments, the hinge may comprise a screw mechanism where the rod wire is screwed onto the rod. Other attachment mechanisms such as described for the guidance elements may also be utilized. The use of the rod wire can provide guidance as to the orientation of the rod as it moves downwardly through the guidance elements, as well as of the position of the rod relative to the guidance elements. This way, it is possible to place the rod in a desired orientation (e.g., vertically) as it moves downwardly through the incision and the guidance elements.

In some embodiments, the rod can be oriented vertically until it reaches a first screw, and afterwards, can be rotated down into the second screw head. In other embodiments, the leading end of the rod is held and guided by a tool that is guided and slid down over the guidance elements of the second screw. In still another embodiment, the leading end of the rod is guided by retention threads that only trap the guiding element of the second screw while the trailing end of the rod is trapped between the guiding elements of the first screw by the rod wire. Accordingly, the rod wire serves as a detachable flexible extension that keeps the trailing end of the spinal implant within the first guiding element when the leading end is first delivered to the second screw by the second guiding element. The flexible rod wire can also be loosely and partially coiled or wrapped around one of the guiding elements of the first screw after the rod wire has passed through and between the guiding elements of the first screw. This configuration also ensures that the trailing end of the rod slides between the guiding elements into the screw head of the first screw. Once the rod is in a desired position, the rod wire can be snapped off, either manually or when enough tension builds from changing the orientation of the rod relative to the wire.

In another embodiment, instead of one or more guidance elements 103, there may be one or more upwardly directed shafts that are not round (not shown) and are attached to a side of the screw head 102. The unique shape of the shaft would prevent insertion tools from turning or rotating around the shaft (e.g., during their descent to approach the screw head 102). Thus any shaft that is not cylindrical would be capable of guiding tools that have a complementary non-cylindrical shaft holder attached to the tool. For example, a shaft that has a cross section of an oval, square, rectangle, triangle, cross, trapezoid, star, or any other shape besides a circle would be able to prevent an insertion tool from rotating around the shaft as long as the insertion tool is equipped with a complementary shaped holder through which the shaft fits precisely. As long as the screw head 102 is multi-axial, there would be some flexibility in moving the shaft around in the incision.

The screws 101 and screw heads 102 themselves may also have any one of several different vertical and horizontal cross-sections including both circular and non-circular, rectangular, square, hexagonal, etc. The screws 101 and screw heads 102 are preferably made of a titanium alloy or stainless steel. In some embodiments, the screw heads 102 include a seat in the form of a channel for receiving a rod member. The seat can assume various shapes, such as half spherical or cylindrical.

The rods 104 are preferably cylindrical but in other embodiments they may have a non-circular cross-section (triangular, square, hexagonal, etc.) so long as the seat of the screw head 102 is shaped correspondingly to accommodate. The rods 104 are preferably formed of a titanium alloy but may also be made of any other metal (commercially pure titanium, stainless steel, etc.) or a biocompatible minimally flexible polymer such as polyetheretherketone (PEEK). The rods can be uniformly or non-uniformly (same or different degrees of flexion along different axis) rigid, semi-rigid, semi-flexible, or flexible. The rods can be straight or angled and may be pre-bent or bendable in situ. Flexible rods may be formed of a uniform flexible substance such as PEEK or may incorporate a joint in the middle of the rod which bends. Or, cuts in a hollow rod allow bending of the rod similar to a spring.

In some cases, other elements, including connectors or T-connectors, can be also introduced, with or without assistance of the upwardly directed extended guidance elements, to cross the spine horizontally and connect two parallel rods to provide additional support.

In another embodiment there may be more than two guidance elements 103 per pedicle screw 101/102. Preferably, if more than two guidance elements per screw are used, there is at least one guidance element on each side of the screw with more than one guidance element on at least one side. An equal number of guidance elements on each side improves stability and prevents lopsidedness. However, every patient's anatomy is slightly different and when curvature (e.g., scoliosis) and/or other aggravating conditions are present stability during rod 104 insertion may be best achieved by an asymmetric distribution of screw head guidance elements 103 around the perimeter of a screw head 102. In any case, the spinal surgeon is in the best position to make this decision about the appropriate screw head guidance element 103 and rod retention thread 105 set-up to use based on the individual needs of a particular patient.

The guidance elements 103 on any one screw 101/102 can be placed at various positions around the periphery of a screw (rather than just on the sides) for enhanced stability and control. Screw 101/102 is used to refer to the entire screw including the screw shaft 101 and the screw head 102 collectively. The guidance elements may be uniformly distributed and symmetrical around the periphery or they may be asymmetrical and staggered. For example, having four guidance elements on a screw head (e.g., one guidance element on each edge: north/top, east/right, south/bottom, west/left) helps provide that the screw head 102 is oriented along the axis of the rod 104 during transport of the rod through the incision and into a first screw head. Limiting the open regions around the perimeter of a screw head 102 by effectively creating a guidance element cage can also force the rod 104 to turn in the right direction (or force the screw head to turn to accommodate the rod) when it moves from a vertical longitudinal to a transverse lateral orientation after placement of a first end in a first screw head while the other end is being directed for placement in a second screw head. The number of guidance elements, their sizes (e.g., diameters and lengths), shapes, flexibility, and strength may be adjusted to suit a particular procedure in a particular patient based on the incision size to optimize screw stability and facilitate rod alignment while avoiding entanglement of too many guidance elements. Contemplated embodiments include those with from 1 to 10 guidance elements per screw/screw head, and more especially those with 2 to 4 guidance elements.

Instead of multiple long guidance elements connected to the screw head 102 on each side, a single long guidance element 103 (or thread) is connected to several short guidance elements 111 which in turn are connected to each side of the screw head. Thus, multiple guidance elements 111 are still connected to each screw head 102 but these multiple guidance elements are also connected to one another in an area above the screw head to form single guidance element 103 extending through the incision. These multiple short guidance elements 111 may still function to bound or limit the movement of a rod 104 at least at the base of the screw head 102. The short guidance elements 111 give the advantage of creating a guidance element cage by which the rod 104 is forced to sit down into the seat of the screw head 102. The long single guidance element (or thread) 103 reduces clutter and confusion at the skin incision that occurs when too many guidance elements are present. The multitude of short guidance elements 111 distributed away from the longitudinal entry axis into approximately the same axis along which the rod 104 will ultimately lay also allows the long guidance element 103 and accompanying instruments to adjust the orientation and angle of the screw head 102 in this axis (the rod axis, approximately perpendicular to the longitudinal entry axis used during rod insertion). The screw head 102 is configured to form a concave channel in which the rod 104 will eventually come to sit/rest. The concave channel may be U-shaped when a vertical cross-section is taken but any substantially concave shape suited to retain a rod 104 and with dimensions corresponding to those of the rod 104 will work. The upper edges of the screw head 102 itself or those of another intermediate element 110/112/113 to which it is attached, are configured to receive an incoming rod at a wide range of angles and smoothly direct it into the proper angular configuration to fit into the screw seat.

As an alternative to the screws 101 or the screw heads 102 being attached directly to upwardly directed guidance elements 103 or guide shafts, there may be an intermediary flange, flanged leaflet, sheet 110, extensor/extended tab 112, a mechanical clamp/device 113, or other element in between the two. The screw 101/102 or screw head 102 at its outer edges may transform into (integral therewith) or attach to a separate element that is directly attached to the guidance element/shaft 103 such that the screw 101/102 or screw head 102 and the guidance element 103 are indirectly connected. The intermediate element is preferably specially adapted to readily detach from the screw 101/102 or screw head 102 when desirable, such as after securing the rod 104 in proper position and locking it in place. Detachment may be through a snap-off/pop-off mechanical mechanism that might be activated through a push-button on a surgeon's tool; through tearing along a perforation; through cutting, twisting, wagging, burning, heating, radiating, ultrasonically vibrating, electrifying/electrocuting, dissolving, unscrewing, or any other means. In this case with the guidance elements or upward shafts 103 attached directly to the intermediate and readily detachable element 110/112/113 the guidance elements 103 themselves may be more securely fastened to the intermediate element 110/112/113. For example, the guidance elements 103 might be soldered or welded to an extensor tab 112 that snaps into/onto and snaps out of/off of a groove or protrusion on the screw head 102. At least a portion of the extensor tab 112 may be threaded to mate with a screw 101/102 or screw shaft 101 having corresponding threads or to align a rod 104 having some corresponding threads.

The intermediate element may be in the form of a sheet 110 of a very thin material that is both flexible and can be tensed by pulling or tightening. When pulled tight the sheet 110 functions to guide the rod 104 into the seat of the screw head 102. Such material may be rubber.

An intermediate element may be an inwardly tapered flange 110 attached to an inner top edge of the screw head 102 and placed symmetrically about the screw seat in which the rod 104 sits. Such a flange 110 is configured to allow a malaligned rod 104 or screw head 102 to rotate and adjust relative to one another as the rod is inserted into the seat of the screw head until the two are acceptably aligned. The inwardly tapered sides of the flange 110 may take the form of convexly curved wings 110 that form a channel for the rod 104 between them. FIGS. 26A-27B show embodiments of flanged attachments 110 that help the rod 104 to find the proper orientation to best fit into the screw head 102. As shown, each attachment 110 is preferably convex in a direction towards the rod so that as the rod approaches the screw head, the entrance to the screw head can accept a large range of angles in which the rod is oriented and still receive the rod, gradually improving the rod's orientation as it gets closer to the seat of the screw head. FIGS. 27A and 27B show two sequences of lowering a rod into a malaligned screw head (or, of lowering a malaligned rod into a properly aligned screw head) using flanged attachments. The bi-convex nature of the flanged attachments permits the rod to twist and adjust as it is lowered. Otherwise, without the flanged attachments, in a malaligned situation the rod would hit the edges of the screw head and would not be able to be lowered further. The flanged attachments are shown here as detachable elements on the screw head; however, another preferred embodiment is a flanged and convex shaped rod guide built into the tops of opposing sides of the "U" shaped screw head (e.g., may be integrally part of the screw head interior itself). The flanged attachments 110 in one embodiment may further have wires (not shown) extending upwardly therefrom as described elsewhere herein.

Figure 28A:
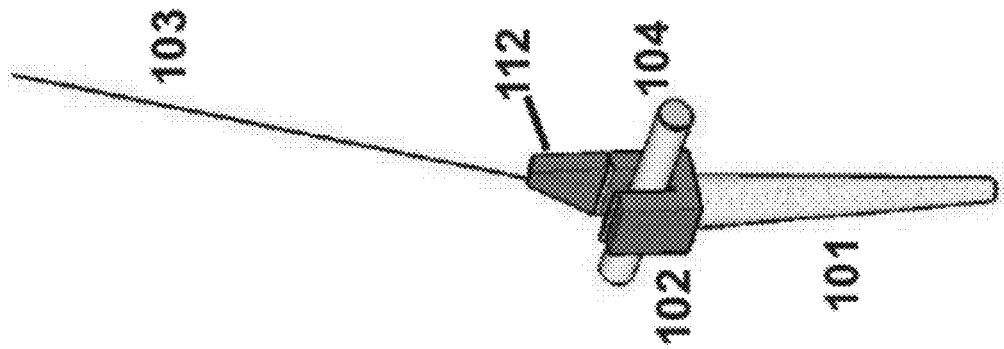
FIGS. 28A-28C show another embodiment in which a guidance element is connected to a screw with break off extended tabs. Extended tabs are used to help reduce the rod into the screw head in cases of malalignment of the screw heads. Extended tabs are removed by snapping them off after the rod is locked in place. A guidance element attached to the extended tab helps to guide the rod and locking assembly into the screw head. The guidance element is removed when the extended tab is removed. Extended tabs that are tapered or triangular in shape also act similarly to flanged attachments to guide a rod into the seat of a malaligned screw head.
Figure 28B:
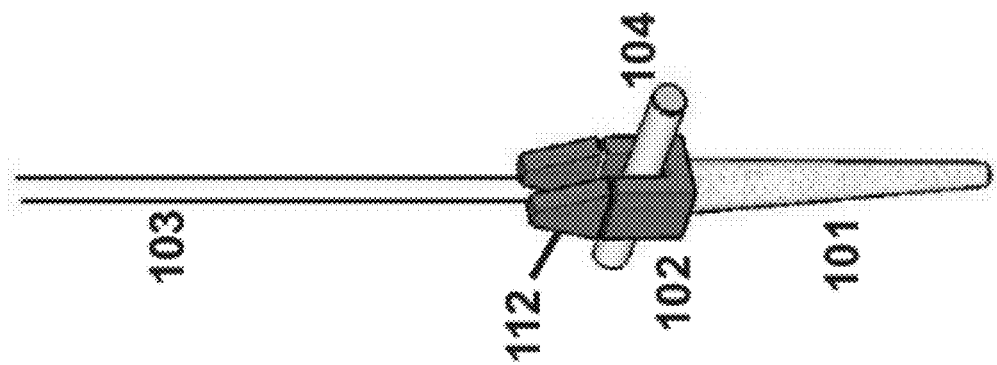
Figure 28C:
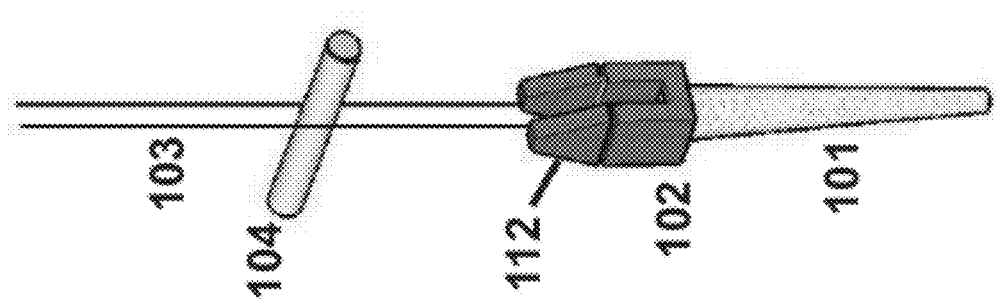
Figures 30A, 30B, 30C, 30D:
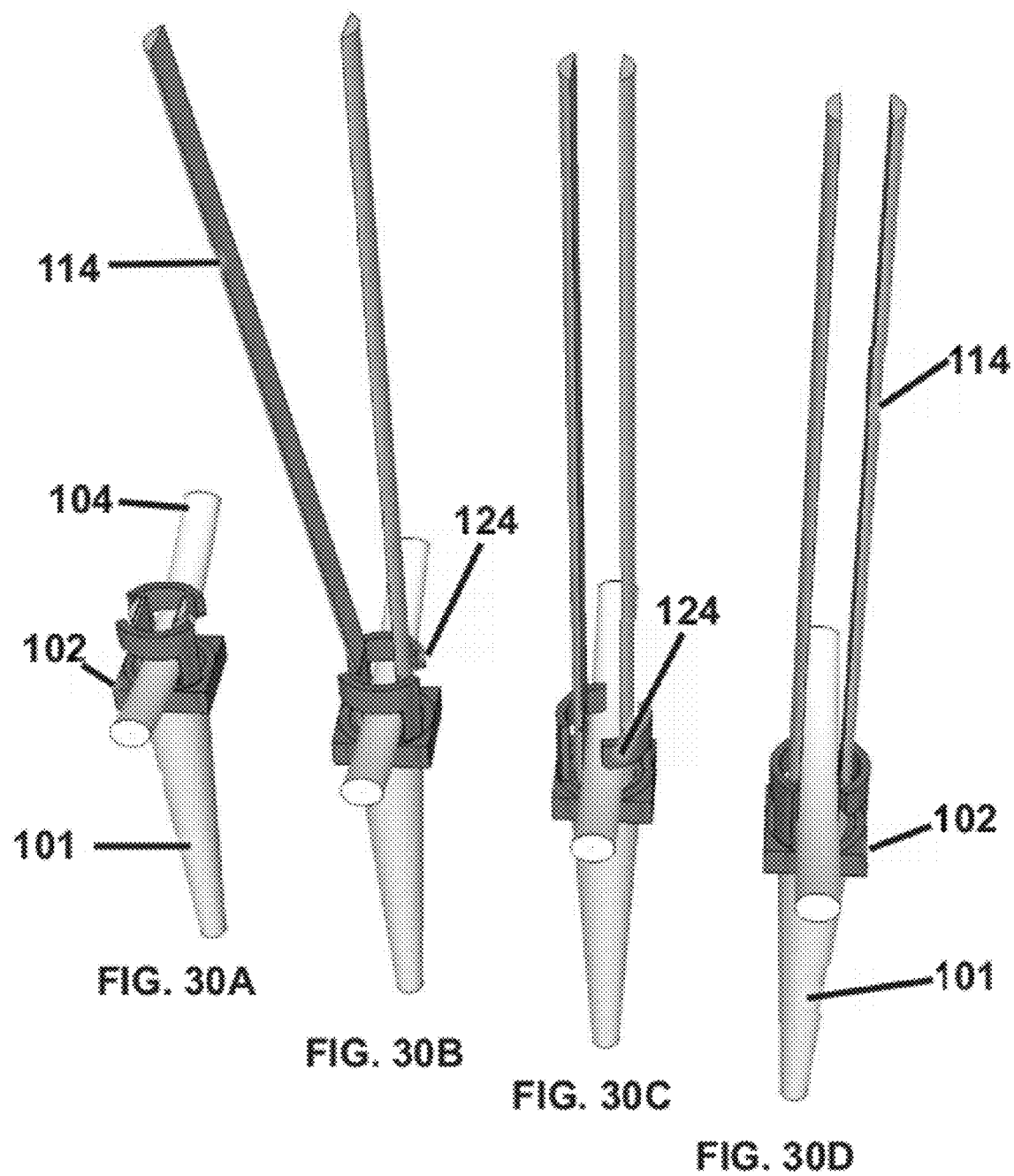
FIGS. 30A-30D shows an embodiment for the locking assembly in which the screw head itself forms the locking assembly and no caps or set screws are needed. In this particular embodiment the screw head can be rotated to trap the rod.

Or, the intermediate element may be an extensor tab 112 with straight rather than convex sides. Preferably, the tab is triangular which may be formed by removing the corners of an otherwise rectangular tab. The wider base of the triangle may attach to the screw head 102 as shown in FIGS. 28A-28C.

The screw head 102 or intermediate element 110/112/113 provides a channel into which a rod 104 can be easily guided by the upwardly directed guidance element 103 or guide shaft. The screw head or intermediate element is advantageously adapted to accept a large degree of malalignment of the rod and the screw seat relative to one another and then guide the rod into the screw seat until substantially perfect alignment is achieved. The advantage of this is that the system does not require starting over, pulling out, and reinserting the rod when it turns out the initial positioning is not ideal.

The guidance elements, threads, and intermediate elements described herein may be attached to the screw or screw head on the outside, on the inside, or through a cannulated portion of the downwardly directed screw shaft 101. Many attachment locations are possible so long as it does not interfere with the ability of the screw shaft 101 to be drilled into the pedicle and the ability of the rod 104 and locking assembly 106 to be received into the seat of the screw head 102.

The guidance element, thread, or upwardly directed shaft 103 may be attached to the downwardly directed screw shaft 101, the screw head 102, or an intermediate element (e.g., flange, sheet 110, extensor/extended tab 112) with glue, soldering, thread, sutures, string, a mechanical clamp 113, etc.

In embodiments in which a mechanical clamp 113 is used to connect the upwardly directed extended guidance element 103 to the screw head 102, the clamp 113 preferably has two leaves that are connected under the head 102 or at least below where the rod 104 comes down so as not to impede the path of the rod. After closing the locking assemblies 106 to secure the rod 104 in place within the screw head 102, the clamps 113 can be removed. Removing the clamps 113 from the screw head 102 also removes the guidance elements 103 attached to the clamps 113. The clamps 113 may be removed by any means feasible in the limited space including (but not limited to): (i) by breaking the connection (like detaching the extended tabs 112), (ii) by cutting a material that holds the 2 leaves together, (iii) unclamping or unbuckling, and (iv) unvelcro-ing.

Or, in some embodiments the locking assembly may be part of the clamp 113 such that the clamp is not removed but remains to hold the rod 104 (see FIG. 29A). In such situations, the guidance elements 103 are simply detached from the clamp-locking assembly combination unit.

Instead of a mechanical clamp with moving parts, the intermediate element (between screw head 102 and guidance elements 103) may also simply be a metal or plastic device that has no moving parts but traps the head 102 securely into it. The intermediate metal or plastic device can be removed by means including (i) snapping a thin center part connecting 2 halves of the device, or (ii) cutting a string that connects two parts of the device. If the locking assembly 106 for the rod 104 is distinct from the intermediate metal or plastic device, then the device can be removed along with the guidance elements after the rod is placed. If the locking assembly is integrated with or dependent upon the intermediate metal/plastic device, then the device should stay in place after the guidance elements 103/111 only are detached from it.

Figure 22B:
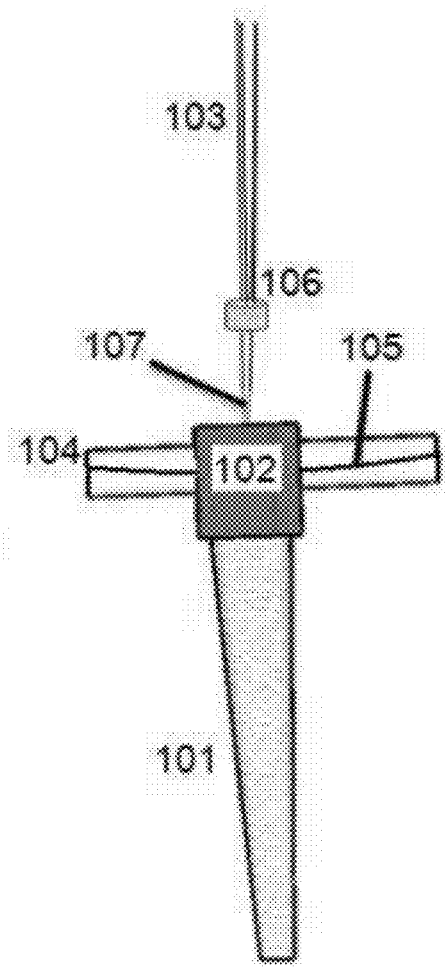
Figure 22C:
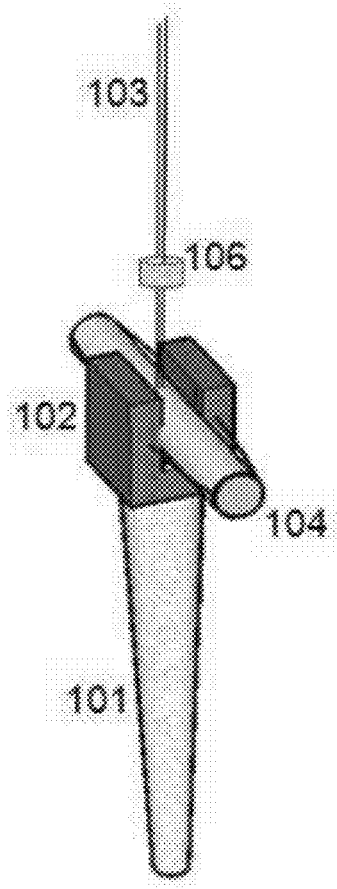

In another embodiment illustrated in FIGS. 21A-21F, the guidance element 103 or an extension thread 107 thereon can be attached to the area within the screw head 102 where the rod 104 would eventually sit, such as at the base or sides of the screw head and/or to the upper end of the downwardly directed screw shaft 101. For example, the guidance element 103 or its extension 107 may be attached within the cannulated portion of a cannulated screw. By using a flexible guidance element or extension thread 107, the guidance element/thread can wrap around the rod 104 as the rod is seated into the screw head 102. The guidance element/thread can then be threaded through cannulated tools and a cannulated locking assembly 106 above the rod. FIGS. 22A-22C show how threads 107 can be wrapped around the rod and brought together to guide a cannulated locking assembly (e.g., cap 106) as well as other cannulated tools (not shown) down to the screw head 102.

Optionally, color-coded guidance elements 103 and/or screws 101 may be provided to assist doctors, technicians, and medical personnel in identifying elements, performing the procedure, and monitoring progress during follow-up visits. Or, some other form of visual coding, such as with particular materials and/or only visible under certain conditions may be used to distinguish guidance elements, screws, and other elements (e.g., fluorescent markers, radioactive isotopes, radioopaque markers visible on X-rays, magnetic nanoparticles, etc.). Another alternative or complementary coding means can be sensed by touch (different surface textures) or sound (tactile or auditory) rather than or in addition to visually. The coding could be correlated with right and left sides of the body, medial vs. lateral elements, guidance element/screw sizes, guidance element/screw shapes, guidance element flexibility, and/or guidance element strengths, among other possibilities. This list of variables with which a coding or tagging system may correspond is intended to be illustrative rather than exhaustive. One coding system provides markers or color coding for guidance elements that are intended for the medial side of the rod versus those intended for the lateral side of the rod. This coding would allow for easy separation of the guidance elements 103 when the rod 104 is inserted. This coding would also help the insertion of tools and the locking assembly 106 along the medial side and lateral side guidance elements 103. Some elements (guidance elements 103, screws 101, screw heads 102, rods 104, retention threads 105, locking assemblies 106, etc.) with similar characteristics may be coded in groups such as all medial side guidance elements being red while all lateral side guidance elements are green. Another variable feature that can be used to code medial and lateral guidance elements is length of the guidance element. Shorter lengths can code for medial while longer lengths code for lateral or vice versa.

Any locking assembly 106 can be used in certain embodiments of the present invention. The precise design of the locking assembly 106 is not important so long as it is configured to retain the rod 104 within the screw head 102 for a secure and lasting stabilization. Examples of locking assemblies 106 that might be employed include screw-on nuts, press-on caps, fast-drying glue, a tiny swinging gate or door with a latch, a series of elements that can be deployed to tighten around the periphery of the rod, etc.

Since a rod connects two or more separate vertebrae, the rod can first be secured into position (locked or tightened) though the locking assembly on a first vertebra and then subsequently on a second vertebra. In some cases after the rod is firmly secured to the screw on the first vertebra, the relative positioning of the vertebrae can be adjusted by the surgeon by moving the vertebrae closer together or farther apart before the rod is secured to the screw on the second vertebra. With only one side of the rod locked into place the other side of the rod can easily be adjusted in position. For example, the rod can vertically slide forward or backward through the locking assembly until the desired distance spanned by the rod between locking assemblies is obtained.

The guidance elements 103 can be attached to the screw heads 102 by a number of mechanisms. The retention threads 105 can be attached to the ends of the rods 104 by the same assortment of mechanisms. The simplest attachment mechanism is to solder or glue the guidance element/thread to the screw head/rod. The solder or glue can then be cut or broken off later. Neither the lateral retention threads 105 on the rod 104 nor the upwardly directed extended guidance elements 103 on the screw 101/102, or on the screw head 102, are needed after the rod 104 has been securely placed within the screw head 102.

The retention threads 105 on the rod 104 that hold it close to the guidance elements 103 as it is guided into position are preferably made of a flexible material including metal, nitinol, rubber, suture, plastic, polymer, and biodegradable material. The retention thread 105 should be easily removable after the rod 104 has been secured in an aligned position in the seat of the screw head 102 and locked in.

Or, the guidance element/thread could be threaded into a threaded connector in the side of the screw head/rod so that the guidance element/thread is unscrewed at the end of the case.

Other embodiments include attaching the guidance element 103/retention thread 105 by dissolvable sutures attached or tied to the screw head 102/rod 104 and to the end of the guidance element/retention thread with a small loop or grooves in the screw head/rod. Suitable dissolvable suture materials include biocompatible synthetic absorbable materials such as those made primarily of polyglycolic acid (PGA) or other proven compositions. Specific brands of materials include Vicryl™ (from Ethicon), Biovek™ (from Dynek), Visorb™ (from CP Medical), Polysorb™ (from Covidien's Syneture), and Dexon™ (also from Covidien's Syneture). The materials can be tailored to degrade or absorb in an amount of time that corresponds with sufficient internal healing to successfully hold the fusion. For example, standard Vicryl™ typically maintains tensile strength for three to four weeks. The materials may also be impregnated with drugs or biomolecules (e.g., triclosan) to accelerate the healing process and prevent infection. When the biodegradation (e.g., bioabsorption, bioerosion, etc.) time for the suture material is too long and the sutures are unnecessary immediately following the procedure the sutures can instead be promptly cut or burned at the end to disconnect the guidance element/retention thread from the screw head/rod.

Yet another option for the "guidance element to screw head" or "retention thread to rod" attachment mechanism is to secure using a material that burns, breaks, or dissolves upon the application of current (e.g., radiofrequency current). This option permits the connection to be easily broken by simply passing current through the guidance element or thread. Preferably, the guidance element/retention thread breaks down in response to current applied outside the skin. Or, an insulated guidance element can be used to apply current internally in a targeted and minimally invasive manner. An insulated guidance element would allow the current to pass directly from an external tip (outside the body) to the current-sensitive material at an interior tip near the pedicle screw.

In still another embodiment for attachment, the selected material (e.g., elastic string or rubber) is both flexible and can be tensed by pulling or tightening. The key is to use very thin material that can be both flexible and become tense. These dual properties allow the material to reliably guide the rod and tools down through the small incision without breaking while adapting to share the limited space. Unless it is also biodegradable the flexible, tensile material of string/rubber will need to be cut/broken/burned off or untied from the screw head and guidance element (or rod and retention thread) at the end of the procedure.

Instead of using an intermediary material to connect the guidance element to the screw head and/or to connect the retention thread to the rod, another possibility is for the guidance element and/or retention thread to be formed of the same materials as the intermediary connectors described above. In this situation, it is the guidance element or retention thread that is itself burned or cut at the end of the procedure.

The final result in all cases is a clean, successful pedicle screw fusion just like that which results from screws and rods used in an open procedure but with a smaller incision and fewer components.

The material through which the rod-guiding guidance element is attached to the screw head may be the same material of which the guidance element itself is derived or a separate material. The guidance elements themselves are preferably formed of a biocompatible metal having both strength and durability. In a preferred embodiment, the guidance elements are formed of nitinol (nickel titanium alloy).

The material through which the retention threads 105 of the rod 104 are attached to the ends of the rod may be the same material of which the retention threads themselves are derived or a separate material. The retention threads are preferably formed of a biocompatible metal having both strength and durability. In a preferred embodiment, the retention threads are formed of nitinol (nickel titanium alloy). In another embodiment the retention threads of the rod to be made from a biodegradable thread so that it does not have to be removed after placement. Another advantage of thread is that it would not interfere with the rod and cap locking mechanism 106 if it were caught in between the cap 106 and screw head 102 threads.

To complement the guidance element guides 103, certain embodiments of the present invention also provide a special rod 104, with its own retention threads 105, that can fit between the guidance elements. By attaching a small loop or ring at the ends of the rod, two threads can be tied though the loops with good tension along the sides of the rod. This way the guidance elements 103 will pass in between the rod 104 and the thread 105 to prevent the rod from slipping out and around the most superior or inferior guidance elements. (See FIGS. 17 and 18.) The retention thread 105 may also be attached to the rod by means other than loops or rings at its ends. The rod 104 may have holes or piercings therein for securing the thread to it. The rod may have grooves at its ends with which the thread engages. The thread 105 may be glued on near the ends of the rod. Rod retention threads 105 restrain the rod 104 to riding the guidance elements 103 and eliminate the risk of internal rod displacement away from the target screw site 102. The retention threads 105 also expedite rod 104 placement into the screws 102/101 to decrease total procedure time.

The retention thread 105 may take the form a strip or long sheet of material rather than an ordinary thread. The retention thread material should be flexible, strong, and biocompatible.

Figure 12:
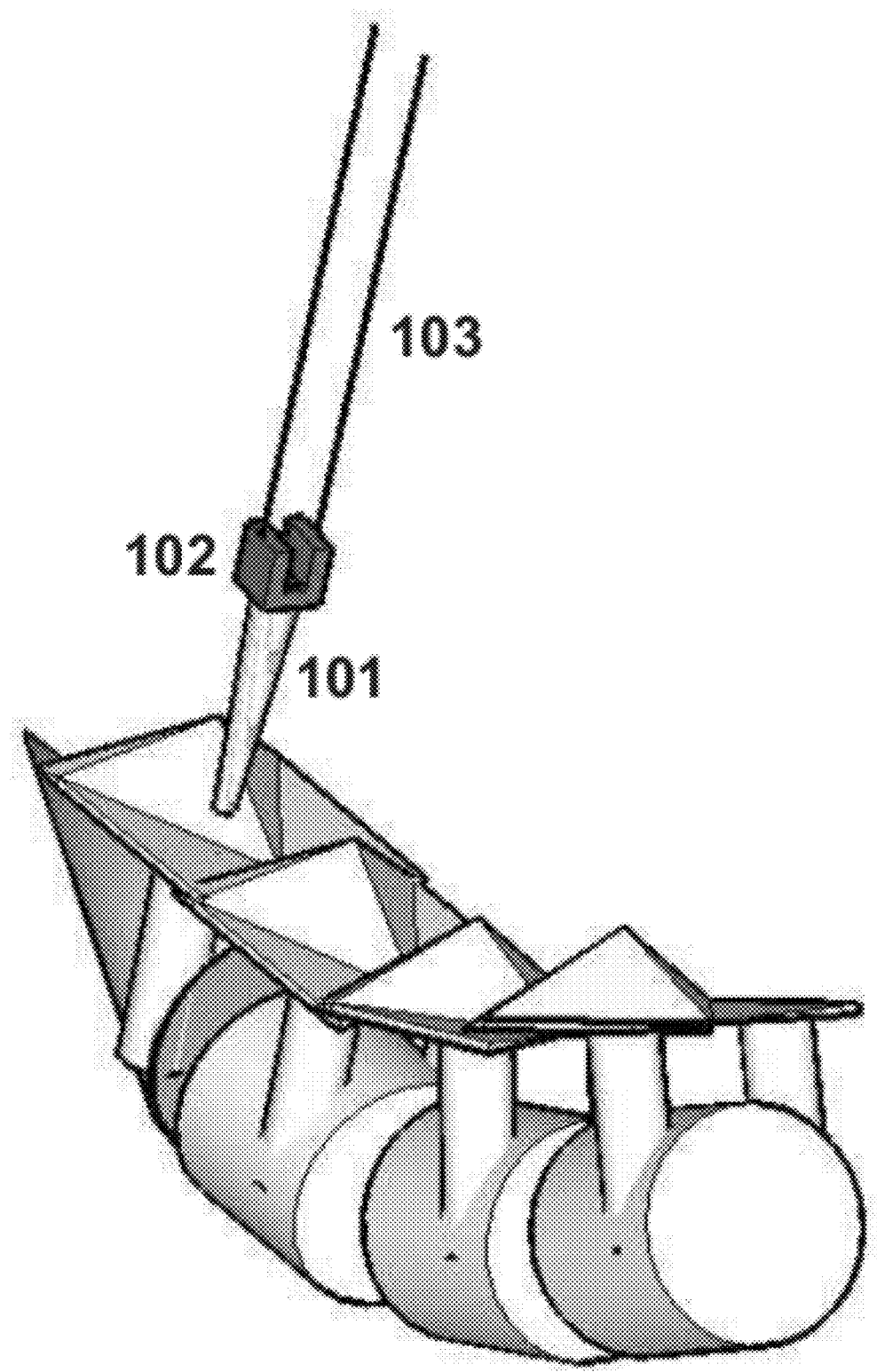
FIG. 12 shows the pedicle screw being inserted into the pedicle portion of a vertebra on the anatomical right side of the central lamina.

The steps for the placement of the pedicle screws and rods for a "Microfusion" approach are as follows. First, using fluoroscopy or stereotactic guidance, a single small skin incision 1-4 cm lateral to a midline that will accommodate all pedicle screws is localized. Next, using either a percutaneous Jamshedi/Kirschner-guidance element (K-guidance element) approach, a Wiltse muscle splitting approach, or tube system, the pedicle screws are placed (see FIG. 12). The pedicle screw inserter may have loop attachments that hold the side guidance elements of the pedicle screw during placement. Or, the insertion tool or device that positions the pedicle screw may have protrusions (or slots/grooves) that mate with corresponding slots/grooves (or protrusions) on the upwardly directed extended guidance elements (similar to how the cap is guided in FIG. 4). Once the pedicle screw is placed, the insertion tool or device needs to be removed to make room for the placement of the other screw(s), the rod, and optionally, a separate locking assembly.

Figure 13:
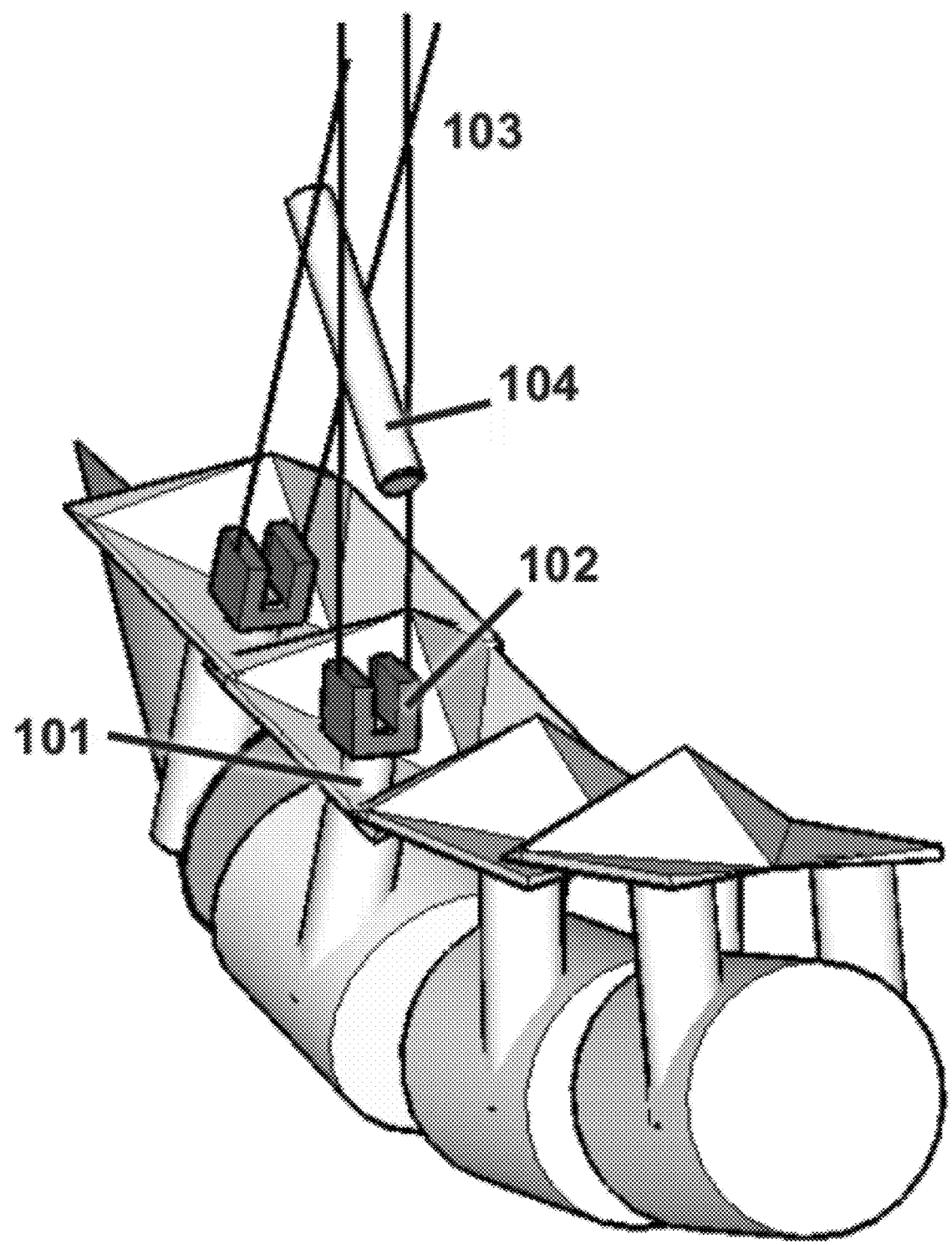
FIG. 13 shows two pedicle screws in position on two adjacent vertebrae on one side of a vertebral column, with the screw shafts buried within the vertebral bones and the U-shaped screw heads protruding from the pedicles' surfaces. Also shown is a rod being guided down (at an angle) to the screw heads, between each of two sets of two guidance elements, one for each screw.

After each pedicle screw is placed, the side guidance elements are pushed to the side(s) of the incision to make room so that the other screws can be placed around or between the guidance elements already in place. Typically it is preferable to insert additional screws in between the guidance elements of the first screws for cases where pairs of wires, blades, or tabs are used. After all screws are placed, a screw head turner is inserted and guided down to the screw heads along each pair of guidance elements to align the heads of the screws in preparation for receiving the rods (see aligned screw heads in FIG. 13).

Figure 14:
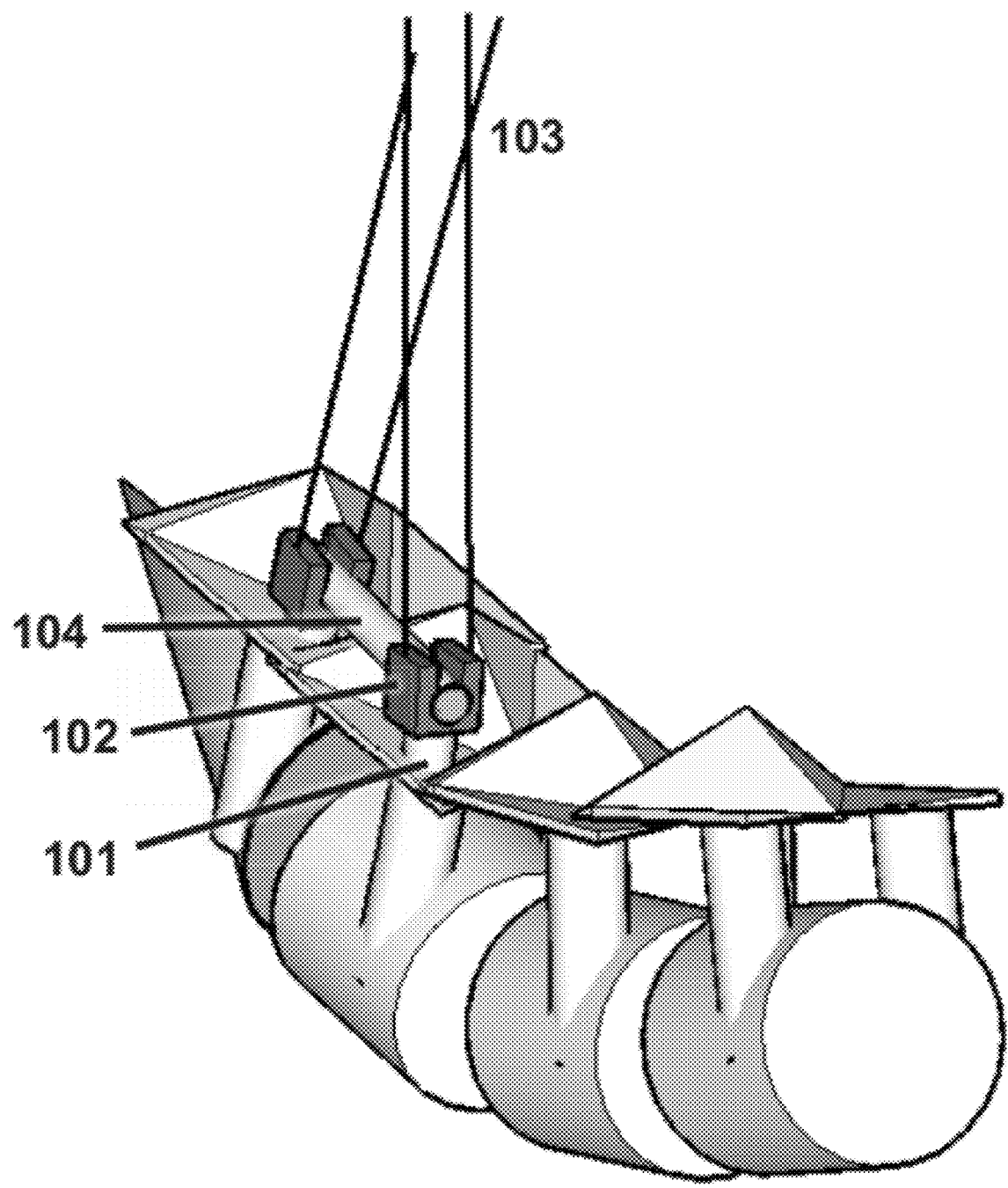
FIG. 14 shows the rod in a proper final position fully inserted within the screw heads of the pedicle screws in adjacent vertebrae along one side of a vertebral column for a partial (half-finished, the other side having yet to be stabilized) one-level stabilization. The locking assemblies are not shown here but may also be guided by the guidance elements down to the screw heads.
Figure 15:
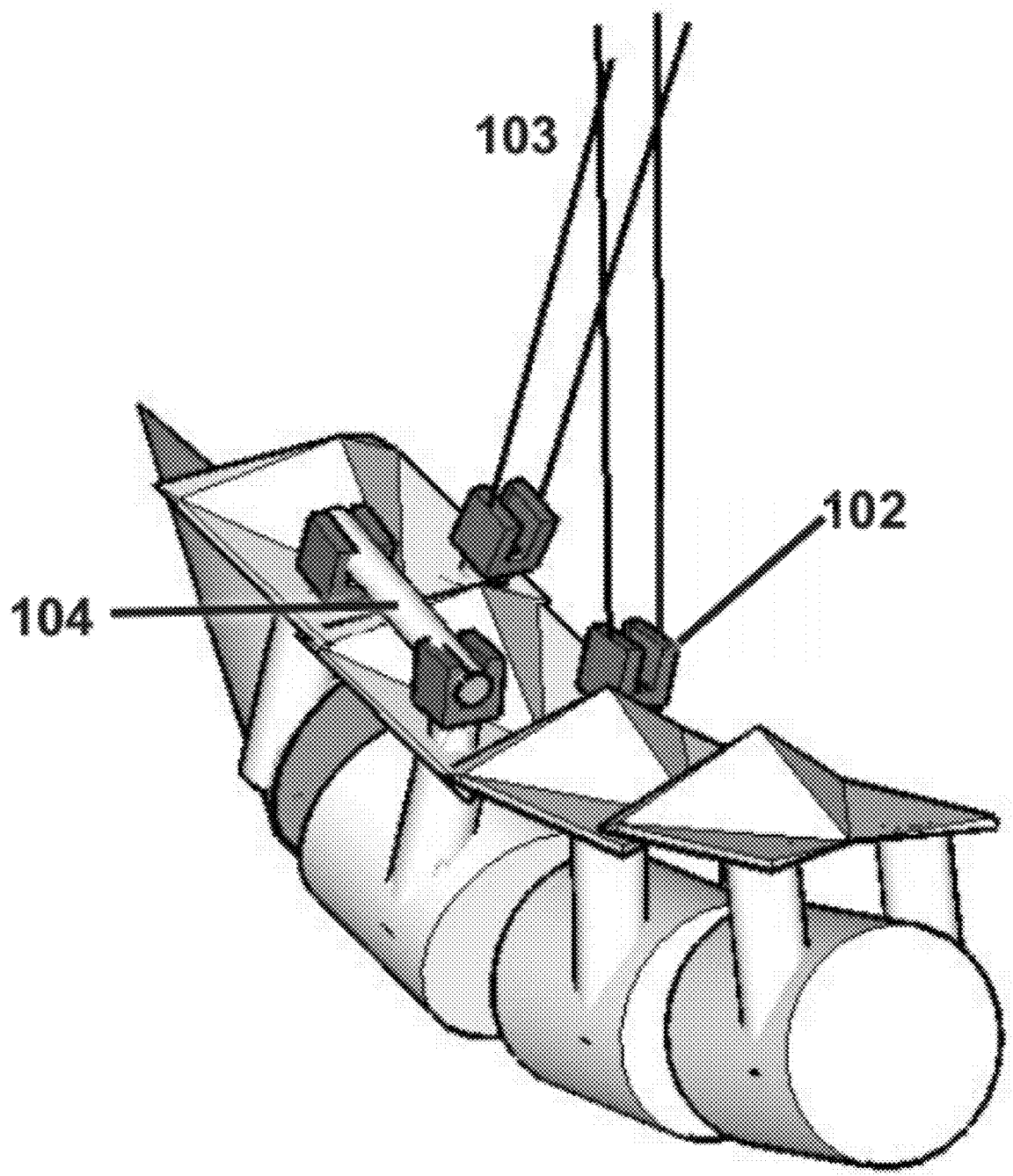
FIG. 15 shows the guidance elements (for guiding the rods, locking assemblies, etc.) having been detached from the screw heads of the pedicle screws along the anatomical right side of the vertebral column, but with the same screw head-guidance element system still in place on the anatomical left side of the vertebral column ready to accept and guide a rod down to the pedicle screws. The locking assemblies are not shown.
Figure 16:
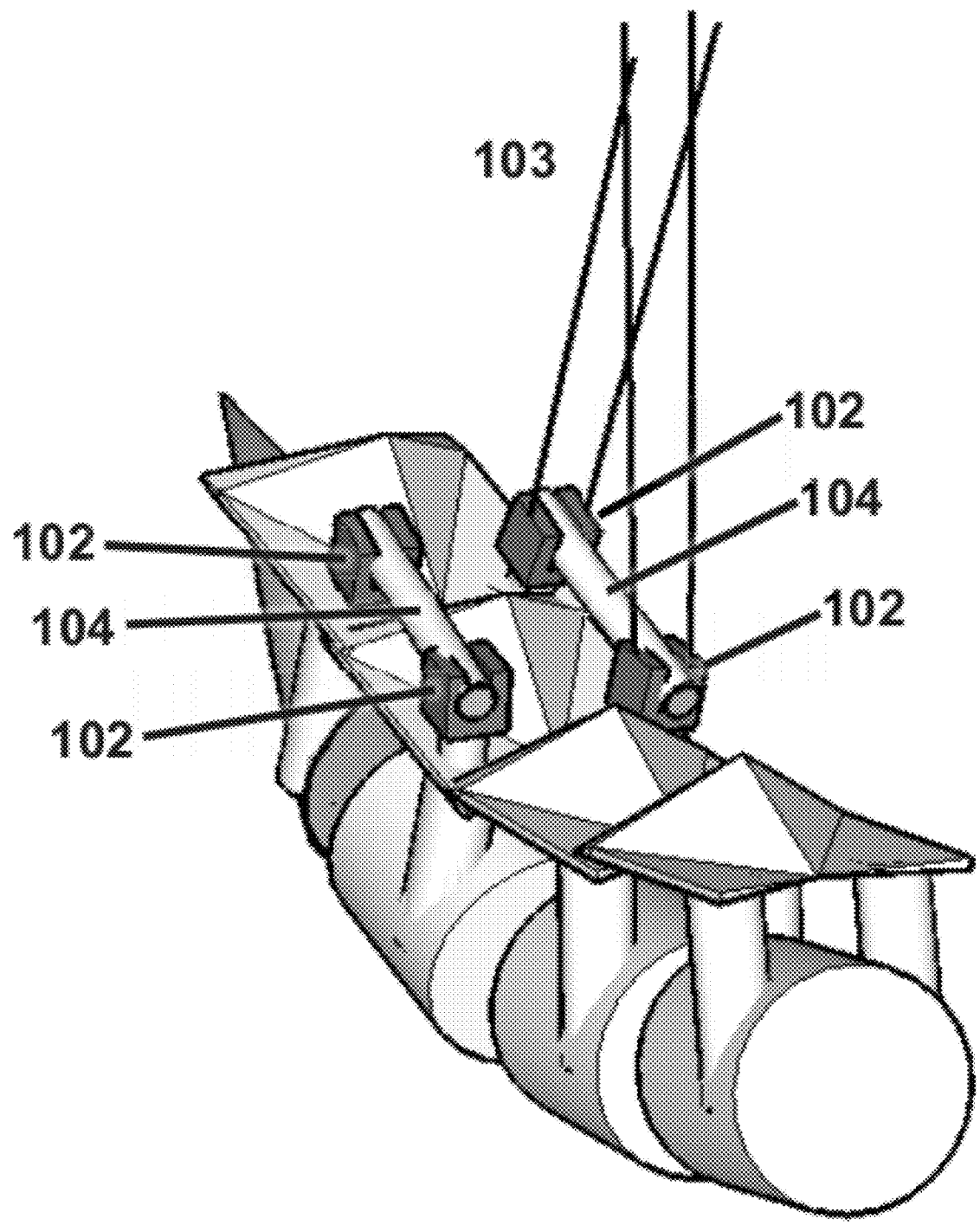
FIG. 16 shows the second rod in place within the screw heads on the anatomical left side pedicles of the vertebral column, with the detachable screw head guidance elements remaining on only the anatomical left side.

With the screw heads aligned, the side guidance elements are split between the medial and lateral sides. Then a rod is slid in between the medial and lateral guidance elements into the screw heads. Preferably, the rod should be sized and bent before insertion. Markers on the guidance elements at predefined distances from the tip of the guidance elements can help guide the surgeon in correctly sizing and bending the rod. Guidance elements coming out of a single incision are similar to light rays that have been focused by a convex lens. These light rays converge at a point and then create a mirror virtual image on the other side of the focal point. This same concept can be used to create a mirror image of the rod to guide the sizing and bending of the rod to accurately fit into the screw heads. (See FIG. 14). The depth of each guidance element relative to the intersection point near the skin incision is reflected outwardly on that same guidance element and equal distance away from the intersection point. By connecting the reflected points on the guidance elements proximal to the intersection point, a virtual image of the curvature and length of the rod is accurately estimated. The rod is then lowered through the guidance elements by one or a combination of mechanisms including retention threads, rod holders that are guided by the guidance elements, and rod wires. After each end of the rod is properly positioned within a screw head, locking nuts or caps are screwed on the screw heads to secure it in place. Or, a compressor that is guided by the guidance elements is used to compress pedicle screws on adjacent levels and then final tightening can be done during compression. Other instruments can also guided by the guidance elements, such as to compress, distract, or move one vertebra relative to another (e.g., for spondyloisthesis or scoliosis). The guidance elements are then removed by any means including cutting, twisting, wagging, burning, radiating, dissolving, unscrewing, etc. (see FIG. 15 and FIG. 16, left side). Once the screws and rods in all vertebrae to-be-fused along one side of the vertebral column are stabilized, the contralateral side can be similarly stabilized if indicated (see FIG. 15 with one rod, preparing for the second, and FIG. 16 with two rods placed).

Embodiments of the present invention can be used to dynamically stabilize or fuse vertebrae while at the same time removing a defective intervertebral disc and inserting a spacer in its place. The spacer may include bone graft material or bone inducing material incorporated therein to encourage healing. Example bone inducing materials include bone morphogenetic protein, tricalcium phosphate, hydroxyapatite, and collagen.

The various elements (guidance elements, screws, screw heads, rods, retention threads, locking assemblies, etc.) may be provided in a range of sizes, shapes, strengths, flexibilities, and other physical characteristics to best accommodate individual patients and particular applications. Other embodiments include combining two or more of the elements mentioned so that the combined elements can be inserted together instead of one at a time. For instance a locking assembly that is attached to a rod or that is placed downwards together with a rod will save one separate step of placing the locking mechanism after the rod is placed. Similarly, a rod that is attached to the second screw head vertically by a hinge can then be swung down into the guidance element and screw head of the first screw after the second screw has been placed. A rod wire will further ensure that the tail end of the rod stays within the guidance element of the first screw. This combination saves the separate step of placing the rod into the incision.

While the illustrated guiding elements and accompanying disclosure discuss the delivery of a rod via the guiding elements, the guiding elements can also be used to deliver guiding tools designed to compress, reduce a spondylolisthesis, and/or provide counter-torque when locking the a rod member in place. In addition, various other tools can be provided to assist in stabilization, such as dynamic stabilization.

FIGS. 23A-23C show how for a three level stabilization the rod 104 can be guided down by the guidance elements on a first screw head while the guidance elements on a second and third screw head are splayed outward or bent to open the receiving or encatchment area for the rod to easily enter. In the conventional case of pedicle screw towers, the rod had to be precisely inserted through the small opening within each rigid tower. Embodiments of the present invention overcomes this difficulty. It will be appreciated with multi-level procedures, a single incision may be used for delivery of all of the screws, implants or instruments. Alternatively, multiple incisions may be used as desired, with one or more of the incisions accommodating screws, implants and instruments for multiple vertebra. For example, as shown in FIGS. 25A-25C, the lowest two levels (L5 and S1) share a single incision but the upper two levels (L3 and L4) have separate incisions. Rod retention threads only span the inferior half of the rod and only capture the guidance elements of the lower two vertebrae (L5 and S1). The superior end of the rod is then pushed through the guidance elements of the upper two vertebrae (middle figure). Or, a thread that is attached to the superior end of the rod can be used to pull the rod through the guidance elements of the upper two vertebrae. This thread can be introduced in between each set of guidance elements by a large suture needle that is inserted in one incision and is pulled out of the next incision in between the guidance elements.

Figures 24A, 24B, 24C:
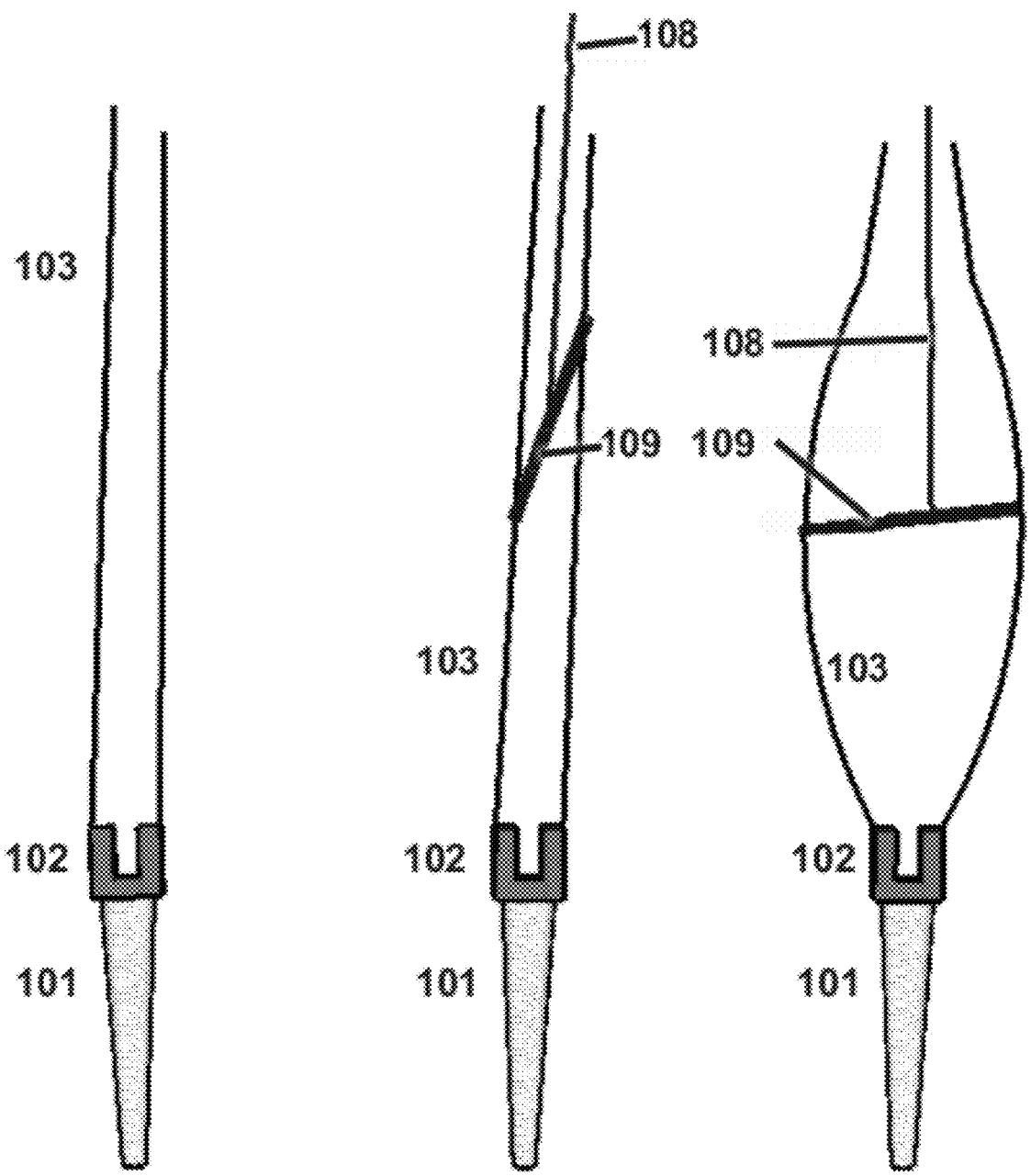
FIGS. 24A-24C show an embodiment using a tool to separate the guidance elements deep below the skin surface. In this manner, the skin incision remains small. A "T"-shaped tool with a hinged "T" portion is attached to the guidance elements and slid partially down towards the screw head. As the hinged "T" is opened, the middle section of the guidance elements is separated. This opened window allows the rod to be tunneled in between the guidance elements, especially in instances where the rod and pedicle screw heads are inserted through separate incisions.

As shown in FIGS. 24A-24C a refined T-shape tool 108/109 may be used to separate the guidance elements 103. This gesture prevents them from becoming tangled (or disentangles them) and opens the space in between them such that a rod can be passed through it to enter the screw head. The horizontal arms 109 of the "T" extend outward perpendicular to the longitudinal insertion axis 108. These arms 109 may be aligned parallel against the main longitudinal body during insertion and removal. They may also be inside the main body and deployed from within via telescopic extension or a spring-like mechanism. The end of each horizontal arm 109 may be U-shaped, V-shaped, or circular such that a guidance element 103 can be retained within it. If the ends are U-shaped or V-shaped the T-shaped tool 108/109 can be disconnected from the guidance element 103 easily after spacing by collapsing the arms to realign against the longitudinal insertion axis 108 or to collapse into the main body. If the ends are a closed loop shape such that the guidance elements 103 are fed through them and trapped within them, the loops should be configured to open to release them (like a jewelry clasp) after the tool 108/109 has performed its function.

Figure 31B:
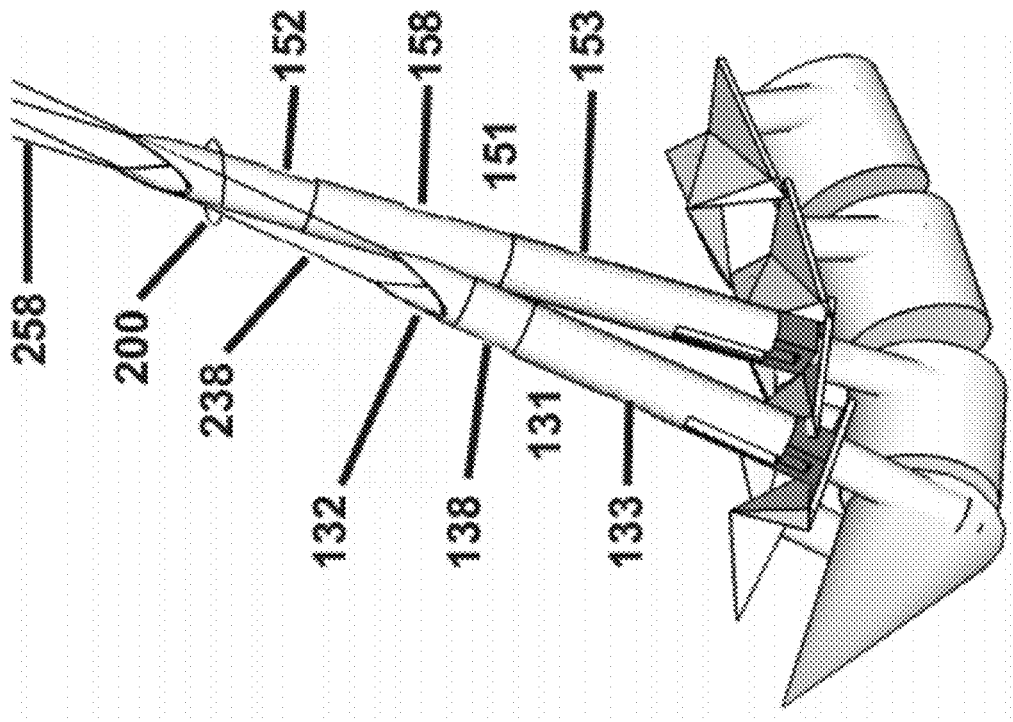
FIGS. 31A and 31B show various arrangements of guidance elements comprising telescoping tubes closer to the pedicle and connected to wires at the skin level incision. The telescoping tubes go from wider to narrower along a trajectory extending from the pedicle of the vertebra to the incision.
Figure 31A:
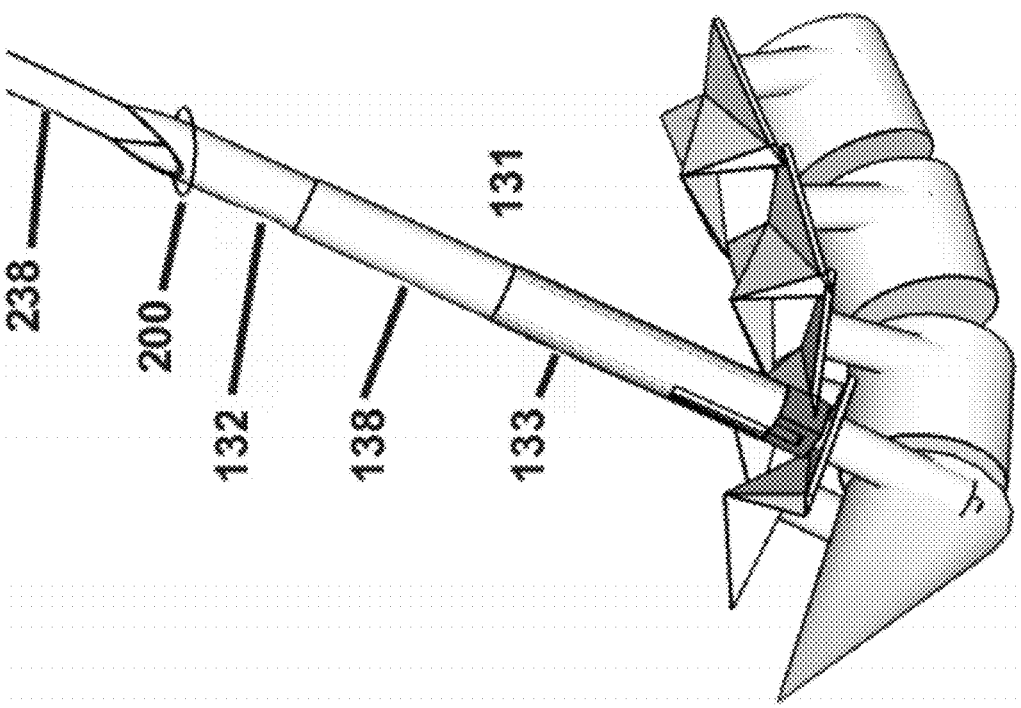

FIGS. 31A and 31B illustrate one or more assemblies of telescoping guiding elements in use with vertebrae according to some embodiments. FIG. 31A illustrates an assembly comprising a plurality of telescopic guiding elements 131. The plurality of telescopic guiding elements 131 includes an upper guiding element 132, a lower guiding element 133 and a middle guiding element 138. The lower guiding element 133 of the plurality of telescoping guiding elements 131 is positioned closest to the pedicle of a vertebra and is wider than the upper guiding element 132, which is positioned closer to the incision 200. The incision 200 is at skin level. The telescoping guiding elements may progress from wider near the vertebrae to narrower near the skin. For example, in some embodiments, the lower guiding element 133 includes an internal width or diameter that is greater than the middle guiding element 138 or upper guiding element 133, thereby allowing the middle guiding element 138 or upper guiding element 133 to "telescope" within the lower guiding element 133. The telescoping feature allows for adjustment of the height of the assembly of telescopic guiding elements, which advantageously results in less crowding closer to the incision 200 in order that more guidance elements from a greater number of vertebrae can fit through a single incision. In some embodiments, at the skin level incision 200, guidance elements from different vertebrae all converge on one another. Away from the skin level incision 200 and closer to the vertebrae the guidance elements diverge.

As shown in FIG. 31A, the plurality of telescoping guiding elements 131 can comprise a plurality of cylindrical tubes that can "telescope" (e.g., slide into and/or relative to one another) and assume various heights as an assembly. In some embodiments, each of the plurality of cylindrical tubes can move along a longitudinal axis relative to one another. In other embodiments, the plurality of telescoping guiding elements 131 can comprise other shapes as well, including non-cylindrical elements. In the illustrated embodiment, the plurality of telescopic guiding elements 131 include three different tubular members; however, different embodiments can include any number of telescoping members. For example, a plurality of telescoping guiding elements 131 can include only an upper guiding element and a lower guiding element, or in other cases, more than three telescoping guiding members. In addition, each of the telescoping guiding elements can have various internal widths or diameters, such that they can each be inserted individually through the single incision. In some embodiments, one or more tubes have a diameter of between about 14 mm and 25 mm and are capable of fitting through an incision of between about 14 mm and 25 mm. In one embodiment, edges of the telescopic guiding elements may be chamfered or U-shaped 134 as shown for the upper edge of the upper telescopic guiding element 132.

As shown in FIG. 31A, one or more extension members 238 can be operably connected to the telescoping guiding elements 131. In the illustrated embodiment, the extension members 238 comprise wires or threads operably attached to the upper guiding element 132. In the event that the plurality of telescoping guiding elements assume a reduced height (e.g., as shown by the plurality of telescoping guiding elements 131 in FIG. 31B positioned below a skin incision), the extension members 238 advantageously extend through and outside the incision and allow a user to properly identify the location the plurality of telescoping guiding elements of reduced height. In some embodiments, the extension members 238 can also advantageously serve as guiding elements themselves, such that rod members or other implants can be guided toward the plurality of telescoping guiding elements.

FIG. 31B illustrates the use of a first assembly comprising a plurality of telescopic guiding elements 131 and a second assembly comprising a plurality of telescopic guiding elements 151. The first plurality of telescopic guiding elements 131 includes an upper guiding element 132, a middle guiding element 138, and a lower guiding element 133. Extension members 238 in the form of wires extend from the upper guiding element 132. Similarly, the second plurality of telescopic guiding elements 151 includes an upper guiding element 152, a middle guiding element 158 and a lower guiding element 153. Extension members 258 in the form of wires extend from the upper guiding element 152. As shown in FIG. 31B, after the pedicle screw attached to the telescoping guiding elements 131 is delivered into a vertebra, the height of the telescoping guiding elements 131 can be reduced so that the upper guiding element 132 is positioned below the skin incision 200, but the wires 238 extend out of the incision 200. This provides room for the pedicle screw attached to the second telescoping guiding elements 151 to be delivered into the vertebra. As shown in FIG. 31B, the second plurality of telescopic guiding elements 151 can advantageously be inserted into a desired position via the same single incision 200, thereby reducing the amount of trauma to a patient compared to other guiding systems that require multiple or larger incisions.

Figure 32:
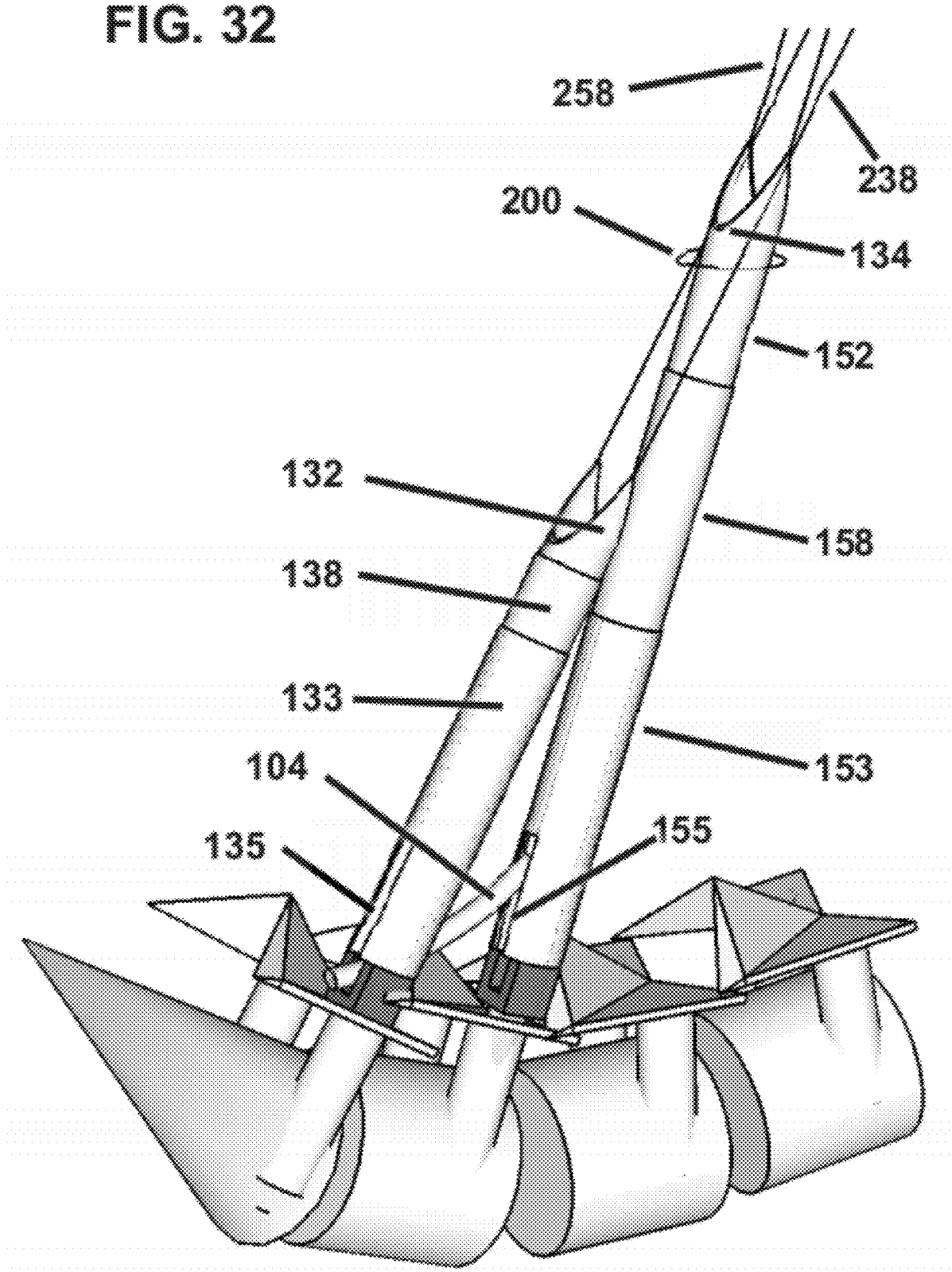
FIG. 32 shows a rod inserted through a first plurality of telescopic tubes being guided out of a first window in a first lowermost tube and into a second window in a second lowermost tube of a second plurality of telescopic tubes.
Figure 33:
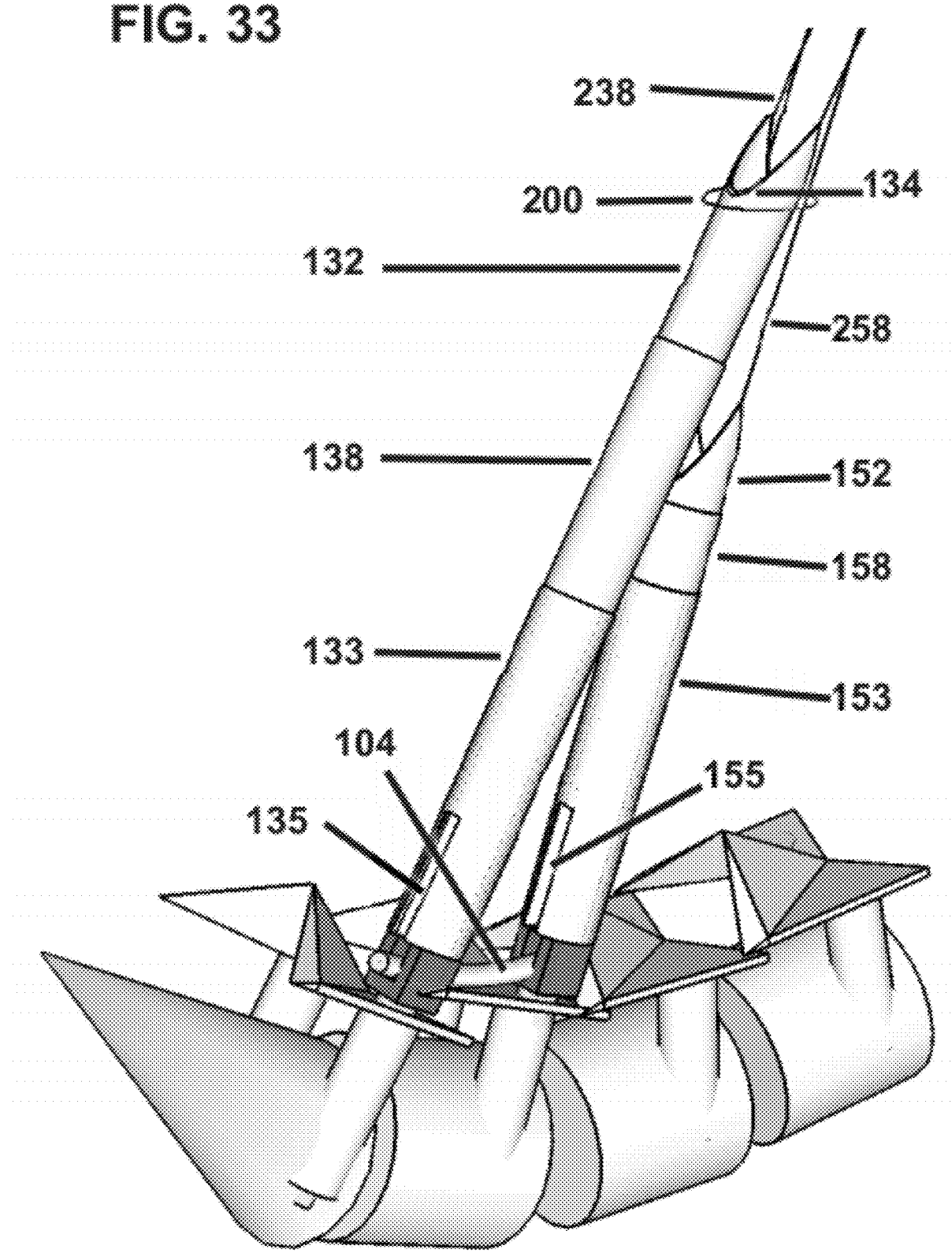
FIG. 33 shows the rod after it has been lowered through the first and second windows of the first and second lowermost tubes, respectively, into the first and second screw caps of first and second pedicle screws of first and second vertebrae.

FIGS. 32 and 33 illustrate the delivery of a spinal implant in the form of a rod using telescopic guiding elements as discussed above. As shown in FIGS. 32 and 33, with the first set of telescoping guiding elements 131 still reduced in height and the second set of telescoping guiding elements 151 extending through the incision 200, a rod 104 or other implant can be inserted through the same singular incision as the guidance elements. The rod 104 can be inserted through a center of the plurality of telescopic guiding elements 151. The rod 104 enters through an opening in an upper guiding element 152 as part of a second guidance element assembly attached to a second vertebra and is directed downwards to a lower guiding element 153 as part of the same first guidance element assembly. The lower guiding element 153 has a window 155 therein configured to permit passage of the rod 104 therethrough. A first end of the rod 104 is passed through the window 155 of the lower guiding element 153 of the second assembly of guidance elements and maneuvered until it enters a window 135 of a lower telescopic guidance element 133 of a first assembly of guidance elements 131 attached to a first vertebra. The first end of the rod 104 can be guided down the plurality of telescopic guiding elements 151 until it enters a channel for receiving it in a first screw head of a first screw in the first vertebra (as shown in FIG. 32). Then the other (second) end of the rod 104 is guided down the window 155 until it enters a channel for receiving it in a second screw head of a second screw in the second vertebra (as shown in FIG. 33). As shown in FIG. 33, at this point the height of the second plurality of telescoping guiding elements 151 may be reduced such that the uppermost element 152 is below the skin incision, with the wires 258 extending through the incision. Using the wires 238, the height of the first plurality of telescoping guiding elements 131 may be increased to again extend through the skin incision. This first plurality of telescoping guiding elements may then be used to deliver instruments therethrough, for example to delivery a locking assembly to the pedicle screw. Further extensions and reductions in the height of the telescoping guiding elements may be employed as desired by the surgeon in order to perform appropriate procedures on the patient.

While the illustrated embodiments in FIGS. 32 and 33 depict the guidance of a rod implant down the telescoping guiding elements, the telescoping guiding elements can also help guide non-rod implants, as well as locking devices (e.g., cap members) and tools for compression, distraction, and various other spinal procedures.

Methods of spinal stabilization using telescoping guiding elements as shown in FIGS. 31A-33 will now be described. Initially, a single incision 200 is formed in a patient. In some embodiments, the incision can be between 0.5 cm and 4 cm, more preferably 3 cm or less or 2 cm or less. A first screw is provided and can be pre-attached via its screw head to a distal end of an assembly of telescoping guiding elements 131 prior to insertion into the patient. A second screw is also provided and can be pre-attached via its screw head to a distal end of an assembly of telescoping guiding element 151 prior to insertion into the patient. Each assembly of telescoping guiding elements 131 and 151 can include an upper, middle and lower guiding element, wherein the upper and middle guiding elements can "telescope" or slide relative to the lower guiding element to adjust the overall height of the assemblies. In addition, each assembly can include one or more extension members 238, 258 attached, for example, to the upper guiding elements 132 and 152, respectively.

After forming the incision, the first screw and its accompanying assembly of telescoping guiding elements 131 can be positioned through the incision. The first screw can be placed in a desirable location adjacent to the vertebrae. Using a screw driver or other tool through the assembly of telescoping guiding elements 131, the first screw can be fixed to a first vertebra. At this point, the assembly of telescoping guiding elements 131 extend from the first screw through the incision 200, as shown in FIG. 31A.

To allow for the insertion of the second screw and its accompanying assembly of telescoping guiding elements 151 through the same incision 200, the assembly of telescoping guiding elements 131 can be reduced in height so that the upper guiding element 132 is below the incision 200. Contact is maintained with the upper guiding element 132 by using one or more extension members 238 that are attached to the upper guiding element 132. The extension members 238 can comprise one or more wires, and extend from the upper guiding element 132 and through the incision 200. Using the extension members 238, a surgeon or other user can easily locate the position of the reduced height assembly of telescoping guiding element 131.

With the height of the assembly of telescoping guiding elements 131 reduced such that the upper guiding element 132 is below the incision 200, the second screw and its accompanying assembly can be placed through the same incision 200. The second screw is fixed to a second vertebra (e.g., using a screw driver). At this point, the accompanying assembly of telescoping guiding elements 152 extends from the second screw to outside of the incision 200. Like the first assembly, the second assembly of telescoping guiding elements 151 can also include extension members 258 attached to an upper guiding element 152 to thereby maintain contact with the second assembly outside of the incision. As shown in FIG. 31B, the extension members 258 of the second assembly can criss-cross or intersect the first assembly of telescoping guiding elements 131 and/or its extension members 238 at or near the incision 200.

If desired, additional assemblies of telescoping guiding elements can be introduced through the same incision. For example, the heights of both the first assembly of guidance elements 131 and the second assembly of guidance elements 151 can be reduced below an incision to make way for a third assembly of guidance elements via a similar procedure.

With the first assembly of telescoping guiding elements 131 and second assembly of telescoping guiding elements 151 in place through the same incision, a rod member can be delivered. With reference to FIGS. 31B and 31C, a rod member 104 can be delivered through the interior of the second assembly of telescoping guiding elements 151. The rod is delivered such that it is turned and angled through a window 155 formed in the second assembly (as shown in FIG. 31C). One end of the rod can then be optionally delivered through the window 135 formed in the first assembly. At this point, one end of the rod can be secured into the seat of the second screw head, while the other end of the rod can be secured into the seat of the first screw head. Locking elements (e.g., cap screws) can then be delivered through each of the telescoping tubes to secure the rod into the seats of the first screw and second screw. If needed, the heights of each of the assemblies of telescoping guiding elements can be adjusted in order to expose an upper guidance element of each of the assemblies above the incision 200 in order to insert the locking assembly.

Once the rod member 104 is in place, the assemblies of telescoping guiding elements 131, 151 can be decoupled and removed from their respective screws. Instruments can be inserted through the telescoping guiding elements to actuate a release mechanism to release the telescoping guiding elements from the screws. The assemblies of telescoping guiding elements 131, 151 can be then removed from out of the patient and the incision can be closed. The patient can be left to heal. Advantageously, as the procedure only involved a single, relatively small incision, the patient experienced less trauma and can expect a faster healing time compared to if other conventional methods had been used.

FIGS. 34A to 34D illustrate embodiments of a hybrid system utilizing at least one set of non-cylindrical telescoping guiding elements. As shown in FIG. 34A, the telescoping guiding element 300 need not be cylindrical but can have other shapes. The telescoping guiding element 300 shown in FIG. 34A includes substantially rectangular arms or blades 315 having squared edges that provide a channel or pathway for the delivery of a rod or other spinal implant therethrough (as shown in FIG. 34D). The guiding element 300 may include wires 238 as described above. In some embodiments, the height of one or more blades 315 can be adjusted by moving one part of a blade 315 relative to another. For example, as shown in FIG. 34D, the blade 315 can be adjusted by moving component 315a relative to 315b, thereby shortening or lengthening the height of the blade 315. Preferably there is a friction mechanism that keeps component 315a fixed at a specific position relative to 315b. The friction mechanism can be augmented by flexible teeth that further 315a from sliding spontaneously relative to 315b. The interior of blade component 315a is slightly larger than the interior of blade component 315b, thereby allowing relative sliding between the two members. The telescoping guiding element 300 further includes one or more indentations or grooves 304 therein that provides a channel or pathway along a length thereof to receive a protrusion of a locking assembly, tool, or other element in order to guide it down to a delivered rod.

FIGS. 34B to 34D illustrate the use of telescoping guiding element 300 including substantially rectangular blades in combination with a non-telescoping guiding element 310. It will be appreciated that in other embodiments both sets of guiding elements may be telescoping. In FIG. 34B, a telescoping guiding element 300 can be reduced in height to have short blades 315 and extension members 238 can be used in conjunction to control or extend the length of the telescoping guiding element. Guiding element 310 may comprise a conventional set of long blades 311 to deliver a rod or other spinal implant to a desired position within a channel in a screw head. Thus, in one embodiment, the telescoping guiding elements may first be delivered with a first screw, and then reduced in height to allow delivery of a second screw having a conventional guiding element.

In FIG. 34C, the telescoping guiding elements 300 can be extended using wires 238 to criss-cross or overlap with the long blades 311. As shown in FIG. 34C, a rod 304 can be guided and delivered to the screws using the blades 315a, 315b and 311. With the blades 315a and 315b extended, as shown in FIG. 34D, a screw cap locking assembly 119 (as described above) can be delivered to lock the rod 104.

The telescoping guiding elements can have any shape or configuration and still be within the spirit and scope of the present invention. They may be cylindrical as shown in FIG. 31A or have straight edges as shown in FIG. 34A. The telescoping guiding elements can also have any number of segments or portions that collectively form the telescoping assembly or system and still be within the spirit and scope of the present invention. As shown in FIG. 31A-33, at least three separate portions of cylindrical telescoping tubes are visible. As shown in FIG. 34D, at least two separate portions (315a and 315b) of substantially rectangular telescoping arms are visible.

Additionally, there are several different variations of the telescoping mechanism all contemplated within the spirit and scope of the present invention. FIGS. 32-33 and 34B-34D show the narrowing of the distance between one telescoping guiding element from another telescoping guiding element, as the telescoping guiding elements come closer to the incision relative to their positions near the vertebrae.

In addition, within their individual assemblies, the telescoping guiding elements can be configured such that guiding components closer to the incision have a smaller width or diameter relative to guiding components closer to the vertebrae. For example, with respect to FIG. 31A, the upper guiding element 132 can have a smaller width or diameter relative to the lower guiding element 133, such that the upper guiding element 132 can be slid into and out of the lower guiding element 133. Alternatively, the telescoping guiding elements can be configured such that guiding components closer to the vertebrae can have a smaller width or diameter relative to guiding components closer to the vertebrae. For example, with respect to FIG. 34D, the upper component 315b of the blade can have slightly larger dimensions relative to lower component 315a of the blade, such that the upper component 315b can be slid over and around the lower component 315a.

In the illustrated embodiment in FIG. 34D, the upper telescoping component 315a closer to an incision rides along the outside of the lower telescoping component 315b closer to the vertebrae. That is, in some embodiments, telescoping guiding elements closer to the incision have a larger dimensions (e.g., widths and diameters) than telescoping guiding elements closer to the vertebrae. In some embodiments, the upper telescoping component 315b can be cut-out to receive the lower telescoping component 315a closer to the vertebrae. The lower telescoping component 315a closer to the vertebrae can be solid filled or hollow (cut-out), and is configured to fit into the upper telescoping component 315b thereabove.

Figures 35A, 35B, 35C:
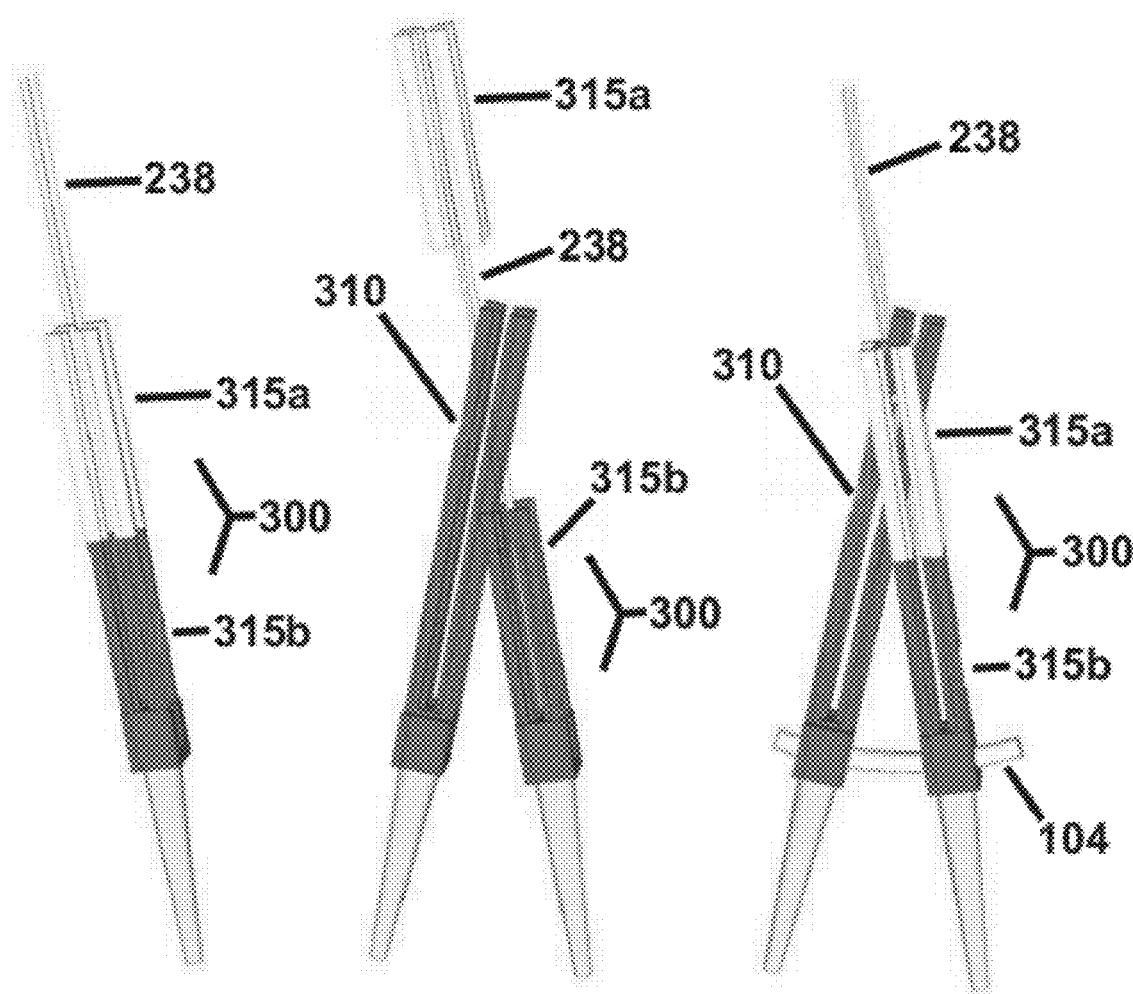
FIGS. 35A-35C show another embodiment of guiding elements wherein an uppermost guiding element may be removed and reinserted through the skin incision.

FIGS. 35A to 35C show another embodiment of guiding elements where at least some of the guiding elements are removable and reinsertable into the patient. The illustrated embodiment presents a "hybrid" system of a non-telescoping guiding element 310 and a novel guiding element 300 with removable and reinsertable components. As shown in FIG. 35A, guiding element 300 includes upper guiding component 315*a* and lower guiding component 315*b*. While in one embodiment these components may be telescoping, in another embodiment they may not be. The screw with these components attached are delivered into a first vertebra. Then, as shown in FIG. 35B, the upper component 315*a* can be removed from the incision, leaving the lower component 315*a* behind, but attached with wires 238 extending through the incision 200. The wires may be attached to the lowermost guide component 315*b*, or alternatively may be attached to the screw as well so that component 315*b* may also be removable over the wires. A screw attached to a conventional guiding element such as blades 310 may be delivered into a second vertebra, criss-crossing with the wires 238. As shown in FIG. 35C, the upper component 315*a* can be reattached to the lower component 315*b* as desired, to deliver rod 104 or other implants or instruments to the spinal location. In one embodiment, there may be multiple (e.g., two or more) removable guide components that are slidable along the wire or wires 238, in order to adjust the height of the assembly as desired. Although FIGS. 35A-35C only illustrate one guide element having removable guide components, it will be appreciated that there may be multiple such assemblies, one per screw.

Figure 36A:
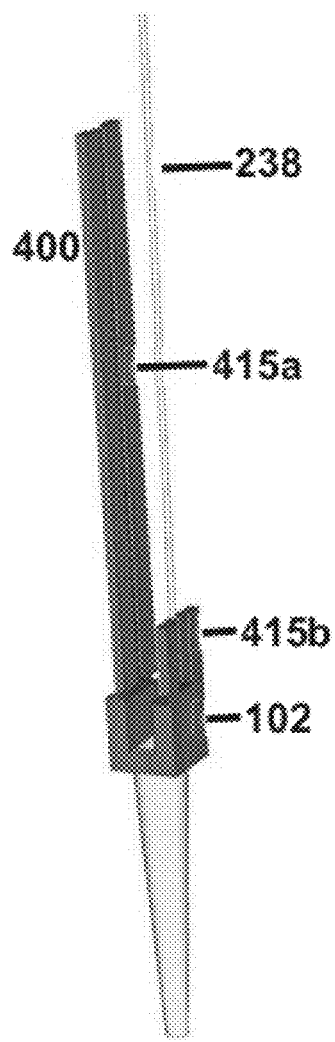
FIGS. 36A-36C show a hybrid embodiment with extended blades or arms on one side of a slot configured to receive a rod and much shorter blades or arms on the other side. Wires attached to the short blade or arm help keep muscle and fascia from interfering with the placement of the rod and locking assembly. This configuration can alternate from one vertebra to the next, as shown, with the longer and shorter blades changing sides.
Figure 36B:
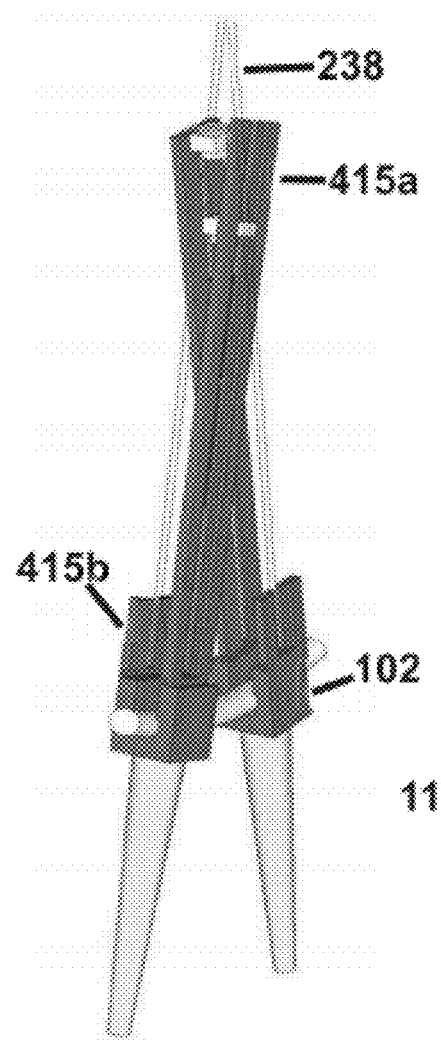
Figure 36C:
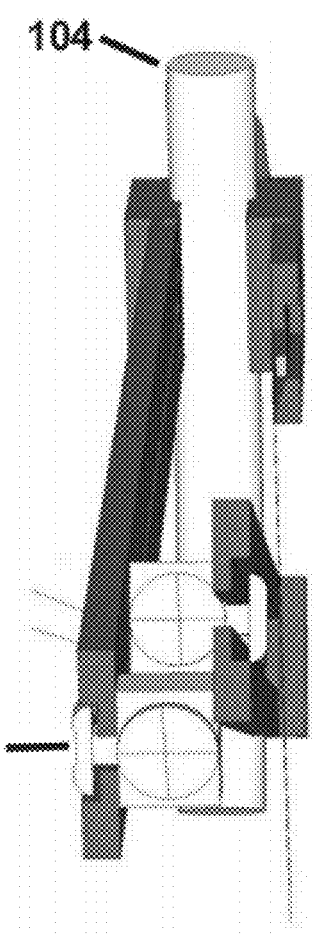

FIGS. 36A to 36C show a hybrid system 400 for rod and implant delivery combining longer extended blades or arms 415*a* with shorter blades, arms or tower 415*b*. The shorter blades 415*b* can be attached to one or more guidance wires 238. As shown in FIG. 36A, the longer extended blades 415*a* and/or the shorter blades 415*b* extend from the top of a screw head 102. In other words, one side of a screw head 102 or one side of a channel configured to receive a rod within the screw head 102 has the longer extended blades 415*a* and the other side has shorter blades 415*b*. Both the longer blades 415*a* and shorter blades 415*b* are used to guide a rod 104 into position into a desired position in the seat of a screw head 102 of a screw that has been placed in the pedicle portion of a vertebra. In some embodiments, the longer extended blades 415*a* can be telescopingly shortened, while the shorter blades 415*b* can be telescopingly extended. While in the illustrated embodiment in FIGS. 36A-36C the guidance elements are not telescoping, in other embodiments, telescoping features can also be included. As shown in FIG. 36B, a hybrid assembly comprising a long blade 415*a* and a short blade 415*b* with wire 238 attached to a screw head can criss-cross with a similar assembly. The use of a wire 238 as part of the hybrid assembly provides flexibility such that the second assembly with screw head can pass through the passageway created by the wire 238 and long blade 415*a* in the first assembly. In one embodiment, the long blades or short blades may be similar in shape to the guide tabs or the sleeves described in U.S. Publication No. 2009-0234392A1 and U.S. Pat. No. 7,758,584, the entirety of each of which is hereby incorporated by reference.

In some embodiments, the longer extended blades or arms 415*a* may reach all the way to and through the skin level incision or may be connected to wires that go through the incision. The shorter blades, arms, or towers 415*b* do not extend to and through the skin level incision. By using shorter blades 415*b* in the hybrid system 400, there is less crowding around and at the skin level incision, thereby allowing room for additional longer extended blades attached to multiple vertebrae to fit through the same incision. As shown in FIG. 36A, the side on which the longer and shorter blades are placed can alternate from one pedicle screw or vertebra to the next, such as described in the above referenced U.S. Publication No. 2009-0234392A1 and U.S. Pat. No. 7,758,584. This may help to provide greater stability overall for a multiple level stabilization or fusion. For example, on a first lower vertebra the longer extended blades 415*a* may be placed on the lateral side (with shorter blades 415*b* on the medial side) while for a second higher vertebra the longer extended blades 415*a* are on the medial side (with shorter blades 415*b* on the lateral side).

In addition to the hybrid systems discussed above, additional hybrid systems that combine any of the guiding elements discussed above are also possible. For example, a system for rod delivery can include a mixture of one blade and one or more wires on a single screw. Another system for rod delivery can include one tube or tower on a first screw and one or more wire or blade combinations on the second screw. Various combinations of guiding elements that can be used through a single incision are possible.

Similar methods as discussed above with respect to FIGS. 31A to 33 are also applicable to the alternate embodiments of the guiding elements shown in FIGS. 34A to 36C. Such methods can involve the use of one or more assemblies of telescoping guiding elements having adjustable height, whereby one assembly is at a height below an incision and the other assembly is at a height above the incision during use. In some embodiments, the assemblies of telescoping guiding elements are capable of criss-crossing or intersecting. Rod members or other implants can be delivered down the assemblies of telescoping guiding elements and into place into seats of the screw heads.

FIGS. 37A-37D compare the volume of drilled holes and orientations for pedicle screws inserted according to (i) a traditional method along an anteromedial trajectory and (ii) a new method along an anteromediolateral trajectory. FIG. 37(A) shows anterior views illustrating drilled hole volumes for a traditional screw on the left side and a new cortical screw on the right side. FIG. 37(B) shows lateral views illustrating drilled hole volumes for a traditional screw on the right side and a new cortical screw on the left side. FIG. 37(C) shows a radiograph of a pedicle screw placed according to the new method along an anteromediolateral trajectory with cortical bone placement. FIG. 37(D) shows a radiograph of a pedicle screw placed according to the traditional method along an anteromedial trajectory.

A more recent method to place screws into the pedicle uses a medial lateral or anteromediolateral trajectory. The apparatus and method of the present invention can be used with this new cortical screw trajectory approach. By using this cortical approach with the present invention four screws may be placed for a one level fusion and six screws may be placed for a two level fusion all through one small midline incision. (See FIG. 38)

A recent study found that these new cortical trajectory screws demonstrated a 30% increase in uniaxial yield pullout load relative to traditional pedicle screws, although mixed loading demonstrated equivalency between the two trajectories. The new cortical trajectory and screw design have equivalent pullout and toggle characteristics compared with the traditional trajectory pedicle screw, thus confirming preliminary clinical evidence. The 30% increase in failure load of the cortical trajectory screw in uniaxial pullout and its juxtaposition to higher quality bone justify its use in patients with poor trabecular bone quality. (See Santoni, "Cortical bone trajectory for lumbar pedicle screws" in The Spine Journal 9 (2009) 366-373.)

The systems described in the present application can be used to place these screws to project in the medial lateral or anteromediolateral direction for improved results in osteoporotic patients. Traditional screws project in the anterolateral direction. (See FIGS. 37A-37D). The mediolateral placement of screws allow bilateral screws to be placed through a single midline incision. When applied maximally, multi-level fusions can be performed through a single percutaneous midline incision.

Figure 38A:
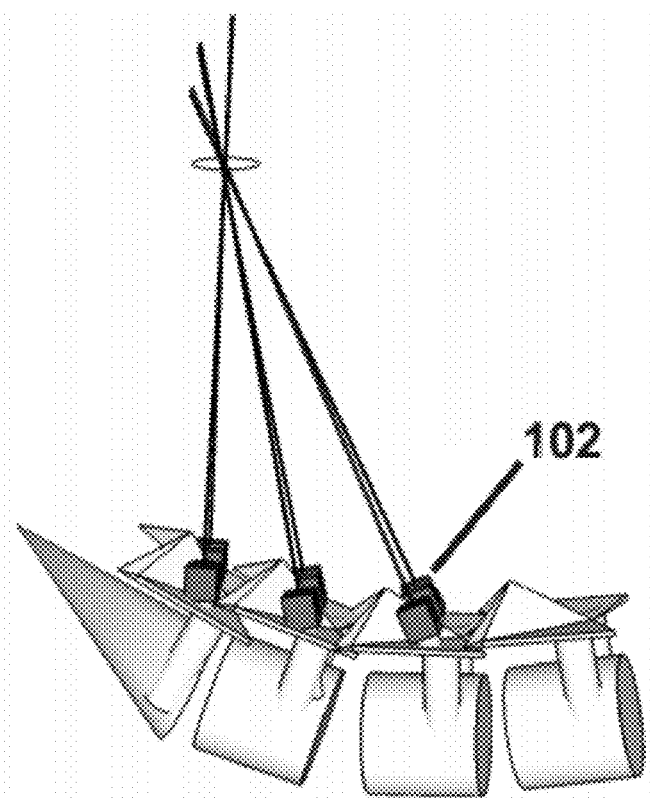
FIGS. 38A and 38B show side and head-on views of a two-level fusion, which involves stabilizing three adjacent vertebral bones spanning two problematic disc spaces, with all guidance elements (wires) on all three vertebrae fitting through a common single incision at skin level using the cortical screw technique shown in FIGS. 37A-37D.
Figure 38B:
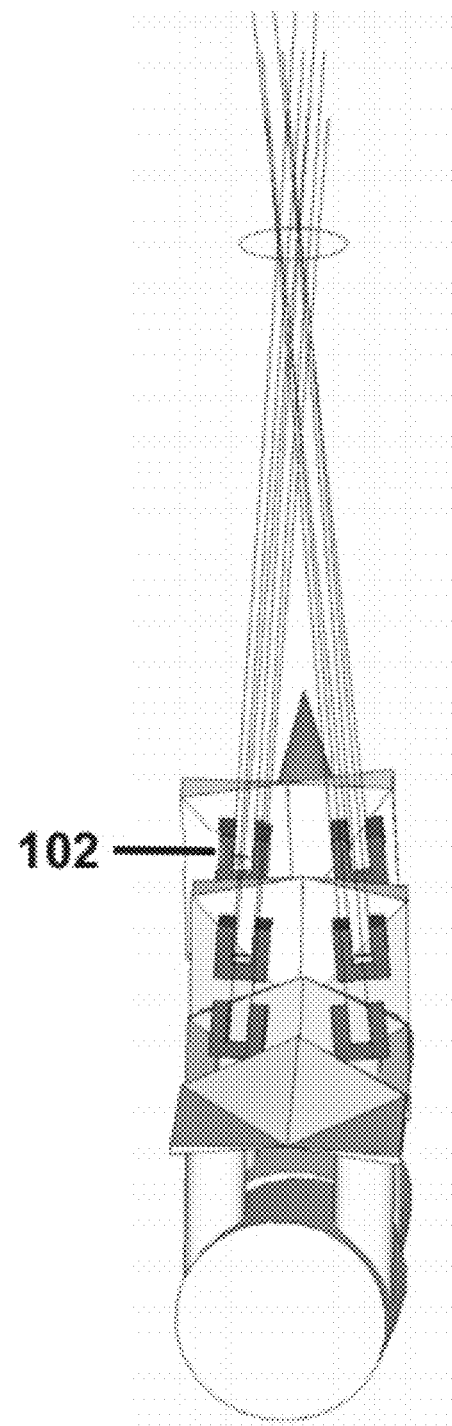

FIGS. 38A and 38B show side and head-on views of a two-level fusion, which involves stabilizing three adjacent vertebral bones spanning two problematic disc spaces, with all guidance elements (e.g., wires) on all three vertebrae fitting through a common single incision at skin level. As shown in the illustrated embodiment, each of the screw heads 102 is operably connected to one or more guidance elements 103 that can be used to deliver one or more rods across three adjacent vertebrae. In other embodiments, rather than using guiding elements comprising wires to stabilize three adjacent vertebral bones, the guiding elements can comprise any of the telescoping guiding elements described above, as well as any of the hybrid guiding elements. Advantageously, the two-level fusion procedure can be performed using a single, relatively small incision through which multiple guiding elements can be inserted.

In addition to cortical screws and pedicle screws, other embodiments of screws placed into vertebrae can benefit from the present embodiments. Recent developments in spinal stabilization have popularized spinous process fixation. However, the implants such as the X-Stop™ (Medtronic), Aspen™ (Lanx), and Spire™ (Medtronic) devices typically need incisions of 4-8 cm. Another embodiment of the current invention uses screws through the spinous process that are connected by a rod type connector to stabilize the spinous process. Bone grafts sized to fit in between the spinous processes allow an inter-spinous process fusion, similar to an inter-vertebral body implant and fusion. The inter-spinous process implant can also be connected to the rod connector for further stabilization. Because the width of the spinous process is typically thinner than the typical length of pedicle screws and cortical screws, the spinous process screws can be modified to include a wing that expands on the other side of the spinous process once the screw travels through the spinous process to the contralateral side. Such a mechanism is similar to the anchors used to secure pictures and hangers onto hollow walls or doors such as Molly bolts. This inter-spinous process stabilization method can also be used in conjunction with a Microfusion TLIF procedure where an interbody implant, pedicle screws, and an inter-spinous process fusion have all been placed through a single 15-20 mm unilateral incision. A further embodiment includes the use of laminar screws where the screw travels through the lamina. Such laminar screws are commonly used for C2 fixation. These and other locations for vertebral screws are easily incorporated into the present embodiments in which guidance elements allow a connector and locking mechanisms to be implanted through a single small incision.

Advantageously, the guiding elements described above, including the wires, plurality of wires simulating a "blade" or "tab," and assemblies of telescoping guiding elements not only provide a minimally invasive means to deliver a spinal implant into a patient, but they are also effective at keeping tissue and muscle away from pathways for implant (e.g., rod) travel. In the case of cortical screws, as shown in FIG. 38A, the medially positioned incision allows the screw to be placed beside the spinous process and muscle. In this case only lateral guiding elements are necessary to retract tissue and muscle because the there is little muscle and tissue medial to the screw.

Figure 39:
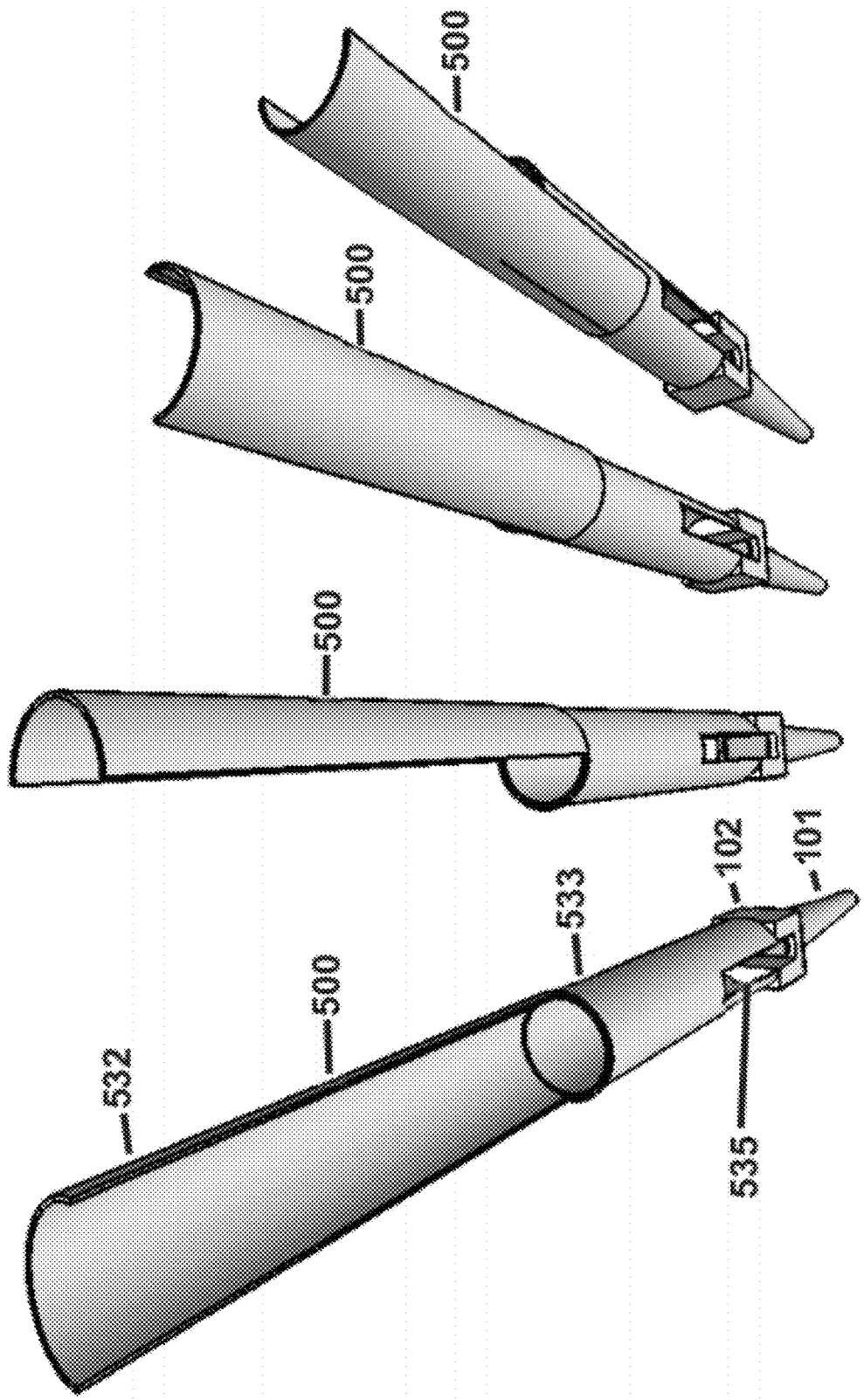
FIG. 39 shows different embodiments of a telescoping guiding element including a half-cylinder portion lowered and rotated to adjust the height and orientation of the guiding element.

FIG. 39 shows different views of a telescoping guiding element including a half-cylinder portion. The telescoping guiding element 500 comprises a cylindrical portion 533 having a window 535 and a half-cylindrical portion 532 slidably mated thereto. The distal end of the telescoping guiding element 500 is connected to a screw having a screw head 102 and shaft 101. The telescoping guiding element 500 is configured such that the half-cylindrical portion 532 can be slidably mated along the outer surface of the cylindrical portion 533. The half-cylindrical portion 532 can move up and down along the outer surface of the cylindrical portion 533, thereby allowing for height adjustment of the telescoping guiding element 500. Other suitable shapes for the upper telescoping portion also include the guide tabs or sleeves of the above referenced U.S. Publication No. 2009-0234392 A1 and U.S. Pat. No. 7,758,584

FIG. 40 shows different embodiments of the telescoping guiding element 500 with the half-cylindrical portion 532. In FIG. 40A, the half-cylindrical portion 532 is attached to outside of the bottom guiding element 500. Alternatively the half-cylindrical portion 532 can be attached to the inside of element 500 thus reducing the diameter of portion 532 (FIG. 40B). Half-cylindrical portions 532 with different diameters allow better intermeshing when two or more half-cylindrical portions meet at a common skin incision. Furthermore, the half-cylindrical portions 532 can have proximal tips that are less than (FIG. 40C) or greater than (FIG. 40D) a half cylinder. The variability allows better intermeshing between multiple telescoping guiding elements at the incision. In fact, different embodiments include the proximal end of the guiding element having any shape that partially fills the perimeter of the skin incision including a partial oval, partial rectangle or square, a partial polygon, a partial helix or spiral, a pointed or tapered proximal end, or guiding elements that project proximally as a spiral or helical shape. The guiding element 500 can be used similarly to other telescoping guiding elements discussed above in that the guiding element 500 can be placed through an incision and then reduced in height to provide more space to allow additional guiding elements to be placed through the same incision. Once a desired number of guiding elements are in place through an incision, one or more spinal implants (e.g., rod members) can be delivered through the guiding elements to assist in vertebral stabilization.

Figure 41:
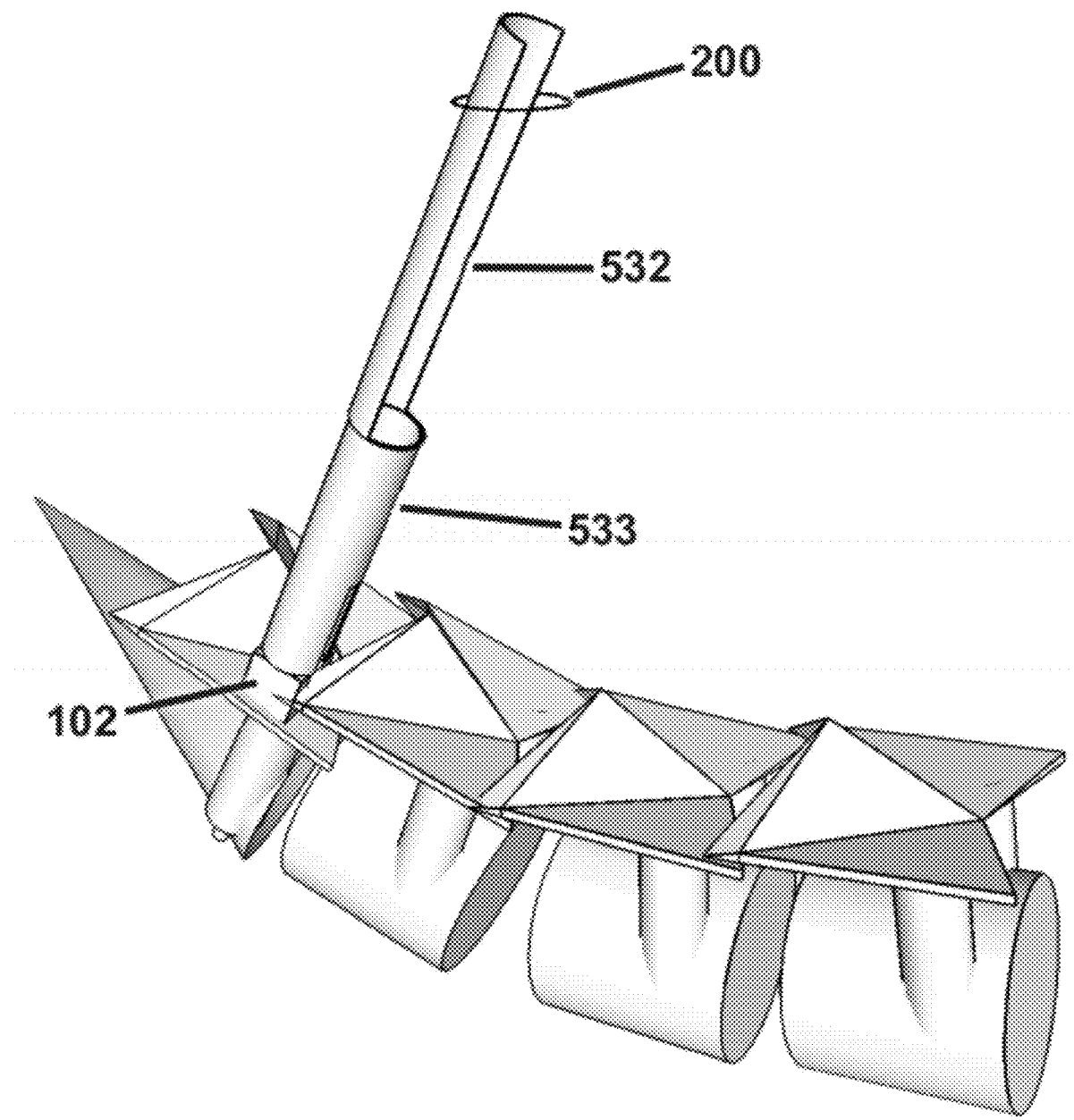
FIG. 41 shows a telescoping guiding element with a half-cylinder portion placed on a vertebral body.

Minimally invasive methods of providing a stabilizing implant across two vertebrae will now be described with respect to FIGS. 41-45. As shown in FIG. 41, an incision 200 is made in a patient. A screw having a screw head 102 can be pre-affixed to a distal end of a telescoping guiding element 500 having a half-cylindrical portion 532 and cylindrical portion 533. The telescoping guiding element 500 can be positioned such that the screw is fixed into a first vertebra. At this point, the telescoping guiding element 500 is of an extended length and passes from the screw head through the incision 200 (see FIG. 41).

Figure 42:
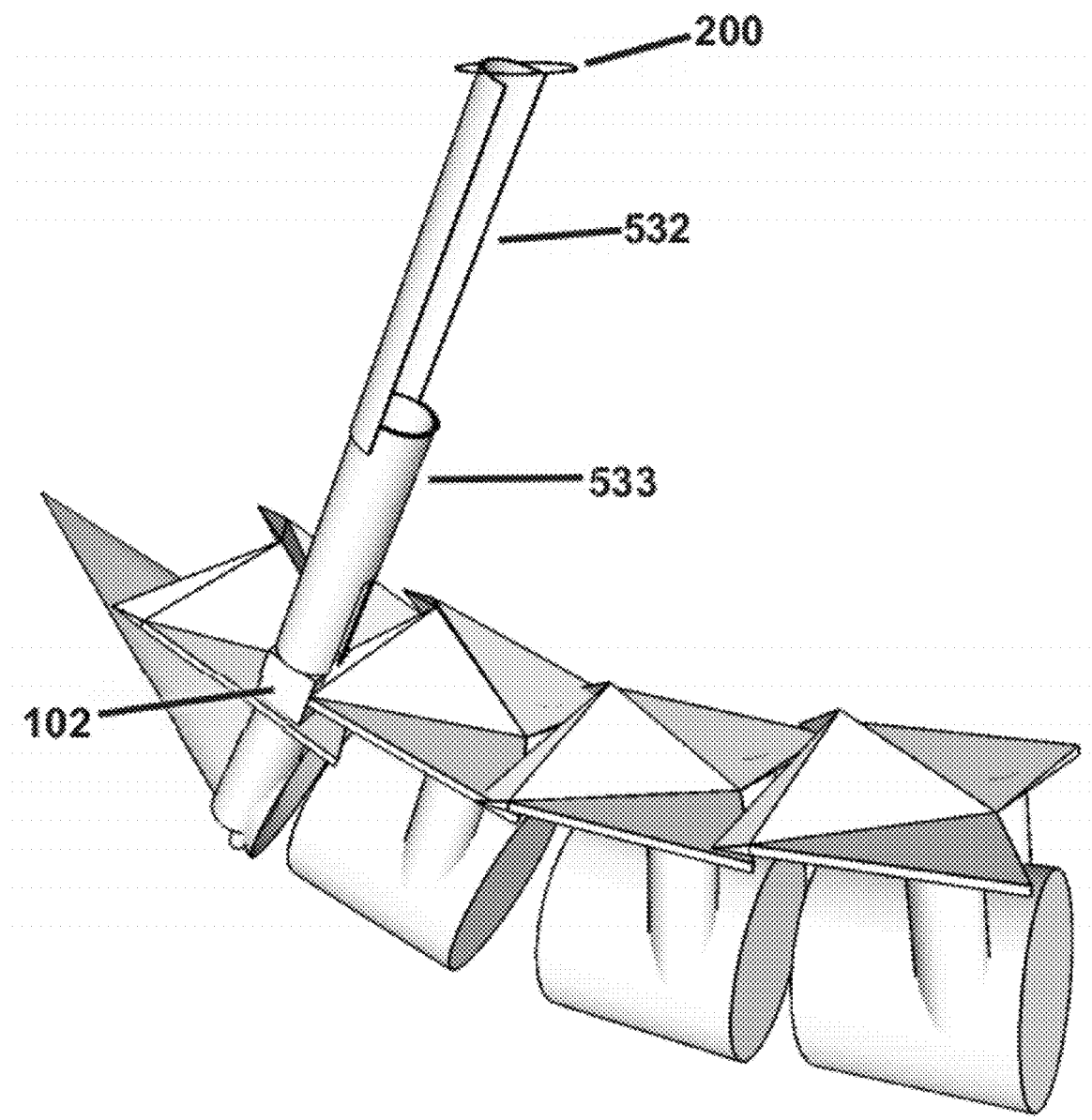
FIG. 42 shows the telescoping guiding element of FIG. 41 with the half-cylinder portion lowered to reduce the height of the guiding element.
Figure 43:
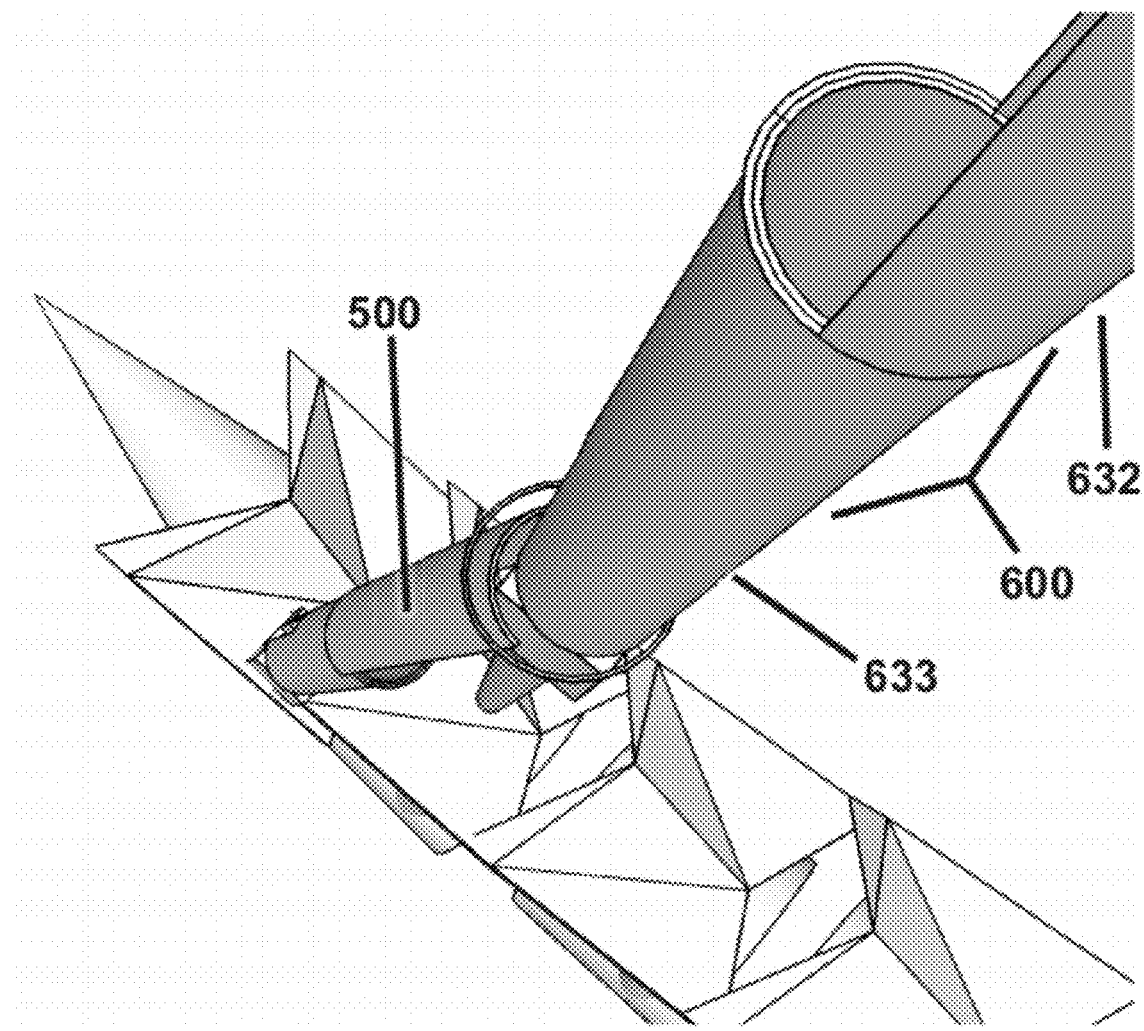
FIG. 43 shows a pair of telescoping guiding elements having half-cylinder portions in use.
Figure 44:
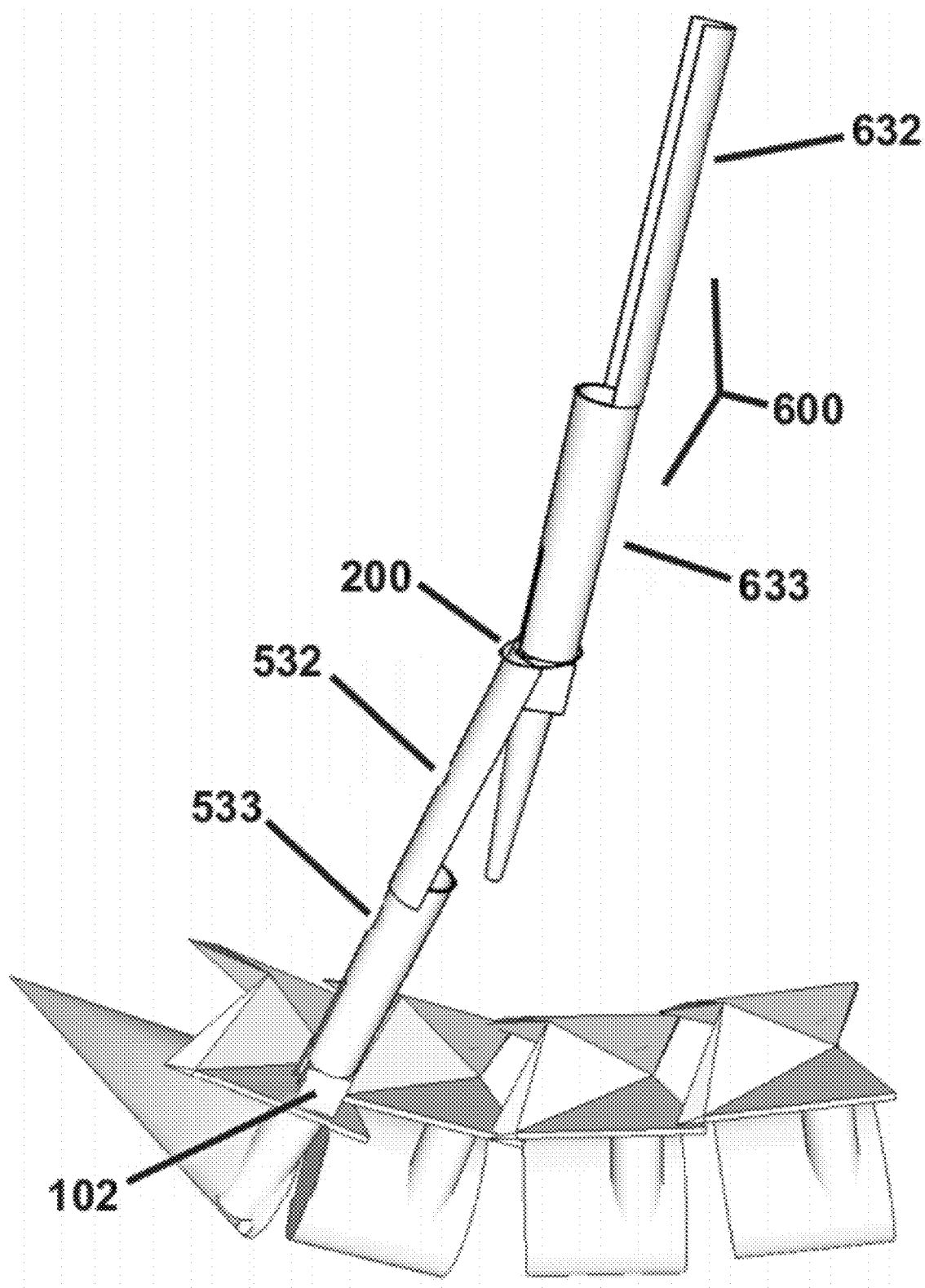
FIG. 44 shows a different view of the pair of telescoping guiding elements of FIG. 43 in use.

Once the telescoping guiding element 500 is positioned, the height of the guiding element 500 can be reduced by sliding the half-cylindrical portion 532 down the body of the cylindrical portion 533, thereby reducing the overall height of the telescoping guiding element 500. As shown in FIG. 42, the telescoping guiding element 500 is reduced to a height wherein the top proximal end of the guiding element 500 is approximately at or below the skin incision 200. By reducing the height of the guiding assembly 500, this advantageously provides a high amount of space for delivering a second telescoping guiding element 600 through the incision 200. Although not shown, wires (such as wire 238) or other mechanisms may be used to maintain contact with the half-cylindrical portion 532.

A second telescoping guiding element 600 having an upper half-cylindrical portion 632 and a lower cylindrical portion 633 can then be delivered through the incision 200. Like the first telescoping guiding element 500, the distal end of the second telescoping guiding element is fixed to a screw via a screw head 102. As shown from the different perspectives in FIGS. 43 and 44, the half-cylindrical portion 532 of the first telescoping guiding element 500 provides plenty of room for the second telescoping guiding element 600 to be delivered through the same incision 200.

After delivering the second telescoping guiding element 600 through the same incision 200, the second screw can be affixed to a second vertebral body. The system now comprises two telescoping guiding elements 500, 600 having proximal end portions at or near the incision 200. The half-cylindrical portions 532, 632 of guiding elements each provide a channel through which it is possible to deliver a spinal implant (e.g., a rod member) therethrough. The second half-cylindrical portion 632 may also be slid down to the level of the skin incision 200, as desired. As shown in FIG. 45, a rod member (not shown) can be guided via the interior of the half-cylindrical portion 632 down to the cylindrical portion 633. One end of the rod member can pass through the window 655 of the second guiding element 600 and can pass into the window 555 of the first guiding element. The rod member is now in a position such that a first end can rest on a first seat in the first screw head and a second end can rest on a second seat in the second screw head, thereby serving as a stabilizing member across two vertebrae.

FIG. 45 shows the half-cylindrical guiding elements at skin level in a superior-inferior orientation for the elements. Because the half-cylindrical guiding elements 532 and 632 can rotate on the lower cylindrical portions 533 and 633, the orientation for the guiding elements at skin level can also be medial-lateral or any orientation reachable by rotating both upper half-cylindrical portions 532 and 632. The embodiment shown in FIG. 45 can also be accomplished without telescoping means. By measuring the desired height of the half-cylindrical guiding element from the top of the screw head to the incision, fixed and non-telescoping half-cylindrical guiding elements with the exact measured length can be attached to the top of the screw head and placed with the screw into the incision. The height of each half-cylindrical guiding element can be measured exactly by a measuring tool that slides over the guide wire used to access the pedicle or other part of the vertebrae through which the screw is to be inserted. By accounting for the height of the screw head in this measurement, the height of the guiding element that exactly comes to the incision can be measured. In this manner, the embodiment shown in FIGS. 42-45 can be performed without any telescoping means or adjustment in height. Desirably, the height of the guiding elements is kept at the level of the skin incision to minimize interference with other screws and guiding elements.

FIGS. 46A-46D show embodiments of a guiding element 700, 710 having expandable blades or tabs. In one embodiment, a blade 700 is attached to the screw head 102, and a second blade 710 can be separated from blade 700 using a retractor mechanism at the proximal ends outside the skin incision. In one embodiment, the two blades 700 and 710 may not be completely connected, but instead just one blade (e.g., blade 700) is attached to the screw head. In this manner, blade 710 may move freely and is more like a retractor. A retractor mechanism is used at the proximal end to spread apart, hold, lock and/or collapse the two blades as necessary. As shown in FIGS. 46B-46D, the blades 710 can be expanded such that a channel is created for rod or tool delivery. In some embodiments, it is possible to criss-cross a pair of guiding elements 700 at or near an incision to thereby introduce a rod minimally invasively. In one embodiment, the individual blades or tabs 710 themselves are capable of expanding apart. The two blades 700 and 710 may be connected with side connectors like a foldable fan or accordion, such that they can move from a low profile configuration as shown in FIG. 46A to a wider, larger profile configuration in FIG. 46D.

Many of the inventive features discussed above (e.g., providing criss-crossing guiding elements in the form of wires, blades/tabs, or telescoping elements) can also be applied to improve existing devices as featured in other applications. For example, the fixation system in U.S. Pat. No. 7,758,584 to Bankoski et al. (assigned to Synthes) can be improved by including telescoping features, which would allow its multiple implant holders in the patent to be criss-crossed at or near an incision, thereby reducing the size of the incision. Currently, the lateral implant holder, sleeve, and tissue protection portion in the '584 patent appear to extend through the skin incision and has no ability to telescope to different heights, including at or below the skin surface. Furthermore, the '584 patent describes the intermeshing of guiding tubes with helical shaped cutouts. Since the helical cutouts have a fixed angle, the intermeshing is accomplished only when the angle of the helical cutout matches the lordotic curvature of the spine. Since the lordotic angle varies from patient to patient and level to level, the fixed helical cutout is not practically amenable to optimal intermeshing and cannot minimize the skin incision. The fixation system in U.S. 2009/0234392 to Dziedzic et al. (assigned to DePuy Spine, Inc.) can also be improved by including telescoping features, which would similarly allow the multiple guide tabs in the publication to be criss-crossed at or near an incision, thereby reducing the size of the incision. U.S. Pat. No. 7,846,093 to Gorek et al. (assigned to K2M, Inc.) can also benefit from telescoping features. Moreover, none of these applications apply guiding elements in the form of wires as in the present application, which can easily extend through a number of various angles from a vertebral body to an incision, thereby allowing the guidance elements to intersect at or near an incision with ease and increase minimal invasiveness. Furthermore, none of these applications teaches that intersection of the guiding elements at or near the skin incision permits the smallest incision size by maximizing the overlap of guiding elements at the incision, nor do they teach a method to insert two or more screws through such a small incision without interference between screws and guidance elements. Additionally, the rod and locking mechanism in each of these applications require visualization of the rod and screw head. In certain embodiments of the present application, the rod and locking mechanisms are trapped and confined to fit into the screw head such that the entire process can be performed percutaneously without needing to look into the incision. This ability affords greater flexibility, ease, and permits a smaller, possibly the smallest skin incision. Each of the disclosures of the '584 patent, the '392 Publication and the '093 patent as specified in this paragraph are incorporated by reference in their entireties, and any of the inventive features discussed herein are applicable to these references.

Further, any of the procedures using the guiding elements described above can be performed with the assistance of one or more robots. The use of robots advantageously provides increased precision and could be very useful in delivering screws, rods, locking assemblies, and guiding tools down the guiding elements. Robotic assistance can be further improved by endoscopic visualization as well as stereotactic guidance. These tools help to speed up surgical time and reduce the size of the incision towards the theoretical limit of the width of a single screw for spinal fusions.

The present invention is not limited to the embodiments described above. Various changes and modifications can, of course, be made, without departing from the scope and spirit of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed:

1. A system for performing spine stabilization through an opening in skin of a patient, comprising:
   a first screw having a screw head, the first screw configured to be implanted in a first vertebra;
   a first guiding element comprising an adjustable height component, wherein the first guiding element is configured to be detachably connected to the first screw, and wherein the adjustable height component is configured to adjust the height of the first guiding element before it is detached from the first screw;
   a second screw having a screw head, the second screw configured to be implanted in a second vertebra;
   a second guiding element configured to be detachably connected to the second screw; and
   a spinal implant sized and configured to be delivered down one or both of the first and second guiding elements, the spinal implant having a first portion that is configured to be fixed to the first screw head and a second portion that is configured to be fixed to the second screw head;
   wherein the first screw with the first guiding element and the second screw with the second guiding element are configured to be delivered into the first and second vertebra, respectively, and the adjustable height component of the first guiding element is adjustable to reduce a height of the first guiding element at or below a level of the skin opening to allow the second guiding element to extend through the skin opening when the second screw is implanted in the second vertebra.

2. The system of claim 1, wherein the adjustable height component comprises telescoping components.

3. The system of claim 1, wherein the second guiding element comprises an adjustable height component.

4. The system of claim 3, further comprising first extension elements in contact with a proximal portion of the adjustable height component of the first guiding element and second extension elements in contact with a proximal portion of the adjustable height component of the second guiding element, the first and second extension elements capable of crisscrossing while still providing a pathway to deliver a spinal implant.

5. The system of claim 3, wherein the adjustable height components of the first and second guiding elements are partial cylinders configured to couple at the skin incision to form an elliptical or partially elliptical portal for tools and implants to reach the first and second guiding elements and screw heads.

6. The system of claim 1, wherein the second guiding element is non-telescoping and has a fixed length.

7. The system of claim 6, wherein the second guiding element comprises a rigid tube or one or more blades having a height that extends through and above the skin opening when the second screw is implanted in the second vertebra.

8. The system of claim 1, wherein the adjustable height component comprises a plurality of cylindrical members, each cylindrical member comprising a complete or partial cylinder.

9. The system of claim 1, wherein the adjustable height component comprises a plurality of blades.

10. The system of claim 1, further comprising one or more extension elements attached to the adjustable height component, wherein the one or more extension elements are configured to extend through the skin opening when the adjustable height component is reduced in height at or below the skin opening.

11. The system of claim 1, wherein the adjustable height component comprises a lower cylinder detachably connected to the screw head and a partial cylinder slidably coupled to the lower cylinder.

12. The system of claim 1, further comprising a third screw having a screw head and a third guiding element detachably connected to the third screw, the third screw configured to be implanted in a third vertebra.

13. The system of claim 12, wherein the third guiding element comprises telescoping components.

14. The system of claim 1, wherein the spinal implant is sized to be fixed to the first and second screw heads and is further configured to have one or more detachable flexible extensions at one or more ends of the spinal implant that prevents the spinal implant from rotating and further extends through one or more guiding elements to keep the ends of the spinal implant within the guiding elements and the screw heads when the spinal implant is delivered to the first and second screws.

15. The system of claim 1, wherein a width of the skin opening is smaller than the combined widths of the first screw and the second screw.

16. The system of claim 1, wherein the adjustable height component is capable of bending at the skin level to reduce a distance of the components above the skin opening to the skin opening itself.

17. A system for performing spine stabilization on a patient through an opening in skin of a patient, comprising:
   a first screw having a screw head configured to be implanted in a first vertebra;
   a second screw having a screw head configured to be implanted in a second vertebra;
   at least one or both of: (i) a first guiding element comprising an adjustable height component that is configured to be detachably connected to the first screw, wherein the first guiding element is adjustable to reduce a height of the first guiding element at or below a level of the skin opening before the first guiding element is detached from the first screw, and (ii) one or more flexible wire(s) configured to extend upwardly from the first screw and/or from the first guiding element and through the skin opening when the second screw is implanted in the second vertebra, wherein the one or more flexible wire(s) are movable relative to the first screw when attached to the first screw and/or the first guiding element;
   a second guiding element configured to be detachably connected to the second screw, the second guiding element comprising a rigid or semi-rigid material configured to extend through and above the skin opening when the second screw is implanted in the second vertebra; and
   a spinal implant member connectable between the first screw and the second screw.

18. The system of claim 17, wherein one or both of the first and second guiding elements comprise one or more tubes, partial tubes, or blades.

19. The system of claim 17, comprising one or more flexible wires configured to extend upwardly from the first screw, wherein the one or more flexible wires are detachably connected to either the first screw or a guiding element configured to be detachably connected to the first screw.

20. The system of claim 17, wherein the second guiding element comprises telescoping components configured to provide an adjustable height to the second guiding element.

21. A method of treating the spine, comprising:
  making an incision in the skin of a patient to provide access to a spinal location;
  delivering a first screw through the incision and into a first vertebra and a second screw through the same incision and into a second vertebra, wherein at least one of the first screw and second screw has detachably connected thereto a guiding element extending upwardly through the incision, wherein the guiding element comprises an adjustable height component configured to adjust a height of the guiding element at or below a level of the skin incision before the guiding element is detached from one of the first screw or second screw;
  delivering a rod or flexible connector to the screws; and
  locking the rod or flexible connector to each of the screws.

22. The method of claim 21, wherein the adjustable height component comprises a plurality of telescoping guiding elements.

23. The method of claim 22, wherein the telescoping guiding elements comprises a plurality of tubes, partial tubes, or blades.

24. The method of claim 22, wherein the telescoping guiding elements further comprise at least one wire or extension element extending upwardly away from the vertebrae through the incision when the screw or screws are delivered in the vertebrae.

25. The method of claim 22, wherein delivering the rod or flexible connector comprises passing the rod or flexible connector through a window in one of the telescoping guiding elements detachably connected to the first screw into contact with the second screw.

26. The method of claim 25, wherein delivering the rod or flexible connector further comprises passing the rod into a window in one of a plurality of telescoping guiding elements detachably connected to the second screw.

27. The method of claim 21, wherein both the first screw and the second screw have detachably connected thereto a guiding element, wherein the guiding element detachably connected to the first screw comprises an adjustable height component having a first plurality of telescoping guiding elements and the guiding element detachably connected to the second screw comprises an adjustable height component having a second plurality of telescoping guiding elements, the method comprising:
  delivering the first screw through the incision and into the first vertebra with the first plurality of telescoping guiding elements extending through the incision;
  reducing a height of the first plurality of telescoping guiding elements so that an uppermost one of the telescoping guiding elements is positioned at or below the incision; and
  delivering the second screw through the same incision into the second vertebra with the second plurality of telescoping guiding elements extending through the incision.

28. The method of claim 21, wherein the first screw has detachably connected thereto a guiding element comprising an adjustable height component having plurality of telescoping guiding elements, and the second screw has detachably connected thereto a non-telescoping guiding element.

29. A method of treating the spine, comprising:
  making an incision in the skin of a patient to provide access to a spinal location;
  delivering a first screw through the incision and into a first vertebra, wherein the first screw has detachably connected thereto a guiding element having a height, after implantation of the first screw, at or below a level of the skin incision before the guiding element is detached from the first screw;
  delivering a second screw through the same incision and into a second vertebra, wherein the second screw has detachably connected thereto a second guiding element comprising a rigid or semi-rigid material extending through and above the skin incision when the second screw is implanted in the second vertebra;
  delivering a rod or flexible connector to the screws; and
  locking the rod or flexible connector to each of the screws.

30. The method of claim 29, wherein the first screw is delivered into the first vertebra having an extension element or flexible wire attached to a proximal end of the first guiding element.

* * * * *